United States Patent
Charvat et al.

(10) Patent No.: US 7,683,176 B2
(45) Date of Patent: Mar. 23, 2010

(54) TRIAZOLYL PYRIDYL BENZENESULFONAMIDES

(75) Inventors: Trevor T. Charvat, San Jose, CA (US); Cheng Hu, Menlo Park, CA (US); Jeff Jin, Fremont, CA (US); Yandong Li, San Jose, CA (US); Anita Melikian, San Francisco, CA (US); Andrew M. K. Pennell, San Francisco, CA (US); Sreenivas Punna, Sunnyvale, CA (US); Solomon Ungashe, Fremont, CA (US); Yibin Zeng, San Mateo, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 145 days.

(21) Appl. No.: 11/775,601

(22) Filed: Jul. 10, 2007

(65) Prior Publication Data

US 2008/0039504 A1    Feb. 14, 2008

Related U.S. Application Data

(60) Provisional application No. 60/831,042, filed on Jul. 14, 2006, provisional application No. 60/945,854, filed on Jun. 22, 2007.

(51) Int. Cl.
*C07D 401/04* (2006.01)
(52) U.S. Cl. .................................. 546/272.4
(58) Field of Classification Search ............... 546/272.4
See application file for complete search history.

(56) References Cited

U.S. PATENT DOCUMENTS

| 6,939,885 | B2 | 9/2005 | Ungashe et al. |
| 7,227,035 | B2 | 6/2007 | Ungashe et al. |
| 2004/0167113 | A1 | 8/2004 | Ungashe et al. |
| 2004/0171654 | A1 | 9/2004 | Ugashe et al. |
| 2005/0137193 | A1 | 6/2005 | Ungashe et al. |
| 2005/0165067 | A1 | 7/2005 | Ungashe et al. |
| 2006/0111351 | A1 | 5/2006 | Ungashe et al. |
| 2006/0173019 | A1 | 8/2006 | Ungashe et al. |
| 2007/0021466 | A1 | 1/2007 | Ungashe et al. |
| 2007/0037794 | A1 | 2/2007 | Ungashe et al. |
| 2007/0203131 | A1 | 8/2007 | Ungashe et al. |
| 2008/0039465 | A1 | 2/2008 | Charvat et al. |

FOREIGN PATENT DOCUMENTS

| WO | WO 01-77087 | 10/2001 |
| WO | WO 2004/058741 | 7/2004 |
| WO | WO 2005/004818 | 1/2005 |
| WO | WO 2005-113513 | 12/2005 |
| WO | WO 2007/014008 A2 | 1/2007 |
| WO | WO 2007/014054 A2 | 1/2007 |
| WO | WO 2008-008374 A2 | 1/2008 |
| WO | WO 2008-008431 A2 | 1/2008 |

*Primary Examiner*—Patricia L Morris
(74) *Attorney, Agent, or Firm*—Brinks Hofer Gilson & Lione

(57) ABSTRACT

Compounds are provided that act as potent antagonists of the CCR2 or CCR9 receptor. Animal testing demonstrates that these compounds are useful for treating inflammation, a hallmark disease for CCR2 and CCR9. The compounds are generally aryl sulfonamide derivatives and are useful in pharmaceutical compositions, methods for the treatment of CCR2-mediated diseases, CCR9-mediated diseases, as controls in assays for the identification of CCR2 antagonists and as controls in assays for the identification of CCR9 antagonists.

18 Claims, No Drawings

TRIAZOLYL PYRIDYL BENZENESULFONAMIDES

RELATED APPLICATIONS

This application claims priority to U.S. provisional application Ser. No. 60/831,042 filed Jul. 14, 2006. This application claims priority to U.S. provisional application Ser. No. 60/945,854, filed Jun. 22, 2007. The disclosures of these priority applications are incorporated herein in their entirety.

FEDERALLY SPONSORED RESEARCH OR DEVELOPMENT

The present invention described herein was supported at least in part by NIH (U19-AI056690-01). The government may have certain rights in the invention.

BACKGROUND

The present invention provides compounds, pharmaceutical compositions containing one or more of those compounds or their pharmaceutically acceptable salts, which are effective in inhibiting the binding or function of various chemokines to chemokine receptors. As antagonists or modulators of chemokine receptors, the compounds and compositions have utility in treating various immune disorder conditions and diseases.

Chemokines, also known as chemotactic cytokines, are a group of small molecular-weight proteins that are released by a wide variety of cells and have a variety of biological activities. Chemokines attract various types of cells, of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, Cytokine, 3:165-183 (1991), Schall et al., Curr. Opin. Immunol., 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., J. Am. Soc. Nephrol., 11:152-76 (2000); Morii et al., J. Diabetes Complications, 17:11-5 (2003); Lloyd et al. J. Exp. Med., 185:1371-80 (1997); Gonzalez-Cuadrado et al. Clin. Exp. Immunol, 106:518-22 (1996); Eddy & Giachelli, Kidney Int., 47:1546-57 (1995); Diamond et al., Am. J. Physiol., 266:F926-33 (1994)). In humans, CCR2 and ligand MCP-1 are among the proteins expressed in renal fibrosis, and are correlated with the extent of macrophage infiltration into the interstitium (Yang et al., Zhonghua Yi Xue Za Zhi, 81:73-7 (2001); Stephan et al., J. Urol., 167:1497-502 (2002); Amann et al., Diabetes Care, 26:2421-5 (2003); Dai et al., Chin. Med. J. (Engl), 114:864-8 (2001)). In animal models of renal fibrosis, blockade of CCR2 or MCP-1 leads to a marked reduction in severity of renal inflammation (Kitagawa et al., Am. J. Pathol., 165:237-46 (2004); Wada et al., Am. J. Pathol., 165:237-46 (2004); Shimizu et al., J. Am. Soc. Nephrol., 14:1496-505 (2003)).

Rheumatoid arthritis is a chronic disease of the joints characterized by synovial inflammation that leads to the destruction of cartilage and bone. Although the underlying causes of the disease are unknown, it is believed that macrophages and Th-1 type T cells play a key role in the initiation and perpetuation of the chronic inflammatory process (Vervoordeldonk et al., Curr. Rheumatol. Rep., 4:208-17 (2002)).

MCP-1 is among the several chemokines, including MIP-1α and IL-8, identified in rheumatoid synovium (Villiger et al., J. Immunol., 149:722-7 (1992); Scaife et al., Rheumatology (Oxford), 43:1346-52 (2004); Shadidi et al., Scand. J. Immunol., 57:192-8 (2003); Taylor et al., Arthritis Rheum., 43:38-47 (2000); Tucci et al., Biomed. Sci. Instrum., 34:169-74 (1997)). Chemokine receptors CCR1, CCR2, CCR3 and CCR5 are up-regulated in the joints from arthritic mice (Plater-Zyberk et al., Immunol. Lett., 57:117-20 (1997). Blockade of MCP-1 activity using a CCR2 antagonist or an antibody against MCP-1 have been shown efficacious in reducing joint inflammation in experimental models of rheumatoid arthritis (Gong et al., J. Exp. Med., 186:131-7 (1997); Ogata et al., J. Pathol., 182:106-14 (1997)).

Chemokine receptor-mediated infiltration of macrophages in the fat tissues may also contribute to the complications arising from obesity, a condition resulting from excessive storage of fat in the body. Obesity predisposes the affected individuals to many disorders, such as non-insulin-dependent diabetes, hypertension, stroke, and coronary artery disease. In obesity, adipose tissues have altered metabolic and endocrine functions that lead to an increased release of fatty acids, hormones, and pro-inflammatory molecules. Adipose tissue macrophages are believed to be a key source of pro-inflammatory cytokines including TNF-alpha, iNOS and IL-6 (Weisberg et al., J. Clin. Invest., 112:1796-808 (2003)). Recruitment of macrophages to the adipose tissue is likely mediated by MCP-1 produced by adipocytes (Christiansen T, et al., Int J Obes (Lond). 2005 January; 29(1):146-50; Sartipy et al., Proc. Natl. Acad. Sci. U.S.A., 100:7265-70 (2003)).

Elevated MCP-1 may induce adipocyte differentiation and insulin resistance, and contribute to pathologies associated with hyper-insulinemia and obesity. MCP-1 is over-expressed in plasma in obese mice compared to lean controls and white adipose is a major source. MCP-1 has also been shown to accelerate wound healing, and has a direct angiogenic effect on epithelial cells, and may play a direct role in the remodeling of adipose tissue in obesity. (Sartipy P, Loskutoff D J., Proc, Natl. Acad. Sci. U.S.A., 100:7265 (2003)).

MCP-1 plasma levels are substantially increased in Diet Induce Obesity (DIO) mice, and a strong correlation between plasma MCP-1 levels and body weight has been identified. Furthermore, elevation of MCP-1 induced by high fat diet causes changes in the CD11b positive monocyte population in DIO mice. (Takahashi K, et al., J. Biol. Chem., 46654 (2003)).

Furthermore, chronic inflammation in fat is thought to play a crucial role in the development of obesity-related insulin resistance (Xu H. et al., J Clin Invest. 2003 December; 112 (12):1821-30). It has been proposed that obesity related insulin resistance is, at least in part, a chronic inflammatory disease initiated in adipose tissue, Many inflammation and macrophage specific genes are dramatically upregulated in white adipose tissue in mouse models of genetic and high fat diet-induced obesity (DIO), and this upregulation precedes a dramatic increase in circulating insulin.

Increased expression levels of monocyte CCR2 and monocyte chemoattractant protein-1 in patients with diabetes mellitus (Biochemical and Biophysical Research Communications, 344(3):780-5 (2006)) were found in a study involving diabetic patients. Serum MCP-1 concentrations and surface expression of CCR2 on monocytes in diabetic patients were significantly higher than in non-diabetics, and the serum MCP-1 levels correlated with HbA1c, triglycerides, BMI, hs-CRP. Surface expression levels of CD36 and CD68 on monocytes were significantly increased in diabetic patients and more unregulated by MCP-1 in diabetics, augmenting uptake of ox-LDL, and hence potentially foam cell transformation. Elevated serum MCP-1 and increased monocyte CCR2, CD36, CD68 expression correlated with poor blood glucose control and potentially correlate with increased vessel wall monocyte recruitment.

MCP-1 is a potential player in negative cross talk between adipose tissue and skeletal muscle (Bianco J J, et al., Endocrinology, 2458 (2006)). MCP-1 can significantly reduce insulin-stimulated glucose uptake, and is a prominent inducer of insulin resistance in human skeletal muscle cell. Adipose tissue is a major secretory and endocrine active organ producing bioactive proteins regulating energy metabolism and insulin sensitivity.

CCR2 modulates inflammatory and metabolic effects of high-fat feeding (Weisberg S P, et al., J. Clin. Invest., 115 (2006)). Genetic deficiency in CCR2 reduced food intake and attenuated the development of obesity in mice fed a high fat diet. In obese mice matched for adiposity, CCR2 deficiency reduced macrophage content and inflammatory profile of adipose tissue, increased adiponectin expression, and improved glucose homeostatis and insulin sensitivity. In lean animals, no effect of CCR2 genotype on metabolic trait was found. In high-fat diet mice, CCR2 genotype modulated feeding, the development of obesity and adipose tissue inflammation. Once established, short term antagonism was shown to attenuate macrophage accumulation in adipose tissue and insulin resistance.

Chemokine and chemokine receptors are the key regulators of immune cell trafficking. MCP-1 is a potent chemoattractant of monocytes and T cells; its expression is induced under inflammatory conditions including proinflammatory cytokine stimulations and hypoxia. The interaction between MCP-1 and CCR2 mediates migration of monocytes, macrophage as well as activated T cells and play a key role in the pathogenesis of many inflammatory diseases. Inhibition of CCR2 functions using small molecule antagonists described in this invention represents a new approach for the treatments of inflammatory disorders.

Psoriasis is a chronic inflammatory disease characterized by hyperproliferation of keratinocytes and pronounced leukocyte infiltration. It is known that keratinocytes from psoriasis lesion express abundant CCR2 ligand MCP-1, particularly when stimulated by proinflammatory cytokines such as TNF-α (Vestergaard et al., Acta. Derm. Venereol., 84(5): 353-8 (2004); Gillitzer et al., J. Invest. Dermatol., 101(2): 127-31 (1993); Deleuran et al., J. Dermatol. Sci., 13(3):228-36 (1996)). Since MCP-1 can attract migration of both macrophages and dendritic cells expressing CCR2 to the skin, this receptor and ligand pair is believed to be important in regulating the interaction between proliferating keratinocytes and dermal macrophage during the development of psoriasis. A small molecule antagonist may thus be useful in the treatment of psoriasis.

In addition to inflammatory diseases, chemokines and chemokine receptors have also been implicated in cancers (Broek et al., Br. J. Cancer, 88(6):855-62 (2003)). Tumor cells stimulate the formation of stroma that secretes various mediators pivotal for tumor growth, including growth factors, cytokines, and proteases. It is known that the level of MCP-1 is associated significantly with tumor-associated macrophage accumulation, and prognostic analysis reveals that high expression of MCP-1 is a significant indicator of early relapse in breast cancer (Ueno et al., Clin. Cancer Res., 6(8):3282-9 (2001)). A small molecule antagonist of a chemokine may thus be able to reduce the release of growth-stimulating cytokines by blocking accumulation of macrophages at sites of tumor formation.

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease causing T cells to the intestine. See for example, Zaballos et al., J. Immunol., 162(10):5671 5675 (1999); Kunkel et al., J. Exp. Med., 192(5):761-768 (2000); Papadakis et al., J. Immunol., 165(9):5069-5076 (2000); Papadakis et al., Gastroenterology, 121(2):246-254 (2001); Campbell et al., J. Exp. Med., 195(1):135-141 (2002); Wurbel et al., Blood, 98(9):2626-2632 (2001); and Uehara et al., J. Immunol., 168(6):2811-2819 (2002). Rivera-Nieves, et al., Gastroenterology, 2006 November; 131(5):1518-29; and Kontoyiannis et al., J. Exp. Med., Vol. 196, Number 12, Dec. 16, 2002. In addition CCR9 bearing lymphocytes have been show to mediate the pathology of filariasis (lymphatic filarial disease) and inhibition of CCR9 has been correlated with reduction of the pathology associated with such conditions. See for example Babu et al., Journal of Infectious Diseases, 191: 1018-26, 2005.

PCT Published Application WO 2003/099773 (Millennium Pharmaceuticals, Inc.) discloses compounds which can bind to CCR9 receptors of the formula

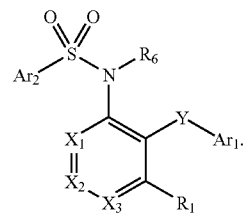

PCT Published Application WO 2005/004810 (Merck & Co., Inc.) discloses brandykinin B1 antagonists or inverse agonists of the formula

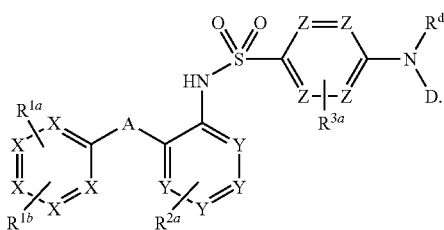

US Published Patent Application 2007/0037794 A1 (ChemoCentryx, Inc.) discloses CCR2 modulators of the formula

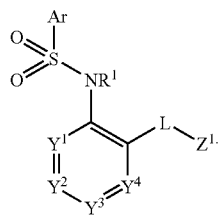

BRIEF SUMMARY

The present invention is directed to compounds and pharmaceutically acceptable salts thereof, compositions, and methods useful in modulating chemokine activity. The compounds and salts thereof, compositions, and methods described herein are useful in treating or preventing chemokine-mediated conditions or diseases, including certain inflammatory and immunoregulatory disorders and diseases.

The compounds of the present invention have been shown to modulate one or more of CCR2, CCR3, CCR4, CCR5, CCR6, CCR7, CCR8, CCR9, CCR10, CXCR3, CXCR4, CXCR5, and CX3CR1. In particular, various compounds of the present invention modulate CCR2 and CCR9 as shown in the examples.

In one embodiment, the present compound may be represented by formula (I) or salts thereof:

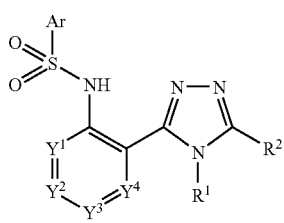

I where Ar, $R^1$, $R^2$, $Y^1$, $Y^2$, $Y^3$, and $Y^4$ are as defined below.

In another aspect, the present invention provides compositions useful in modulating chemokine activity. In one embodiment, a composition according to the present invention comprises a compound according to the invention and a pharmaceutically acceptable carrier or excipient.

In yet another aspect, the present invention provides a method of modulating chemokine function in a cell, comprising contacting the cell with a therapeutically effective amount of a compound or composition according to the invention.

In still another aspect, the present invention provides a method for modulating chemokine function, comprising contacting a chemokine receptor with a therapeutically effective amount of a compound or composition according to the invention.

In still another aspect, the present invention provides a method for treating a chemokine-mediated condition or disease, comprising administering to a subject a safe and effective amount of a compound or composition according to the invention.

In addition to the compounds provided herein, the present invention further provides pharmaceutical compositions containing one or more of these compounds, as well as methods for the use of these compounds in therapeutic methods, primarily to treat diseases associated with chemokine signaling activity.

DETAILED DESCRIPTION

General

The present invention is directed to compounds and salts thereof, compositions and methods useful in the modulation of chemokine receptor function, particularly CCR2 or CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR2 or CCR9 receptor. Accordingly, the compounds of the present invention are compounds which modulate at least one function or characteristic of mammalian CCR2 or CCR9, for example, a human CCR2 or CCR9 protein. The ability of a compound to modulate the function of CCR2 or CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred.

The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a mono-haloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

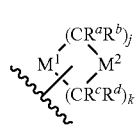

AA where formula (AA) is attached via a free valence on either $M^1$ or $M^2$; $M^1$ represents O, $NR^e$, or $S(O)_i$; $M^2$ represents $CR^fR^g$, O, S(O)$_l$, or $NR^e$; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^h$, —$CO_2R^h$, —$CONR^hR^i$, —$NR^hCOR^i$, —$SO_2R^h$, —$SO_2NR^hR^i$, —$NSO_2R^hR^i$ —$NR^hR^i$, —$OR^h$, -$Q^1COR^h$, -$Q^1CO_2R^h$, -$Q^1CONR^hR^i$, -$Q^1NR^hCOR^i$, -$Q^1SO_2R^{28}$, -$Q^1SO_2NR^hR^i$, -$Q^1NSO_2R^hR^i$, -$Q^1NR^hR^i$, -$Q^1OR^h$, wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of halogen, —OH, —$OR''$, —$OC(O)NHR''$, —$OC(O)NR''R^o$, —SH, —$SR''$, —$S(O)R''$, —$S(O)_2R''$, —$SO_2NH_2$, —$S(O)_2NHR''$, —$S(O)_2NR''R^o$, —$NHS(O)_2R''$, —$NR''S(O)_2R^o$, —$NR''S(O)_2R^o$, —$C(O)NH_2$, —$C(O)NHR''$, —$C(O)NR''R^o$, —$C(O)R''$, —$NHC(O)R''$, —$NR''C(O)R^o$, —$NHC(O)NH_2$, —$NR''C(O)NH_2$, —$NR''C(O)NHR^o$, —$NHC(O)NHR''$, —$NR''C(O)NR^oR^p$, —$NHC(O)NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, wherein $R''$, $R^o$ and $R^p$ are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In one preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —$COR^h$, —$CO_2R^h$, —$CONR^hR^h$, —$NR^hCOR^h$, —$SO_2R^h$, —$SO_2NR^hR^i$, —$NSO_2R^hR^i$, —$NR^hR^i$, and —$OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, —OH, —$OR''$, —$OC(O)NHR''$, —$OC(O)NR''R^o$, —SH, —$SR''$, —$S(O)R^o$, —$S(O)_2R''$, —$SO_2NH_2$, —$S(O)_2NHR''$, —$S(O)_2NR''R^o$, —$NHS(O)_2R''$, —$NR''S(O)_2R^o$, —$C(O)NH_2$, —$C(O)NHR''$, —$C(O)NR''R^o$, —$C(O)R''$, —$NHC(O)R''$, —$NR''C(O)R^o$, —$NHC(O)NH_2$, —$NR''C(O)NH_2$, —$NR''C(O)NHR^o$, —$NHC(O)NHR''$, —$NR''C(O)NR^oR^p$, —$NHC(O)NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, wherein $R''$, $R^o$ and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or —O⁻), the resulting group may have either a carbonyl (—C(O)—) or a N-oxide (—N⁺—O⁻).

Suitable substituents for substituted alkyl, substituted alkenyl, and substituted alkynyl include halogen, —CN, —CO₂R', —C(O)R', —C(O)NR'R", oxo (=O or —O⁻), —OR', —OC(O)R', —OC(O)NR'R", —NO₂, —NR'C(O)R", —NR'''C(O)NR'R", —NR'R", —NR'CO₂R", —NR'S(O)R"', —NR'S(O)₂R"', —NR""S(O)NR'R", —NR"'S(O)₂NR'R", —SR', —S(O)R', —S(O)₂R', —S(O)₂NR'R", —NR'—C(NHR")=NR"', —SiR'R"R"', —N₃, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO₂R', —C(O)R', —C(O)NR'R", oxo (=O or —O⁻), —OR', —OC(O)R', —OC(O)NR'R", —NO₂, —NR'C(O)R", —NR'''C(O)NR'R", —NR'R", —NR'CO₂R", —NR'S(O)R"', —NR'S(O)₂R"', —NR""S(O)NR'R", —NR"'S(O)₂NR'R", —SR', —S(O)R', —S(O)₂R', —S(O)₂NR'R", —NR'—C(NHR")=NR"', —SiR'R"R"', —N₃, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10 membered heterocyclyl. The number of possible substituents range from zero to the total number of open valences on the aromatic ring system.

As used above, R', R" and R'" each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R"', or R' and R"' may together with the atom(s) to which they are attached, form a substituted or unsubstituted 5-, 6- or 7-membered ring.

Two of the substituents on adjacent atoms of an aryl or heteroaryl ring may optionally be replaced with a substituent of the formula -T—C(O)—(CH₂)$_q$—U—, wherein T and U are independently —NR""—, —O—, —CH₂— or a single bond, and q is an integer of from 0 to 2. Alternatively, two of the substituents on adjacent atoms of the aryl or heteroaryl ring may optionally be replaced with a substituent of the formula -A'—(CH₂)$_r$—B'—, wherein A' and B' are independently —CH₂—, —O—, —NR""—, —S—, —S(O)—, —S(O)₂—, —S(O)₂NR""— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X—(CH₂)$_t$—, where s and t are independently integers of from 0 to 3, and X is —O—, —NR""—, —S—, —S(O)—, —S(O)₂—, or —S(O)₂NR'—. R"" in is selected from hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs may be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The compounds of the invention may be present in the form of pharmaceutically acceptable metabolites thereof. The term "metabolite" means a pharmaceutically acceptable form of a metabolic derivative of a compound of the invention (or a salt thereof). In some aspects, the metabolite may be a functional derivative of a compound that is readily convertible in vivo into an active compound. In other aspects, the metabolite may be an active compound.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

The compounds of the present invention may include a detectable label. A detectable label is a group that is detectable at low concentrations, usually less than micromolar, possibly less than nanomolar, and that can be readily distinguished from other molecules, due to differences in a molecular property (e.g. molecular weight, mass to charge ratio, radioactivity, redox potential, luminescence, fluorescence, electromagnetic properties, binding properties, and the like). Detectable labels may be detected by spectroscopic, photochemical, biochemical, immunochemical, electrical, magnetic, electromagnetic, optical or chemical means and the like.

A wide variety of detectable labels are within the scope of the present invention, including hapten labels (e.g. biotin, or labels used in conjunction with detectable antibodies such as horse radish peroxidase antibodies); mass tag labels (e.g. stable isotope labels); radioisotopic labels (including $H^3$, $I^{125}$, $S^{35}$, $C^{14}$, or $P^{32}$); metal chelate labels; luminescent labels including fluorescent labels (such as fluorescein, isothiocyanate, Texas red, rhodamine, green fluorescent protein, and the like), phosphorescent labels, and chemiluminescent labels, typically having quantum yield greater than 0.1; electroactive and electron transfer labels; enzyme modulator labels including coenzymes, organometallic catalysts horse radish peroxidase, alkaline phosphatase and others commonly used in an ELISA; photosensitizer labels; magnetic bead labels including Dynabeads; colorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; and carbon black labels. Patents teaching the use of such detectable labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

Detectable labels are commercially available or may be prepared as known to one skilled in the art. Detectable labels may be covalently attached to the compounds using a reactive functional group, which can be located at any appropriate position. Methods for attaching a detectable label are known to one skilled in the art. When the reactive group is attached to an alkyl, or substituted alkyl chain tethered to an aryl nucleus, the reactive group may be located at a terminal position of an alkyl chain.

Compounds

In one embodiment, the compounds of the present invention are represented by formula (I), or salts thereof:

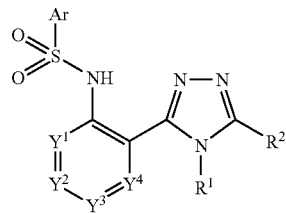

Ar is selected from the group consisting of substituted or unsubstituted $C_{6-10}$ aryl and substituted or unsubstituted 5- to 10-membered heteroaryl.

$Y^1$ is selected from the group consisting of —$CR^{3a}$—, —N—, and —$N^+(O)^-$—;

$Y^2$ is selected from the group consisting of —$CR^{3b}$—, —N—, and —$N^+(O)^-$—;

$Y^3$ is selected from the group consisting of —$CR^{3c}$—, —N—, and —$N^+(O)^-$—;

$Y^4$ is selected from the group consisting of —$CR^{3d}$—, —N—, and —$N^+(O)^-$—;

wherein at least one of $Y^1$, $Y^2$, $Y^3$, or $Y^4$ is —N—.

$R^{3a}$, $R^{3b}$, $R^{3c}$, and $R^{3d}$ are each independently selected from the group consisting of hydrogen, halogen, —CN, —C(O)$R^4$, —CO$_2R^4$, —C(O)NR$^4R^5$, —OR$^4$, —OC(O)$R^4$, —OC(O)NR$^4R^5$, —SR$^4$, —S(O)$R^4$, —S(O)$_2R^4$, —S(O)$_2$NR$^4R^5$, —NO$_2$, —NR$^4R^5$, —NR$^4$C(O)$R^5$, —NR$^4$C(O)OR$^5$, —NR$^4$S(O)$_2R^5$, —NR$^4$C(O)NR$^5R^6$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^4$, $R^5$, and $R^6$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^4$ and $R^5$, $R^5$ and $R^6$ or $R^4$ and $R^6$ may, together with the atoms to which they are attached, form a substituted or unsubstituted 5-, 6-, or 7-membered ring;

$R^1$ is selected from the group consisting of hydrogen, —C(O)$R^7$, —CO$_2R^7$, —C(O)NR$^7R^8$, —S(O)$R^7$, —S(O)$_2R^7$, —S(O)$_2$NR$^7R^8$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^2$ is selected from the group consisting of hydrogen, halogen, —CN, —C(O)$R^7$, —CO$_2R^7$, —C(O)NR$^7R^8$, —OR$^7$, —OC(O)$R^7$, —OC(O)NR$^7R^8$, —SR$^7$, —S(O)$R^7$, —S(O)$_2R^7$, —S(O)$_2$NR$^7R^8$, —NO$_2$, —NR$^7R^8$, —NR$^7$C(O)$R^8$, —NR$^7$C(O)OR$^8$, —NR$^7$S(O)$_2R^8$, —NR$^7$C(O)NR$^8R^9$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^7$, $R^8$, and $R^9$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^7$ and $R^8$, $R^8$ and $R^9$ or $R^7$ and $R^9$ may, together with the atoms to which they are attached, form a substituted or unsubstituted 5-, 6-, or 7-membered ring; and where $R^1$ and $R^2$ may, together with the atoms to which they are attached, form a substituted or unsubstituted 5-, 6-, or 7-membered ring;

with the proviso that N-(1,1-dimethylethyl)-3-[2-[[[3-(5,5-dimethyl-3-octadecyl-2-thiazolidinyl)-4-hydroxyphenyl]sulfonyl]amino]-4-hydroxy-6-methylphenyl]-7-[[4-[ethyl]2-[(methylsulfonyl)amino]ethyl]amino]phenyl]imino]-7H-pyrazolo[5,1-c]-1,2,4-triazole-6-carboxamide is excluded from the scope of formula (I).

In a further embodiment, the compounds are represented by formula (II), or salts thereof:

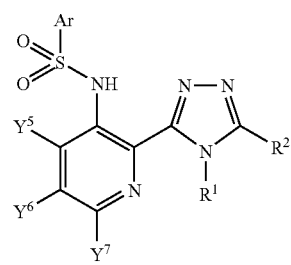

Formula II is an example of Formula I.

Ar, $R^1$ and $R^2$ are as defined above.

$Y^5$, $Y^6$ and $Y^7$ are each independently selected from the group consisting of hydrogen, halogen, —CN, —C(O)$R^{15}$, —CO$_2R^{15}$, —C(O)NR$^{15}R^{16}$, —OR$^{15}$, —OC(O)$R^{15}$, —OC(O)NR$^{15}R^{16}$, —SR$^{15}$, —S(O)$R^{15}$, —S(O)$_2R^{15}$, —S(O)$_2$NR$^{15}R^{16}$, —NO$_2$, —NR$^{15}R^{16}$, —NR$^{15}$C(O)$R^{16}$, —NR$^{15}$C(O)OR$^{16}$, —NR$^{15}$S(O)$_2R^{16}$, —NR$^{15}$C(O)NR$^{16}R^{17}$, substituted or unsubstituted $C_{1-8}$ alkyl, substituted or unsubstituted $C_{2-8}$ alkenyl, substituted or unsubstituted $C_{2-8}$ alkyl, substituted or unsubstituted 3- to 10-membered heterocyclyl, substituted or unsubstituted $C_{6-10}$ alkyl, and substituted or unsubstituted 5- to 10-membered heteroaryl;

$R^{15}$, $R^{16}$ and $R^{17}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{15}$ and $R^{16}$, $R^{16}$ and $R^{17}$ or $R^{15}$ and $R^{17}$ may, together with the atoms to which they are attached, form a substituted or unsubstituted 5-, 6-, or 7-membered ring.

In another embodiment, the compounds are represented by formula (III), or salts thereof:

15

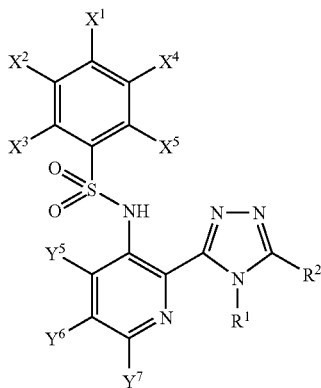

(III)

Formula IV is an example of Formula I.

$R^1$, $R^2$, $Y^5$, $Y^6$ and $Y^7$ are each as defined above.

$X^1$, $X^2$, $X^3$, $X^4$, and $X^5$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)R$^{18}$, —CO$_2$R$^{18}$, —C(O)NR$^{18}$R$^{19}$, —OR$^{18}$, —OC(O)R$^{19}$, —OC(O)NR$^{18}$R$^{19}$, —NO$_2$, —NR$^{18}$C(O)R$^{19}$, —NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —SR$^{18}$, —S(O)R$^{18}$, —S(O)$_2$NR$^{18}$, —S(O)$_2$NR$^{18}$R$^{19}$, substituted or unsubstituted $C_{6-10}$ aryl, substituted or unsubstituted 5- to 10-membered heteroaryl, and substituted or unsubstituted 3- to 10-membered heterocyclyl;

$R^{18}$, $R^{19}$ and $R^{20}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{18}$ and $R^{19}$, $R^{19}$ and $R^{20}$ or $R^{18}$ and $R^{20}$ may, together with the atoms to which they are attached, form a substituted or unsubstituted 5-, 6-, or 7-membered ring.

In one embodiment, the compounds of the present invention are represented by formula (IV), or salts thereof:

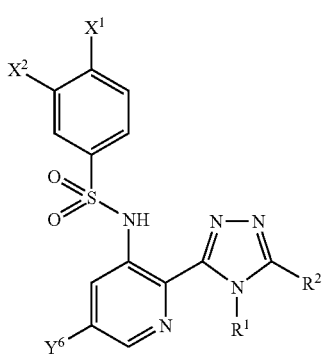

(IV)

wherein $X^1$ and $X^2$ are each independently from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —CO$_2$R$^{18}$, —OR$^{18}$, —OC(O)R$^{19}$, —OC(O)NR$^{18}$R$^{19}$, —NR$^{18}$C(O)R$^{19}$,

16

—NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —NO$_2$, and —SR$^{18}$;

$Y^6$ is selected from the group consisting of halogen, —CN, —OR$^{18}$, and substituted or unsubstituted $C_{1-8}$ alkyl;

$R^1$ is selected from the group consisting of hydrogen, —C(O)R$^7$, —CO$_2$R$^7$, —C(O)NR$^7$R$^8$, —S(O)R$^7$, —S(O)$_2$R$^7$, —S(O)$_2$NR$^7$R$^8$, substituted or unsubstituted $C_{1-8}$ alkyl, $C_{1-8}$ substituted or unsubstituted cycloalkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^2$ is selected from the group consisting of hydrogen, halogen, —CN, —C(O)R$^7$, —CO$_2$R$^7$, —C(O)NR$^7$R$^8$, —OR$^7$, —OC(O)R$^7$, —OC(O)NR$^7$R$^8$, —SR$^7$, —S(O)R$^7$, —S(O)$_2$R$^7$, —S(O)$_2$NR$^7$R$^8$, —NO$_2$, —NR$^7$R$^8$, —NR$^7$C(O)R$^8$, —NR$^7$C(O)OR$^8$, —NR$^7$S(O)$_2$R$^8$, —NR$^7$C(O)NR$^8$R$^9$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

where $R^1$ and $R^2$ may, together with the atoms to which they are attached, form a substituted or unsubstituted 5-, 6-, or 7-membered ring;

$R^7$, $R^8$, and $R^9$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^7$ and $R^8$, $R^8$ and $R^9$ or $R^7$ and $R^9$ may, together with the atoms to which they are attached, form a substituted or unsubstituted 5-, 6-, or 7-membered ring.

$R^{18}$, $R^{19}$ and $R^{20}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{18}$ and $R^{19}$, $R^{19}$ and $R^{20}$ or $R^{1B}$ and $R^{20}$ may, together with the atoms to which they are attached, form a substituted or unsubstituted 5-, 6-, or 7-membered ring;

In another embodiment, the compounds of the present invention are represented by formula (V), or salts thereof:

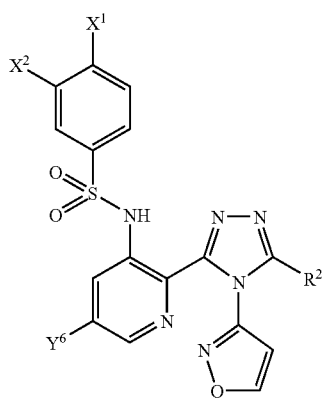

(V)

wherein $X^1$, $X^2$, $Y^6$, and $R^2$ are as defined above for formula (IV).

In another embodiment, the compounds of the present invention are represented by formula (VI), or salts thereof:

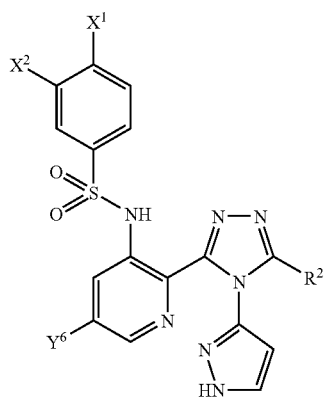

(VI)

wherein $X^1$, $X^2$, $Y^6$, and $R^2$ are as defined above for formula (IV).

In another embodiment, the compounds of the present invention are represented by formula (VII), or salts thereof:

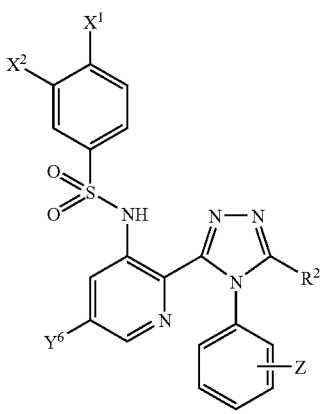

(VII)

wherein $X^1$, $X^2$, $Y^6$, and $R^2$ are as defined above for formula (IV) and Z is 0, 1, 2, 3, 4, or 5 substituents selected from the group consisting of halogen, substituted or unsubstituted $C_{1-8}$ alkyl, and substituted or unsubstituted $C_{1-8}$ alkoxy.

In another embodiment, the compounds of the present invention are represented by formula (VIII), or salts thereof:

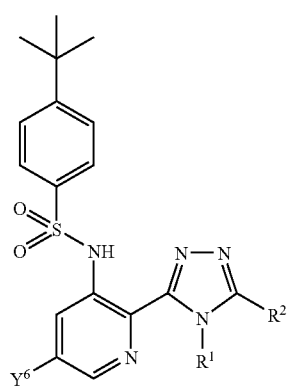

(VIII)

wherein $Y^6$, $R^1$ and $R^2$ are as defined above for formula (I).

In another embodiment, the compounds of the present invention are represented by formula (IX), or salts thereof:

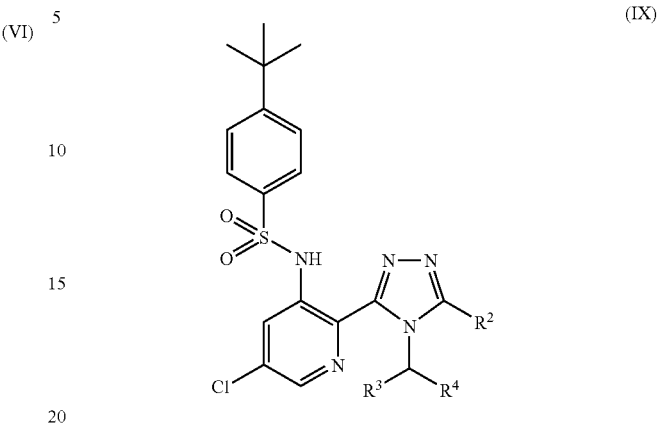

(IX)

where $R^2$ is as defined in formula (IV) and $R^3$ and $R^4$ are each independently hydrogen, unsubstituted or substituted $C_{1-8}$ alkyl, or $R^3$ and $R^4$ together with the carbon which they substitute form a 3-10 membered carboxylic, 4-10 membered heterocyclic or 5-10 membered heteroaryl ring.

Formulae II, III, IV, V, VI, VII, VIII, IX, and XI are examples of Formula I.

Compounds that Modulate CCR2 or CCR9 Activity

The present invention provides compounds that modulate at least one of CCR2 or CCR9 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the invention include, but are not limited to, the exemplary compounds provided herein and salts thereof.

For example, compounds of this invention act as potent CCR2 antagonists, and this antagonistic activity has been further confirmed in animal testing for inflammation, one of the hallmark disease states for CCR2. Accordingly, the compounds provided herein are useful in pharmaceutical compositions, methods for the treatment of CCR2-mediated diseases, and as controls in assays for the identification of competitive CCR2 antagonists.

The compounds of the invention are thought to interfere with inappropriate T-cell trafficking by specifically modulating or inhibiting a chemokine receptor function. Without intending to be bound by any particular theory, it is believed that the compounds provided herein interfere with the interaction between a chemokine receptor and one or more cognate ligands. In particular, it is believed that the compounds interfere with the interaction between CCR9 and a CCR9 ligand, such as TECK. Compounds contemplated by the invention include, but are not limited to, the exemplary compounds provided herein and salts thereof.

For example, compounds of this invention act as potent CCR9 antagonists, and this antagonistic activity has been further confirmed in animal testing for inflammation, one of the hallmark disease states for CCR9. Accordingly, the compounds provided herein are useful in pharmaceutical compositions, methods for the treatment of CCR9-mediated diseases, and as controls in assays for the identification of competitive CCR9 antagonists.

Known Compound

The compound shown below:

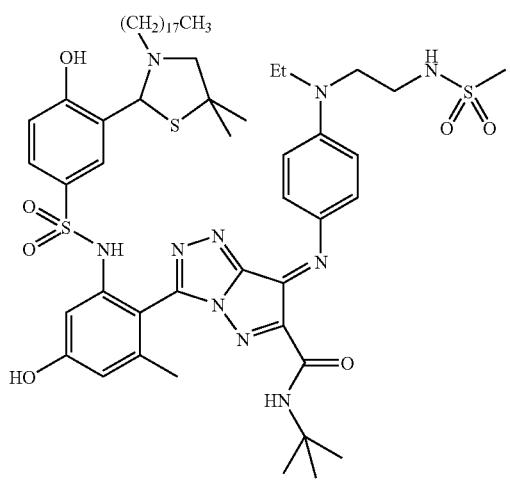

also referred to as N-(1,1-dimethylethyl)-3-[2-[[[3-(5,5-dimethyl-3-octadecyl-2-thiazolidinyl)-4-hydroxyphenyl]sulfonyl]amino]-4-hydroxy-6-methylphenyl]-7-[[4-[ethyl[2-[(methylsulfonyl)amino]ethyl]amino]phenyl]imino]-7H-pyrazolo[5,1-c]-1,2,4-triazole-6-carboxamide, is known, but not as a CCR9 or CCR2 antagonist.

PREFERRED EMBODIMENTS

In the following descriptions and embodiments, references to specific substituents only correspond to formula numbers in which those specific substituents are present or appear.

In one embodiment of formula I, $Y^4$ is —N—.

Preferred Ar Groups

In one embodiment of any the formula I, Ar is selected from the group consisting of substituted or unsubstituted $C_{6-10}$ aryl and substituted or unsubstituted 5- to 10-membered heteroaryl.

In one embodiment of any the formula I, Ar is a $C_{6-10}$ aryl with at least 2 substituents other than hydrogen.

In one embodiment of any the formula I, Ar is a substituted or unsubstituted bicyclic aryl or substituted or unsubstituted bicyclic heteroaryl.

In one embodiment of any the formula a, Ar is selected from the group consisting of:

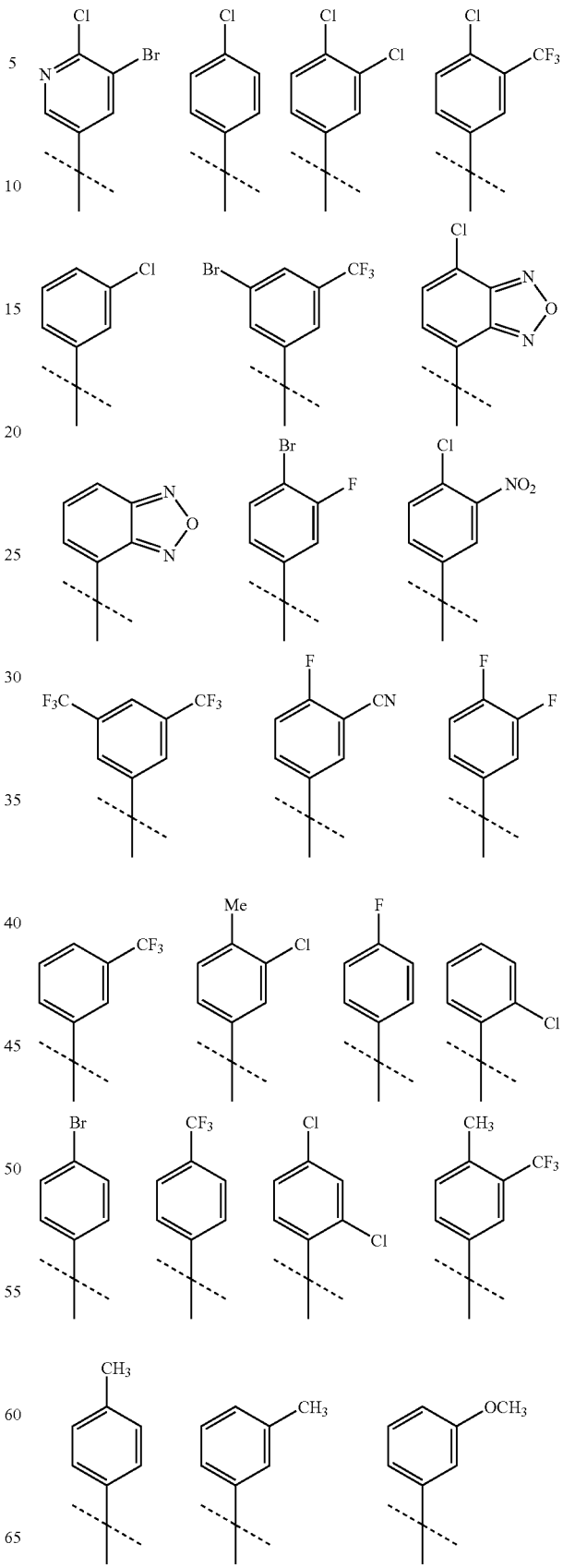

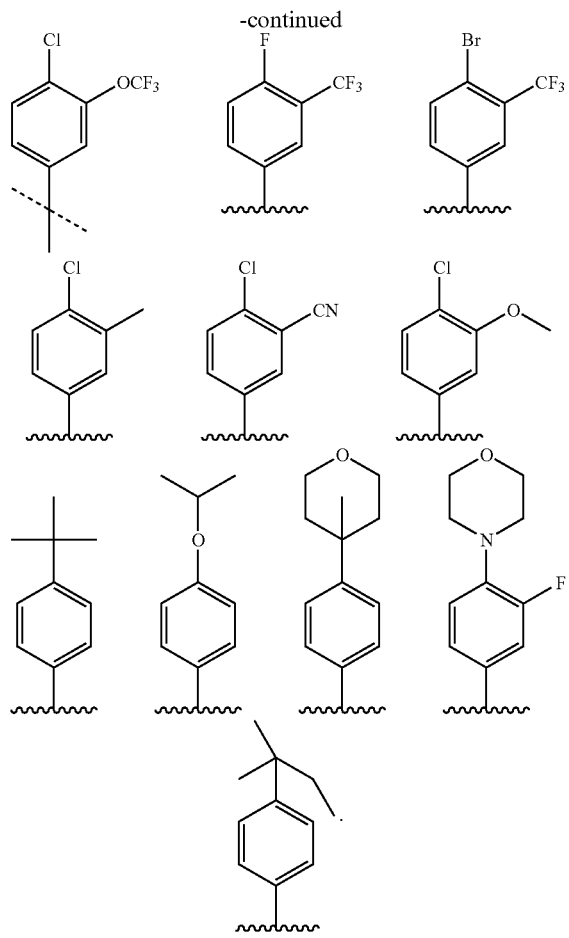

In one embodiment of formulae (I or II), Ar is substituted phenyl.

Preferred X Groups

In one embodiment of formulae (III, IV, V, VI, VII, or XI), both $X^1$ and $X^2$ are selected from the group consisting of halogen, —CN, and —CF$_3$.

In one embodiment of formulae (III, IV, V, VI, VII, or XI), one of $X^1$ and $X^2$ is halogen and one of $X^1$ and $X^2$ is selected from the group consisting of halogen, —CN, and —CF$_3$.

In one embodiment of formulae (III, IV, V, VI, VII, or XI), $X^1$ is chloro.

In one embodiment of formulae (III, IV, V, VI, VII, or XI), $X^1$ is methyl.

In one embodiment of formulae (III, IV, V, VI, VII, or XI), $X^1$ is selected from the group consisting of substituted $C_{1-8}$ alkyl or unsubstituted $C_{2-8}$ alkyl, substituted or unsubstituted $C_{2-8}$ alkenyl, and substituted or unsubstituted $C_{2-8}$ alkynyl.

In one embodiment of formulae (III, IV, V, VI, VII, or XI), $X^1$ is an unsubstituted $C_{2-8}$ alkyl.

In one embodiment of formulae (III, IV, V, VI, VII or XI), $X^1$ is other than methyl.

In one embodiment of formulae (III, IV, V, VI, VII, or XI), $X^1$ is t-butyl.

In one embodiment of formulae (III, IV, V, VI, VII, or XI), $X^1$ is isopropoxy.

In one embodiment of formulae (III, IV, V, VI, VII, or XII), $X^1$ is morpholine.

In one embodiment of formulae (III, IV, V, VI, VII, or XI), $X^2$ is —CF$_3$.

In one embodiment of formulae (III, IV, V, VI, VII, or XI), $X^2$ is chloro.

In one embodiment of formulae (III, IV, V, VI, VII, or XI), $X^2$ is fluoro.

In one embodiment of formulae (III, IV, V, VI, VII, or XI), $X^1$ is chloro and $X^2$ is —CF$_3$.

In one embodiment of formulae (III, IV, V, VI, VII, or XI), $X^1$ is chloro and $X^2$ is chloro.

In one embodiment of formulae (III, IV, V, VI, VII, or XI), $X^1$ is methyl and $X^2$ is —CF$_3$.

In one embodiment of formulae (III, IV, V, VI, VII, or XI), $X^1$ is morpholine and $X^2$ is fluoro.

Preferred Y Groups

In one embodiment of any of formulae (II and III) $Y^5$, $Y^6$, and $Y^7$ are each independently selected from the group consisting of hydrogen, fluorine, chlorine, and bromine, where one of $Y^5$, $Y^6$, and $Y^7$ is other than hydrogen.

In another embodiment of any of formulae (II and III), at least one of $Y^5$, $Y^6$, and $Y^7$ is other than hydrogen; preferably $Y^6$ is halogen.

In another embodiment of any of formulae (II and III), at least one of $Y^5$, $Y^6$, and $Y^7$ is other than hydrogen; preferably $Y^6$ is halogen.

In another embodiment of any of formulae (II and III), $Y^5$ and $Y^7$ are hydrogen and $Y^6$ is halogen.

In another embodiment of any of formulae (II and III), $Y^5$ and $Y^7$ are hydrogen and $Y^6$ is chloro.

In one embodiment of any of formulae (II and III), $Y^5$ and $Y^7$ are hydrogen, and $Y^6$ is —CH$_3$.

In one embodiment of any of formulae (II, III, IV, V, VI, VII, VIII, and XI), $Y^6$ is selected from the group consisting of halogen, —CN, —OR$^{15}$, and substituted or unsubstituted $C_{1-8}$ alkyl.

In one embodiment of any of (II, III, IV, V, VI, VII, VIII, and XI), $Y^6$ is selected from the group consisting of —Cl, —Br, —F, —OCH$_3$, —CH$_3$, —CF$_3$, and —CN In one embodiment of any of formulae (II, III, IV, V, VI, VII, VIII, and XI), $Y^6$ is selected from the group consisting of —Cl, —Br, —F, and —OCH$_3$.

In one embodiment of any of formulae (II, III, IV, V, VI, VII, VIII, and XI), $Y^6$ is halogen.

In one embodiment of any of formulae (II, III, IV, V, VI, VII, VIII, and XI), $Y^6$ is bromine.

In one embodiment of any of formulae (II, III, IV, V, VI, VII, VIII, and XI), $Y^6$ is chloro.

Preferred $R^1$ and $R^2$ Groups

In one embodiment of formulae (I, II, III, IV, or VIII), $R^1$ is other than hydrogen.

In one embodiment of formulae (I, II, III, IV, or VII), $R^1$ is selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl.

In one embodiment of formulae (I, II, III, IV, or VIII), $R^1$ is selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted 5- to 6-membered heterocyclyl, substituted or unsubstituted phenyl, and substituted or unsubstituted 5- to 6-membered heteroaryl.

In one embodiment of formulae (I, II, III, IV, or VII), $R^1$ is substituted or unsubstituted $C_{1-8}$ alkyl.

In one embodiment of formulae (I, II, III, IV, or VIII), $R^1$ is substituted or unsubstituted phenyl.

In one embodiment of formulae (I, II, III, IV, or VIII), $R^1$ is methyl.

In one embodiment of formulae (I, II, III, IV, or VIII), $R^1$ is ethyl.

In one embodiment of formulae (I, II, III, IV, or VII), $R^1$ is isopropyl.

In one embodiment of formulae (I, II, III, IV, or VIII), $R^1$ is substituted or unsubstituted 5- to 6-membered heteroaryl.

In one embodiment of formulae (I, II, III, IV, or VIII), $R^1$ is substituted or unsubstituted 5- to 6-membered heterocyclyl.

In one embodiment of formulae (I, II, III, IV, or VIII), $R^1$ is methyl, ethyl or isopropyl.

In one embodiment of formulae (I, II, III, IV, or VIII), $R^1$ is selected from the group consisting of unsubstituted or substituted phenyl, unsubstituted or substituted pyridyl, and unsubstituted or substituted pyrazolyl.

In one embodiment of formulae (I, II, III, IV, or VIII) $R^1$ is substituted or unsubstituted oxazole.

In one embodiment of formulae (I, II, III, IV, or VIII), $R^1$ is substituted or unsubstituted pyrrolidinyl.

In one embodiment of formulae (I, II, III, IV, or VIII), $R^1$ is substituted or unsubstituted piperidinyl.

In one embodiment of formulae (I, II, III IV, or VIII), $R^1$ is one member of the group consisting of:

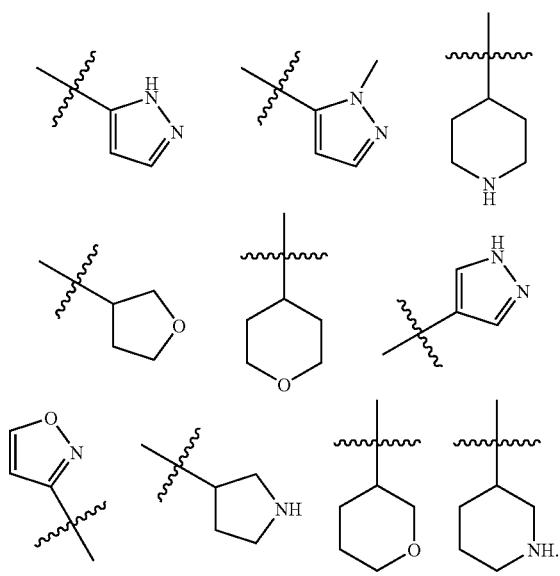

In one embodiment of formulae (I, II, III, IV, V, VI, VII, VIII, IX, or XI), $R^2$ is other than hydrogen.

In one embodiment of formulae (I, II, III, IV, V, VI, VII, VIII, IX, or XI), $R^2$ is hydrogen.

In one embodiment of formulae (I, II, III, IV, V, VI, VII, VIII, IX, or XI), $R^2$ is methyl In one embodiment of formulae (I, II, III, IV, V, VI, VII, VIII, IX, or XI, $R^2$ is ethyl.

In one embodiment of formulae (I, II, III, IV, V, VI, VII, VIII, IX, or XI), $R^2$ is isopropyl.

In one embodiment of formulae (I, II, III, IV, V, VI, VII, VIII, IX, or XI), $R^2$ is selected from the group consisting of halogen, —CN, —C(O)$R^7$, —CO$_2R^7$, —C(O)NR$^7R^8$, —O$R^7$, —OC(O)$R^7$, —OC(O)NR$^7R^8$, —S$R^7$, —S(O)$R^7$, —S(O)$_2R^7$, —S(O)$_2$NR$^7R^8$, —NO$_2$, —NR$^7R^8$, —NR$^7$C(O)R$^8$, —NR$^7$C(O)OR$^8$, —NR$^7$S(O)$_2R^8$, and —NR$^7$C(O)NR$^8R^9$.

In one embodiment of formulae (I, II, III, IV, V, VI, VII, VIII, IX, or XI), $R^2$ is selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl.

In one embodiment of formulae (I, II, III, IV, V, VI, VII, VIII, IX, or XI), $R^2$ is selected from the group consisting of substituted or unsubstituted 5- to 6-membered heterocyclyl, substituted or unsubstituted phenyl, and substituted or unsubstituted 5- to 6-membered heteroaryl.

In one embodiment of formulae (I, II, III, IV, V, VI, VII, VIII, IX, or XI), $R^2$ is substituted or unsubstituted $C_{1-8}$ alkyl.

In one embodiment of formulae (I, II, III, IV, V, VI, VII, VIII, IX, or XI), $R^2$ is substituted or unsubstituted 5- to 6-membered heterocyclyl.

In one embodiment of formulae (I, II, III, IV, V, VI, VII, VIII, IX, or XI), $R^2$ is substituted or unsubstituted 5-to-6-membered heteroaryl.

In one embodiment of formulae (I, II, III, IV, V, VI, VII, VIII, IX, or XI), $R^2$ is methyl.

Preferred $R^3$ and $R^4$ Groups

In one embodiment of formula (IX), $R^3$ and $R^4$ are each hydrogen.

In one embodiment of formula (IX), one of $R^3$ and $R^4$ is hydrogen and the other is unsubstituted or substituted $C_{1-8}$ alkyl.

In one embodiment of formula (IX), both of $R^3$ and $R^4$ are unsubstituted or substituted $C_{1-8}$ alkyl.

In one embodiment of formula (IX), $R^3$ and $R^4$ together with the carbon which they substitute form a 3-10 membered carboxylic ring.

In one embodiment of formula (IX), $R^3$ and $R^4$ together with the carbon which they substitute form a 4-10 membered heterocyclic ring.

In one embodiment of formula (IX), $R^3$ and $R^4$ together with the carbon which they substitute form a 5-10 membered heteroaryl ring.

Exemplary Compounds

The following compounds are within the scope of the formula (I):

tert-butyl 3-(3-(3-(4-tert-butylphenylsulfonamido)-5-methylpyridin-2-yl)-4H-1,2,4-triazol-4-yl)pyrrolidine-1-carboxylate;

ethyl 5-(3-(4-tert-butylphenylsulfonamido)-5-chloropyridin-2-yl)-4-isopropyl-4H-1,2,4-triazole-3-carboxylate;

5-(3-(4-tert-butylphenylsulfonamido)-5-chloropyridin-2-yl)-4-isopropyl-N,N-dimethyl-4H-1,2,4-triazole-3-carboxamide;

5-(3-(4-tert-butylphenylsulfonamido)-5-chloropyridin-2-yl)-4-isopropyl-N-methyl-4H-1,2,4-triazole-3-carboxamide;

N-(5-(3-(4-tert-butylphenylsulfonamido)-5-chloropyridin-2-yl)-4-isopropyl-4H-1,2,4-triazol-3-yl)acetamide;

(S)-4-tert-butyl-N-(5-chloro-2-(4-(piperidin-3-yl)-4H-1,2,4-triazol-3-yl)pyridin-3-yl)benzenesulfonamide;

(S)-4-tert-butyl-N-(5-chloro-2-(4-(pyrrolidin-3-yl)-4H-1,2,4-triazol-3-yl)pyridin-3-yl)benzenesulfonamide;

(S)-4-tert-butyl-N-(5-chloro-2-(4-methyl-5-(pyrrolidin-2-yl)-4H-1,2,4-triazol-3-yl)pyridin-3-yl)benzenesulfonamide;

4-tert-butyl-N-(5-chloro-2-(4,5-dimethyl-4H-1,2,4-triazol-3-yl)pyridin-3-yl)benzenesulfonamide;

4-tert-butyl-N-(5-chloro-2-(4-(2-fluorophenyl)-4H-1,2,4-triazol-3-yl)pyridin-3-yl)benzenesulfonamide;

4-tert-butyl-N-(5-chloro-2-(4-cyclopropyl-5-methyl-4H-1,2,4-triazol-3-yl)pyridin-3-yl)benzenesulfonamide;
4-tert-butyl-N-(5-chloro-2-(4-ethyl-4H-1,2,4-triazol-3-yl)pyridin-3-yl)benzenesulfonamide;
4-tert-butyl-N-(5-chloro-2-(4-ethyl-5-(methoxymethyl)-4H-1,2,4-triazol-3-yl)pyridin-3-yl)benzenesulfonamide;
4-tert-butyl-N-(5-chloro-2-(4-ethyl-5-methyl-4H-1,2,4-triazol-3-yl)pyridin-3-yl)benzenesulfonamide;
4-tert-butyl-N-(5-chloro-2-(4-isopropyl-4H-1,2,4-triazol-3-yl)pyridin-3-yl)benzenesulfonamide;
4-tert-butyl-N-(5-chloro-2-(4-isopropyl-5-(methoxymethyl)-4H-1,2,4-triazol-3-yl)pyridin-3-yl)benzenesulfonamide;
4-tert-butyl-N-(5-chloro-2-(4-isopropyl-5-methyl-4H-1,2,4-triazol-3-yl)pyridin-3-yl)benzenesulfonamide;
4-tert-butyl-N-(5-chloro-2-(4-methyl-4H-1,2,4-triazol-3-yl)pyridin-3-yl)benzenesulfonamide;
4-tert-butyl-N-(5-chloro-2-(4-methyl-5-(piperidin-4-yl)-4H-1,2,4-triazol-3-yl)pyridin-3-yl)benzenesulfonamide;
4-tert-butyl-N-(5-chloro-2-(4-methyl-5-(pyridin-3-yl)-4H-1,2,4-triazol-3-yl)pyridin-3-yl)benzenesulfonamide;
4-tert-butyl-N-(5-chloro-2-(4-methyl-5-(pyridin-4-yl)-4H-1,2,4-triazol-3-yl)pyridin-3-yl)benzenesulfonamide;
4-tert-butyl-N-(5-chloro-2-(4-phenyl-4H-1,2,4-triazol-3-yl)pyridin-3-yl)benzenesulfonamide;
4-tert-butyl-N-(5-chloro-2-(5,6,7,8-tetrahydro-[1,2,4]triazolo[4,3-a]pyrazin-3-yl)pyridin-3-yl)benzenesulfonamide;
4-tert-butyl-N-(5-chloro-2-(5-(2-hydroxypropan-2-yl)-4-isopropyl-4H-1,2,4-triazol-3-yl)pyridin-3-yl)benzenesulfonamide;
4-tert-butyl-N-(5-chloro-2-(5-(isoxazol-5-yl)-4-methyl-4H-1,2,4-triazol-3-yl)pyridin-3-yl)benzenesulfonamide;
4-tert-butyl-N-(5-chloro-2-(5-(methoxymethyl)-4-(tetrahydro-2H-pyran-4-yl)-4H-1,2,4-triazol-3-yl)pyridin-3-yl)benzenesulfonamide;
4-tert-butyl-N-(5-chloro-2-(5-(methoxymethyl)-4-methyl-4H-1,2,4-triazol-3-yl)pyridin-3-yl)benzenesulfonamide;
4-tert-butyl-N-(5-chloro-2-(5-isopropyl-4-methyl-4H-1,2,4-triazol-3-yl)pyridin-3-yl)benzenesulfonamide;
4-tert-butyl-N-(5-chloro-2-(6,8-dihydro-5H-[1,2,4]triazolo[3,4-c][1,4]oxazin-3-yl)pyridin-3-yl)benzenesulfonamide;
4-tert-butyl-N-(5-methyl-2-(4-(1-methylpyrrolidin-3-yl)-4H-1,2,4-triazol-3-yl)pyridin-3-yl)benzenesulfonamide;
4-tert-butyl-N-(5-methyl-2-(4-(pyrrolidin-3-yl)-4H-1,2,4-triazol-3-yl)pyridin-3-yl)benzenesulfonamide;
N-(2-(5-amino-4-isopropyl-4H-1,2,4-triazol-3-yl)-5-chloropyridin-3-yl)-4-tert-butylbenzenesulfonamide;
ethyl 5-(5-chloro-3-(4-chloro-3-(trifluoromethyl)phenylsulfonamido)pyridin-2-yl)-4-(isoxazol-3-yl)-4H-1,2,4-triazole-3-carboxylate;
ethyl 5-(5-chloro-3-(4-chloro-3-(trifluoromethyl)phenylsulfonamido)pyridin-2-yl)-4-isopropyl-4H-1,2,4-triazole-3-carboxylate;
5-(3-(4-chloro-3-(trifluoromethyl)phenylsulfonamido)-5-methylpyridin-2-yl)-4-(isoxazol-3-yl)-4H-1,2,4-triazole-3-carboxamide;
5-(3-(4-chloro-3-(trifluoromethyl)phenylsulfonamido)-5-methylpyridin-2-yl)-4-phenyl-4H-1,2,4-triazole-3-carboxamide;
5-(5-chloro-3-(3,4-dichlorophenylsulfonamido)pyridin-2-yl)-4-(isoxazol-3-yl)-4H-1,2,4-triazole-3-carboxamide;
5-(5-chloro-3-(4-chloro-3-(trifluoromethyl)-phenylsulfonamido)pyridin-2-yl)-4-(isoxazol-3-yl)-4H-1,2,4-triazole-3-carboxamide;
5-(5-chloro-3-(4-chloro-3-(trifluoromethyl)phenylsulfonamido)pyridin-2-yl)-4-(isoxazol-3-yl)-N,N-dimethyl-4H-1,2,4-triazole-3-carboxamide;
5-(5-chloro-3-(4-chloro-3-(trifluoromethyl)phenylsulfonamido)pyridin-2-yl)-4-isopropyl-4H-1,2,4-triazole-3-carboxamide;
5-(5-chloro-3-(4-chloro-3-(trifluoromethyl)phenylsulfonamido)pyridin-2-yl)-4-isopropyl-N,N-dimethyl-4H-1,2,4-triazole-3-carboxamide;
5-(5-chloro-3-(4-chloro-3-(trifluoromethyl)phenylsulfonamido)pyridin-2-yl)-N-ethyl-4-(isoxazol-3-yl)-4H-1,2,4-triazole-3-carboxamide;
5-(5-chloro-3-(4-chloro-3-(trifluoromethyl)phenylsulfonamido)pyridin-2-yl)-N-ethyl-4-(isoxazol-3-yl)-N-methyl-4H-1,2,4-triazole-3-carboxamide;
5-(5-chloro-3-(4-chloro-3-(trifluoromethyl)phenylsulfonamido)pyridin-2-yl)-N-isopropyl-4-(isoxazol-3-yl)-4H-1,2,4-triazole-3-carboxamide;
5-(5-chloro-3-(4-methyl-3-(trifluoromethyl)phenylsulfonamido)pyridin-2-yl)-4-(isoxazol-3-yl)-4H-1,2,4-triazole-3-carboxamide;
(S)-4-chloro-N-(5-chloro-2-(4-(1-hydroxypropan-2-yl)-4H-1,2,4-triazol-3-yl)pyridin-3-yl)-3-(trifluoromethyl)benzenesulfonamide;
3,4-dichloro-N-(5-chloro-2-(4-(isoxazol-3-yl)-4H-1,2,4-triazol-3-yl)pyridin-3-yl)benzenesulfonamide;
4-chloro-N-(5-chloro-2-(4-((3S,4S)-4-methoxypyrrolidin-3-yl)-4H-1,2,4-triazol-3-yl)pyridin-3-yl)-3-(trifluoromethyl)benzenesulfonamide;
4-chloro-N-(5-chloro-2-(4-(1-(dimethylamino)propan-2-yl)-4H-1,2,4-triazol-3-yl)pyridin-3-yl)-3-(trifluoromethyl)benzenesulfonamide;
4-chloro-N-(5-chloro-2-(4-(1-methyl-1H-pyrazol-5-yl)-4H-1,2,4-triazol-3-yl)pyridin-3-yl)-3-(trifluoromethyl)benzenesulfonamide;
4-chloro-N-(5-chloro-2-(4-(3-methyl-1H-pyrazol-4-yl)-4H-1,2,4-triazol-3-yl)pyridin-3-yl)-3-(trifluoromethyl)benzenesulfonamide;
4-chloro-N-(5-chloro-2-(4-(4-hydroxybutan-2-yl)-4H-1,2,4-triazol-3-yl)pyridin-3-yl)-3-(trifluoromethyl)benzenesulfonamide;
4-chloro-N-(5-chloro-2-(4-(4-methyl-1H-pyrazol-3-yl)-4H-1,2,4-triazol-3-yl)pyridin-3-yl)-3-(trifluoromethyl)benzenesulfonamide;
4-chloro-N-(5-chloro-2-(5-(4-(5-fluoro-2-methoxyphenyl)-4H-1,2,4-triazol-3-yl)pyridin-3-yl)-3-(trifluoromethyl)benzenesulfonamide;
4-chloro-N-(5-chloro-2-(4-(isoxazol-3-yl)-5-(methoxymethyl)-4H-1,2,4-triazol-3-yl)pyridin-3-yl)-3-(trifluoromethyl)benzenesulfonamide;
4-chloro-N-(5-chloro-2-(4-(isoxazol-3-yl)-5-(morpholine-4-carbonyl)-4H-1,2,4-triazol-3-yl)pyridin-3-yl)-3-(trifluoromethyl)benzenesulfonamide;
4-chloro-N-(5-chloro-2-(4-(isoxazol-3-yl)-5-(pyrrolidine-1-carbonyl)-4H-1,2,4-triazol-3-yl)pyridin-3-yl)-3-(trifluoromethyl)benzenesulfonamide;
4-chloro-(5-chloro-2-(4-(piperidin-4-yl)-4H-1,2,4-triazol-3-yl)pyridin-3-yl)-3-(trifluoromethyl)benzenesulfonamide;
4-chloro-N-(5-chloro-2-(4-(pyrrolidin-3-yl)-4H-1,2,4-triazol-3-yl)pyridin-3-yl)-3-(trifluoromethyl)benzenesulfonamide;
4-chloro-N-(5-chloro-2-(4-o-tolyl-4H-1,2,4-triazol-3-yl)pyridin-3-yl)-3-(trifluoromethyl)benzenesulfonamide;
4-chloro-N-(5-chloro-2-(4-phenyl-5-(trifluoromethyl)-4H-1,2,4-triazol-3-yl)pyridin-3-yl)-3-(trifluoromethyl)benzenesulfonamide;

4-chloro-N-(5-chloro-2-(4-propyl-4H-1,2,4-triazol-3-yl)pyridin-3-yl)-3-(trifluoromethyl)benzenesulfonamide;
4-chloro-N-(5-chloro-2-(5-((dimethylamino)methyl)-4-isopropyl-4H-1,2,4-triazol-3-yl)pyridin-3-yl)-3-(trifluoromethyl)benzenesulfonamide;
4-chloro-N-(5-chloro-2-(5-(hydroxymethyl)-4-(isoxazol-3-yl)-4H-1,2,4-triazol-3-yl)pyridin-3-yl)-3-(trifluoromethyl)benzenesulfonamide;
4-chloro-N-(5-chloro-2-(5-(hydroxymethyl)-4-isopropyl-4H-1,2,4-triazol-3-yl)pyridin-3-yl)-3-(trifluoromethyl) benzenesulfonamide;
4-chloro-N-(5-chloro-2-(5-(methoxymethyl)-4-(1H-pyrazol-3-yl)-4H-1,2,4-triazol-3-yl)pyridin-3-yl)-3-(trifluoromethyl)benzenesulfonamide;
4-chloro-N-(5-chloro-2-(5-chloro-4-isopropyl-4H-1,2,4-triazol-3-yl)pyridin-3-yl)-3-(trifluoromethyl)benzenesulfonamide;
4-chloro-N-(5-chloro-2-(5-cyclopropyl-4-(1H-pyrazol-3-yl)-4H-1,2,4-triazol-3-yl)pyridin-3-yl)-3-(trifluoromethyl)benzenesulfonamide;
4-chloro-N-(5-chloro-2-(5-isopropyl-4-(1H-pyrazol-3-yl)-4H-1,2,4-triazol-3-yl)pyridin-3-yl)-3-(trifluoromethyl) benzenesulfonamide;
N-(2-(4-(1H-pyrazol-3-yl)-4H-1,2,4-triazol-3-yl)-5-bromopyridin-3-yl)-4-chloro-3-(trifluoromethyl)benzenesulfonamide;
N-(2-(4-(1H-pyrazol-3-yl)-4H-1,2,4-triazol-3-yl)-5-chloropyridin-3-yl)-3,4-dichlorobenzenesulfonamide;
N-(2-(4-(1H-pyrazol-3-yl)-4H-1,2,4-triazol-3-yl)-5-methylpyridin-3-yl)-4-chloro-3-(trifluoromethyl)benzenesulfonamide;
N-(2-(4-(1H-pyrazol-3-yl)-5-(trifluoromethyl)-4H-1,2,4-triazol-3-yl)-5-chloropyridin-3-yl)-4-chloro-3-(trifluoromethyl)benzenesulfonamide;
N-(2-(4-(1H-pyrazol-4-yl)-4H-1,2,4-triazol-3-yl)-5-chloropyridin-3-yl)-4-chloro-3-(trifluoromethyl)benzenesulfonamide;
N-(2-(4-(4-bromo-1H-pyrazol-3-yl)-4H-1,2,4-triazol-3-yl)-5-chloropyridin-3-yl)-3,4-dichlorobenzenesulfonamide;
N-(2-(4-(4-bromo-1H-pyrazol-3-yl)-4H-1,2,4-triazol-3-yl)-5-chloropyridin-3-yl)-4-chloro-3-(trifluoromethyl)benzenesulfonamide;
N-(2-(4-(4-bromo-1H-pyrazol-3-yl)-5-methyl-4H-1,2,4-triazol-3-yl)-5-chloropyridin-3-yl)-4-chloro-3-(trifluoromethyl)benzenesulfonamide;
N-(2-(5-tert-butyl-4-(1H-pyrazol-3-yl)-4H-1,2,4-triazol-3-yl)-5-chloropyridin-3-yl)-4-chloro-3-(trifluoromethyl) benzenesulfonamide;
N-(2-(5-amino-4-isopropyl-4H-1,2,4-triazol-3-yl)-5-chloropyridin-3-yl)-4-chloro-3-(trifluoromethyl)benzenesulfonamide;
N-(2-(5-bromo-4-(4-bromo-1H-pyrazol-3-yl)-4H-1,2,4-triazol-3-yl)-5-chloropyridin-3-yl)-3,4-dichlorobenzenesulfonamide;
N-(2-(5-bromo-4-(isoxazol-3-yl)-4H-1,2,4-triazol-3-yl)-5-chloropyridin-3-yl)-4-chloro-3-(trifluoromethyl)benzenesulfonamide;
N-(2-(5-bromo-4-isopropyl-4H-1,2,4-triazol-3-yl)-5-chloropyridin-3-yl)-4-chloro-3-(trifluoromethyl)benzenesulfonamide; and
N-(5-bromo-2-(4-(isoxazol-3-yl)-4H-1,2,4-triazol-3-yl)pyridin-3-yl)-4-chloro-3-(trifluoromethyl)benzenesulfonamide.

Compositions that Modulate Chemokine Activity

In another aspect, the present invention provides compositions that modulate chemokine activity, specifically CCR2 activity or CCR9 activity. Generally, the compositions for modulating chemokine receptor activity in humans and animals will comprise a pharmaceutically acceptable excipient or diluent and a compound having the formula provided above as formula (I).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166, 452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

In one embodiment, the present invention provides a composition consisting of a pharmaceutically acceptable carrier and a compound of the invention.

Methods of Treatment

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, wherein a compound or composition of the invention is administered either alone or in combination with a second therapeutic agent, wherein said second therapeutic agent is an antihistamine, When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present invention may be used in conjunction with an anti-inflammatory or analgesic agent such as an opiate agonists a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a β2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating or Preventing CCR2-mediated Conditions or Diseases

In yet another aspect, the present invention provides methods of treating or preventing a CCR2-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. For example, compounds for use in treating or preventing a CCR2-mediated condition or disease may include compounds of the formula (I) wherein Ar is selected from the group consisting of:

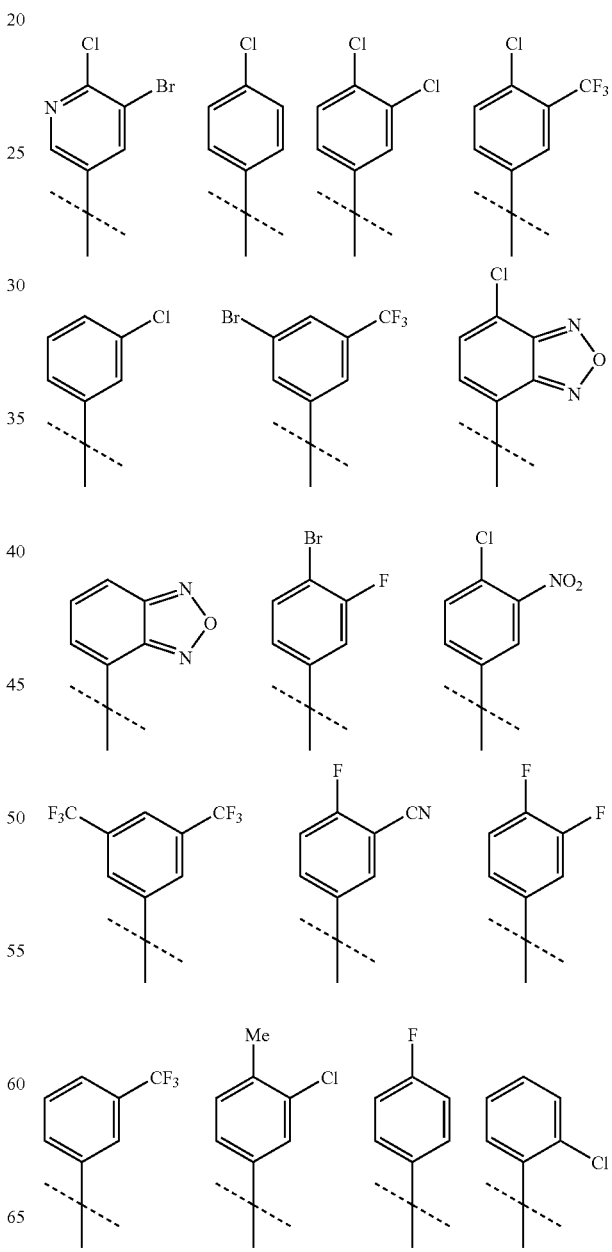

-continued

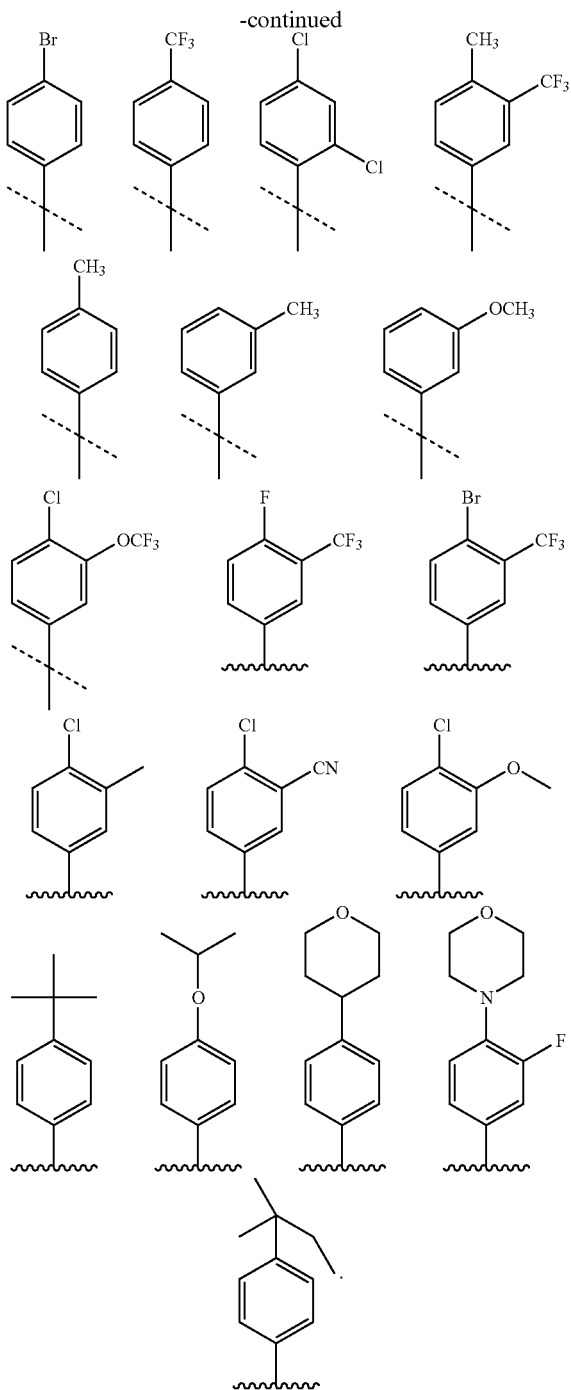

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR2-mediated condition or disease" and related phrases and terms refer to a condition or disease characterized by inappropriate, i.e., less than or greater than normal, CCR2 functional activity. Inappropriate CCR2 functional activity might arise as the result of CCR2 expression in cells which normally do not express CCR2, increased CCR2 expression (leading to, e.g., inflammatory and immunoregulatory disorders and diseases) or decreased CCR2 expression. Inappropriate CCR2 functional activity might also arise as the result of MCP-1 secretion by cells which normally do not secrete MCP-1, increased MCP-1 expression (leading to, e.g., inflammatory and immunoregulatory disorders and diseases) or decreased MCP-1 expression. A CCR2-mediated condition or disease may be completely or partially mediated by inappropriate CCR2 functional activity. However, a CCR2-mediated condition or disease is one in which modulation of CCR2 results in some effect on the underlying condition or disease (e.g. a CCR2 antagonist results in some improvement in patient well being in at least some patients). Furthermore, MCP-2, 3 and 4 are also CCR2 ligands.

In one embodiment, the present invention provides a method of treating a CCR2-mediated condition or disease involving administering to a subject a safe and effective amount of the compound or composition of the invention.

In one embodiment, the present invention provides a method of treating a CCR2-mediated condition or disease involving administering to a subject a sale and effective amount of the compound or composition of the invention, where the CCR2-mediated condition or disease is atherosclerosis.

In one embodiment, the present invention provides a method of treating a CCR2-mediated condition or disease involving administering to a subject a sate and effective amount of the compound or composition of the invention, where the CCR2-mediated condition or disease is restenosis.

In one embodiment, the present invention provides a method of treating a CCR2-mediated condition or disease involving administering to a subject a safe and effective amount of the compound or composition of the invention, where the CCR2-mediated condition or disease is multiple sclerosis.

In one embodiment, the present invention provides a method of treating a CCR2-mediated condition or disease involving administering to a subject a safe and effective amount of the compound or composition of the invention, where the CCR2-mediated condition or disease is selected from the group consisting of inflammatory bowel disease, renal fibrosis, rheumatoid arthritis, obesity and non-insulin-dependent diabetes.

In one embodiment, the present invention provides a method of treating a CCR2-mediated condition or disease involving administering to a subject a safe and effective amount of the compound or composition of the invention, where the CCR2-mediated condition or disease is type 2 diabetes.

In one embodiment, the present invention provides a method of treating a CCR2-mediated condition or disease involving administering to a subject a safe and effective amount of the compound or composition of the invention, where the CCR2-mediated condition or disease is selected from the group consisting of chronic obstructive pulmonary disease, idiopathic pulmonary fibrosis and idiopathic pneumonia syndrome.

In one embodiment, the present invention provides a method of treating a CCR2-mediated condition or disease involving administering to a subject a safe and effective amount of the compound or composition of the invention, where the administering is oral, parenteral, rectal, transdermal, sublingual, nasal or topical In one embodiment, the present invention provides a method of treating a CCR2-mediated condition or disease involving administering to a subject a safe and effective amount of the compound or composition of the invention, where the compound is administered in combination with an anti-inflammatory or analgesic agent.

In one embodiment, the present invention provides a method of treating a CCR2-mediated condition or disease involving administering to a subject a safe and effective amount of the compound or composition of the invention, where an anti-inflammatory or analgesic agent is also administered.

In one embodiment, the present invention provides a method of modulating CCR2 function in a cell, where the CCR2 function in the cell is modulated by contacting the cell with a CCR2 modulating amount of the compound of the present invention.

In one embodiment, the present invention provides a method of treating a CCR2-mediated condition or disease involving administering to a subject a safe and effective amount of the compound or composition of the invention, where the disease is selected from the group consisting of pulmonary fibrosis, transplantation rejection, graft-versus-host disease and cancer.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Methods of Treating or Preventing CCR9-mediated Conditions or Diseases

In yet another aspect, the present invention provides methods of treating or preventing a CCR9-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. For example, compounds for use in treating or preventing a CCR9-mediated condition or disease may include compounds of the formula (I) wherein Ar is selected from the group consisting of:

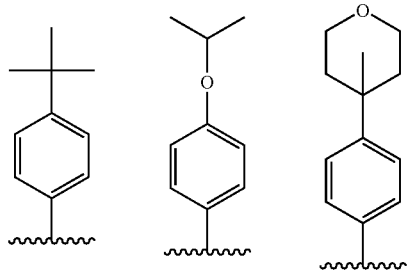

-continued

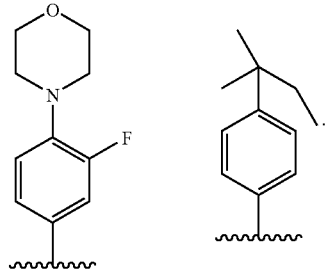

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, and (15) irritable bowel syndrome.

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

In yet other embodiments, the present methods are directed to the treatment of psoriasis where a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Preparation of Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenylarylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

EXAMPLES

Exemplary compounds used in the method of the invention and in pharmaceutical compositions of the invention include but are not limited to the compounds listed in Table 1. Pharmaceutically acceptable salts of the compounds listed in Table 1 are also useful in the method of the invention and in pharmaceutical compositions of the invention.

TABLE 1

Exemplary compounds

| | $X^1$ | $X^2$ | $Y^6$ | $R^1$ | $R^2$ |
|---|---|---|---|---|---|
| 1. | t-butyl | H | Cl | —CH(CH$_3$)$_2$ | —CH$_3$ |
| 2. | t-butyl | H | Cl | —CH(CH$_3$)$_2$ | H |

TABLE 1-continued

Exemplary compounds

| | X¹ | X² | Y⁶ | R¹ | R² |
|---|---|---|---|---|---|
| 3. | t-butyl | H | Cl | —CH(CH₃)₂ | C(CH₃)₂OH |
| 4. | t-butyl | H | Cl | —CH₃ | H |
| 5. | t-butyl | H | Cl | —CH₃ | —CH(CH₃)₂ |
| 6. | t-butyl | H | Cl | —CH₂CH₃ | —CH₂OCH₃ |
| 7. | t-butyl | H | Cl | —CH₃ | 4-pyridyl (C(CH₃)₂-) |
| 8. | t-butyl | H | Cl | —CH(CH₃)₂ | C(CH₃)₂C(O)NHCH₃ |
| 9. | t-butyl | H | Cl | C(CH₃)₂(2-F-C₆H₄) | H |
| 10. | t-butyl | H | Cl | —CH₂CH₃ | H |
| 11. | t-butyl | H | Cl | —CH₃ | —CH₃ |
| 12. | t-butyl | H | Cl | —CH₃ | CH(CH₃)(3-pyridyl) |
| 13. | t-butyl | H | Cl | —CH₃ | 5-(2-methyl)-isoxazolyl |
| 14. | t-butyl | H | Cl | —CH₃ | —CH₂OCH₃ |
| 15. | t-butyl | H | Cl | (3R)-pyrrolidinyl | H |
| 16. | t-butyl | H | Cl | (3S)-piperidinyl | H |
| 17. | t-butyl | H | Cl | —CH₂CH₃ | —CH₃ |
| 18. | t-butyl | H | Cl | —CH(CH₃)₂ | C(CH₃)₂C(O)N(CH₃)₂ |
| 19. | t-butyl | H | Cl | —CH(CH₃)₂ | —CH₂OCH₃ |
| 20. | t-butyl | H | Cl | C₆H₅ | H |
| 21. | t-butyl | H | Cl | 1-cyclopropyl-1-methylethyl | —CH₃ |

TABLE 1-continued

Exemplary compounds

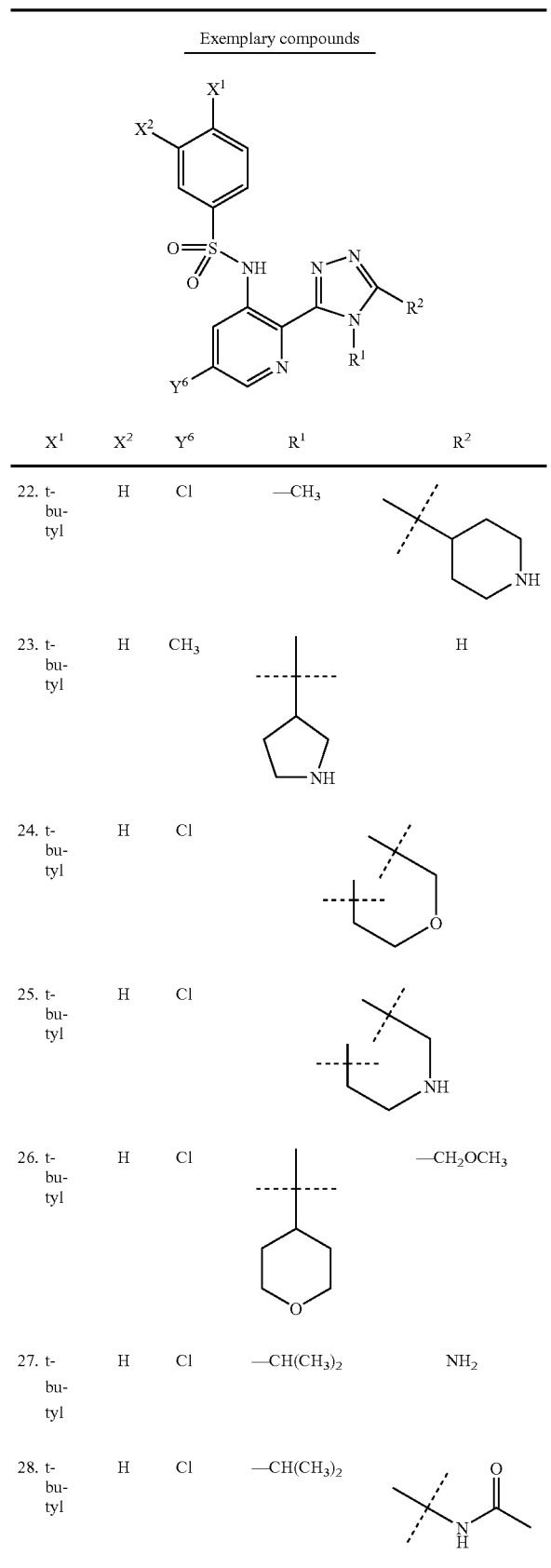

| | $X^1$ | $X^2$ | $Y^6$ | $R^1$ | $R^2$ |
|---|---|---|---|---|---|
| 22. | t-butyl | H | Cl | —CH₃ | 4-piperidinyl |
| 23. | t-butyl | H | CH₃ | 3-pyrrolidinyl | H |
| 24. | t-butyl | H | Cl | tetrahydropyran-2-yl | |
| 25. | t-butyl | H | Cl | 3-piperidinyl | |
| 26. | t-butyl | H | Cl | tetrahydropyran-4-yl | —CH₂OCH₃ |
| 27. | t-butyl | H | Cl | —CH(CH₃)₂ | NH₂ |
| 28. | t-butyl | H | Cl | —CH(CH₃)₂ | —C(CH₃)₂NHC(O)CH₃ |

TABLE 1-continued

Exemplary compounds

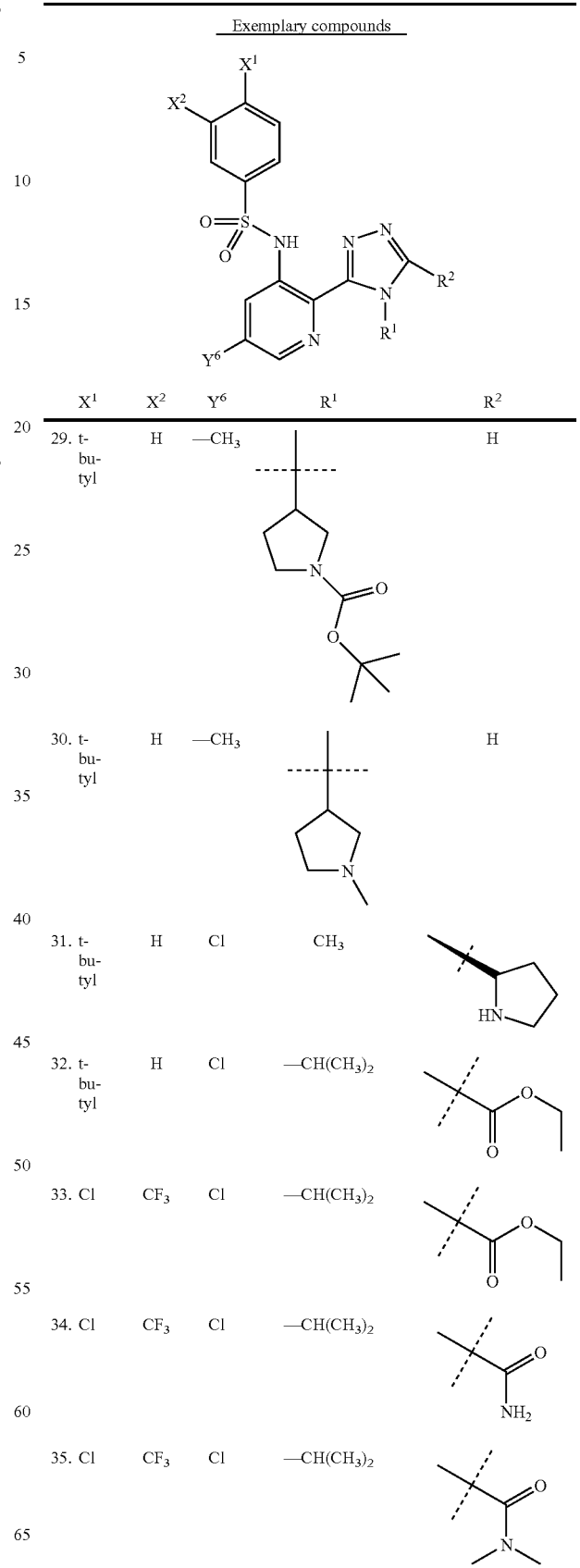

| | $X^1$ | $X^2$ | $Y^6$ | $R^1$ | $R^2$ |
|---|---|---|---|---|---|
| 29. | t-butyl | H | —CH₃ | N-Boc-pyrrolidin-3-yl | H |
| 30. | t-butyl | H | —CH₃ | 1-methylpyrrolidin-3-yl | H |
| 31. | t-butyl | H | Cl | CH₃ | pyrrolidin-2-yl |
| 32. | t-butyl | H | Cl | —CH(CH₃)₂ | —C(CH₃)₂C(O)OEt |
| 33. | Cl | CF₃ | Cl | —CH(CH₃)₂ | —C(CH₃)₂C(O)OEt |
| 34. | Cl | CF₃ | Cl | —CH(CH₃)₂ | —C(CH₃)₂C(O)NH₂ |
| 35. | Cl | CF₃ | Cl | —CH(CH₃)₂ | —C(CH₃)₂C(O)N(CH₃)₂ |

TABLE 1-continued
Exemplary compounds
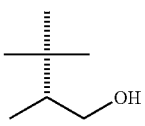
| | $X^1$ | $X^2$ | $Y^6$ | $R^1$ | $R^2$ |
|---|---|---|---|---|---|
| 36. | Cl | CF$_3$ | Cl | 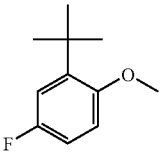 | H |
| 37. | Cl | CF$_3$ | Cl | —CH(CH$_3$)$_2$ | Br |
| 38. | Cl | CF$_3$ | Cl | 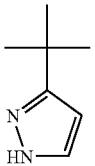 | H |
| 39. | Cl | CF$_3$ | CH$_3$ | 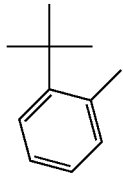 | H |
| 40. | Cl | CF$_3$ | Cl | 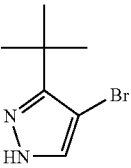 | H |
| 41. | Cl | CF$_3$ | Cl | 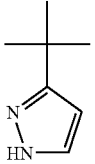 | H |
| 42. | Cl | CF$_3$ | Cl | 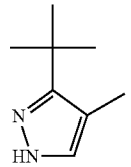 | H |
TABLE 1-continued
Exemplary compounds
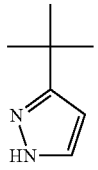
| | $X^1$ | $X^2$ | $Y^6$ | $R^1$ | $R^2$ |
|---|---|---|---|---|---|
| 43. | Cl | CF$_3$ | Cl | 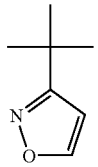 | H |
| 44. | Cl | CF$_3$ | Cl | 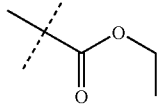 | —CH(CH$_3$)$_2$ |
| 45. | Cl | CF$_3$ | Cl | 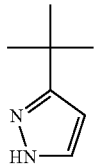 | 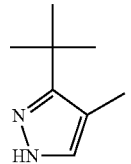 |
| 46. | Cl | CF$_3$ | Cl | 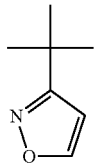 | CF$_3$ |
| 47. | Cl | CF$_3$ | Cl | 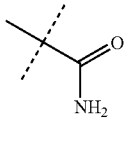 | H |
| 48. | Cl | CF$_3$ | Cl |  |  |

TABLE 1-continued

Exemplary compounds

| | $X^1$ | $X^2$ | $Y^6$ | $R^1$ | $R^2$ |
|---|---|---|---|---|---|
| 49. | Cl | CF₃ | Cl | 3-(2-methylpropan-2-yl)isoxazole | N,N-dimethylisobutyramide |
| 50. | Cl | CF₃ | Cl | 4-bromo-3-(tert-butyl)-1H-pyrazole | CH₃ |
| 51. | Cl | CF₃ | Cl | 3-(tert-butyl)-1H-pyrazole | ethoxymethyl |
| 52. | Cl | CF₃ | Cl | 3-(tert-butyl)isoxazole | ethoxymethyl |
| 53. | Cl | CF₃ | Cl | —CH(CH₃)₂ | NH₂ |
| 54. | Cl | CF₃ | Cl | 3-(tert-butyl)-1H-pyrazole | cyclopropyl(methyl) |
| 55. | Cl | CF₃ | Cl | 3-(tert-butyl)isoxazole | N-ethyl isobutyramide |
| 56. | Cl | CF₃ | Cl | 3-(tert-butyl)isoxazole | pyrrolidinyl ketone |
| 57. | Cl | CF₃ | Cl | 3-(tert-butyl)isoxazole | N-isopropyl isobutyramide |
| 58. | Cl | Cl | Cl | 3-(tert-butyl)-1H-pyrazole | H |
| 59. | Cl | Cl | Cl | 3-(tert-butyl)isoxazole | H |
| 60. | Cl | CF₃ | Cl | 3-(tert-butyl)-1H-pyrazole | —C(CH₃)₃ |
| 61. | Cl | CF₃ | Cl | 3-(tert-butyl)isoxazole | Br |

TABLE 1-continued

Exemplary compounds

| | X¹ | X² | Y⁶ | R¹ | R² |
|---|---|---|---|---|---|
| 62. | Cl | Cl | Cl | 4-bromo-3-tert-butyl-1H-pyrazol-5-yl | H |
| 63. | Cl | CF₃ | Cl | 4-bromo-3-tert-butyl-1H-pyrazol-5-yl | Br |
| 64. | Cl | CF₃ | Cl | 3-tert-butylisoxazol-5-yl | N-ethyl-N-methylcarbamoyl |
| 65. | Cl | CF₃ | CH₃ | 3-tert-butylisoxazol-5-yl | CHO |
| 66. | Cl | CF₃ | Br | 3-tert-butyl-1H-pyrazol-5-yl | H |
| 67. | Cl | CF₃ | Br | 3-tert-butylisoxazol-5-yl | H |
| 68. | Cl | Cl | Cl | 3-tert-butylisoxazol-5-yl | C(CH₃)₂C(O)NH₂ |
| 69. | CH₃ | CF₃ | Cl | 3-tert-butylisoxazol-5-yl | C(CH₃)₂C(O)NH₂ |
| 70. | Cl | CF₃ | CH₃ | 2-phenylpropan-2-yl | C(CH₃)₂C(O)NH₂ |
| 71. | Cl | CF₃ | Cl | —CH(CH₃)₂ | C(CH₃)₂CH₂N(CH₃)₂ |
| 72. | Cl | CF₃ | Cl | 5-tert-butyl-1-methyl-1H-pyrazol-3-yl | H |
| 73. | Cl | CF₃ | Cl | 3-(2-methylpropan-2-yl)pyrrolidin-3-yl | H |

TABLE 1-continued

Exemplary compounds

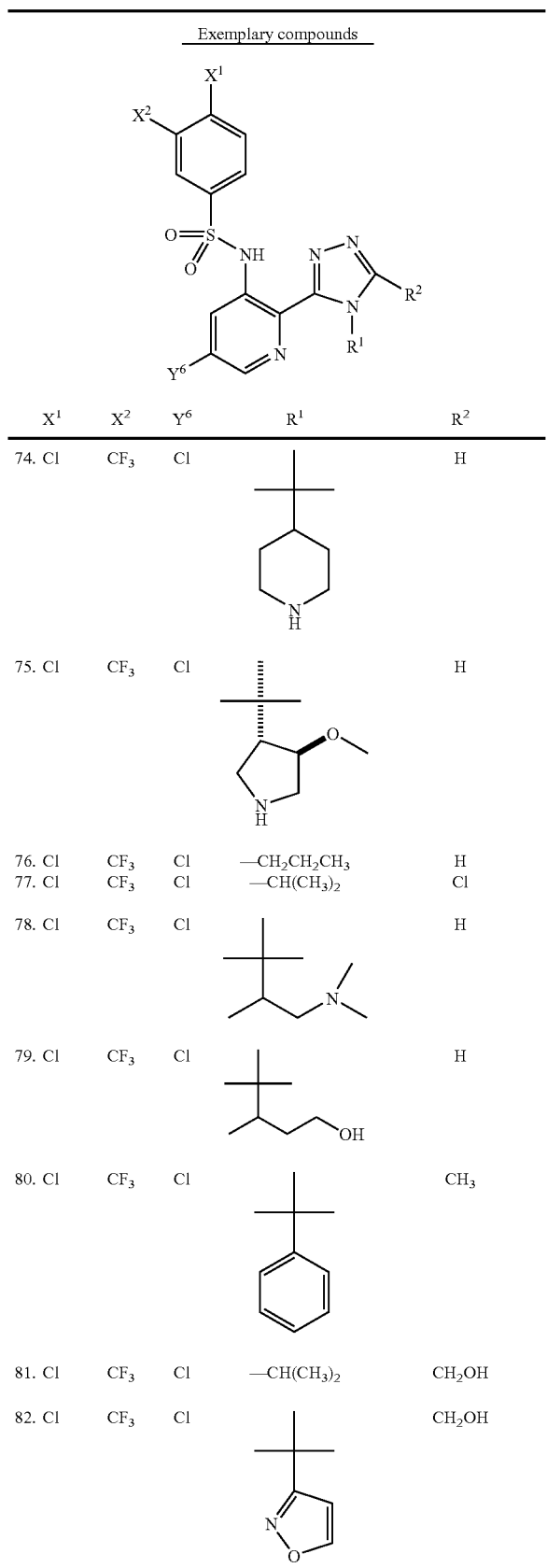

| | $X^1$ | $X^2$ | $Y^6$ | $R^1$ | $R^2$ |
|---|---|---|---|---|---|
| 74. | Cl | $CF_3$ | Cl | (4-piperidinyl-methyl-methyl) | H |
| 75. | Cl | $CF_3$ | Cl | (3-methoxypyrrolidinyl) | H |
| 76. | Cl | $CF_3$ | Cl | —$CH_2CH_2CH_3$ | H |
| 77. | Cl | $CF_3$ | Cl | —$CH(CH_3)_2$ | Cl |
| 78. | Cl | $CF_3$ | Cl | (dimethylaminoalkyl) | H |
| 79. | Cl | $CF_3$ | Cl | (hydroxyalkyl) | H |
| 80. | Cl | $CF_3$ | Cl | (benzyl-type) | $CH_3$ |
| 81. | Cl | $CF_3$ | Cl | —$CH(CH_3)_2$ | $CH_2OH$ |
| 82. | Cl | $CF_3$ | Cl | (isoxazolyl-alkyl) | $CH_2OH$ |

TABLE 1-continued

Exemplary compounds

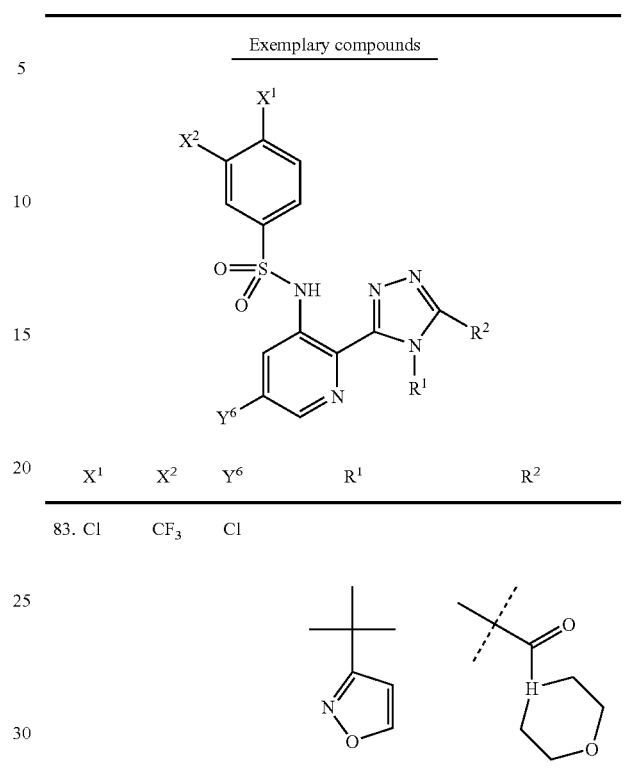

| | $X^1$ | $X^2$ | $Y^6$ | $R^1$ | $R^2$ |
|---|---|---|---|---|---|
| 83. | Cl | $CF_3$ | Cl | (isoxazolyl-t-butyl) | (morpholinyl carbonyl) |

The above compounds and others within the scope of this invention can be made and tested for activity using the following procedures.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system General Procedure A Exemplified by 5-Chloro-3-(4-tert-butyl-phenylsulfonamido) picolinic acid

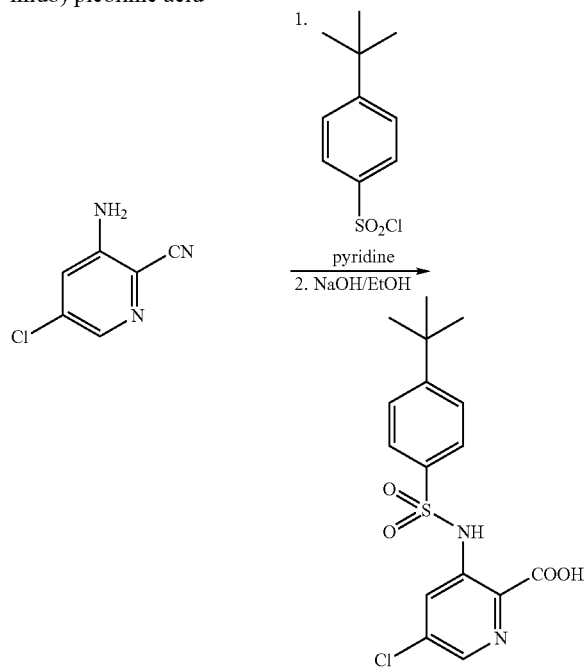

A 25 mL round-bottom flask was charged with 3-amino-2-cyano-5-chloropyridine (1.04 g, 6.8 mmol), 4-tert-butyl-benzenesulfonyl chloride (2.09 g, 8.8 mmol), and pyridine (6 mL). The resultant solution was heated to 70° C. and stirred for 5 h. The pyridine was removed in vacuo and 70% aqueous EtOH (20 mL) was added, followed by NaOH (3.20 g, 80 mmol). The mixture was stirred at reflux for 12 h. The solvent was subsequently removed in vacuo and ice (10 g) was added. The pH was adjusted to 2-3 with concentrated HCl. The resultant aqueous solution was extracted with EtOAc, washed with brine, dried over MgSO$_4$, and concentrated under reduced pressure. The light yellow solid was recrystallized from EtOAc/hexane (1:1) to afford the desired acid as white needles (735 mg): MS (ES) M+H expected 369.1, found 369.0.

Example 2

N-(5-Chloro-2-(hydrazinecarbonyl)pyridine-3-yl)-4-tert-butyl-benzenesulfonamide

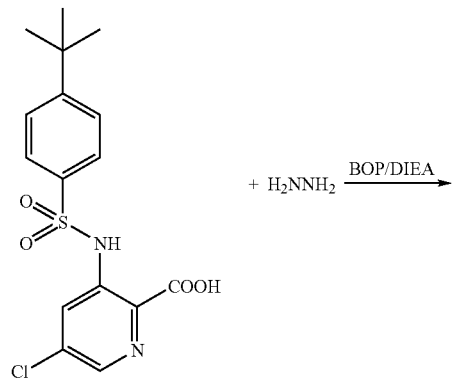

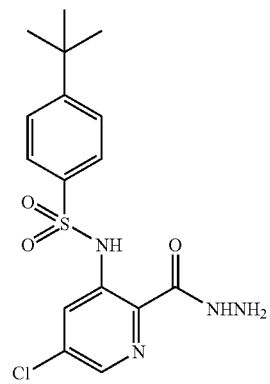

A 25 mL round-bottom flask vial was charged with 5-chloro-3-(4-tert-butyl-phenylsulfonamido)picolinic acid (735 mg, 2 mmol), BOP (1.77 g, 4 mmol), anhydrous hydrazine (1.2 mL), and anhydrous DMF (5 mL). The resultant solution was stirred for 2 h at room temperature and then diluted with water. The reaction mixture was subsequently extracted with EtOAc, and the combined organics were washed with brine, dried over MgSO$_4$, and concentrated under reduced pressure. The light yellow solid was recrystallized from EtOAc/hexane (1:1) to afford the desired hydrazide as a white solid (613 mg): MS (ES) M+H expected 383.1, found 383.0.

Example 3

4-tert-Butyl-N-(2-hydrazinocarbonyl-5-methyl-pyridin-3-yl)-benzenesulfonamide

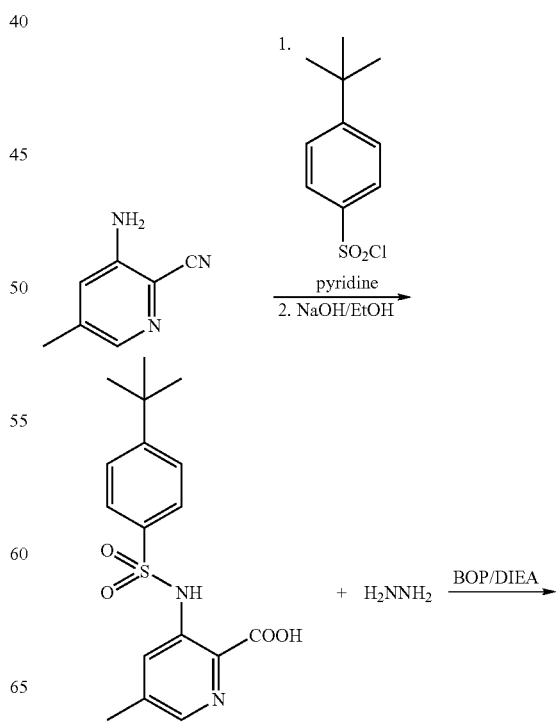

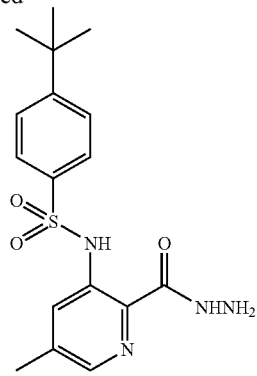

4-tert-Butyl-N-(2-hydrazinocarbonyl-5-methyl-pyridin-3-yl)-benzenesulfonamide was synthesized from 3-amino-5-methyl-pyridine-2-carbonitrile according to general procedure A.

General Procedure B

Exemplified by 4-tert-Butyl-N-[6-chloro-2-(4-ethyl-5-methyl-4H-[1,2,4]triazol-3-yl)-pyridin-3-yl]-benzenesulfonamide

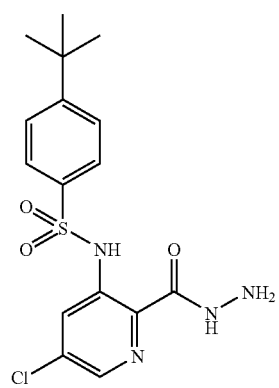

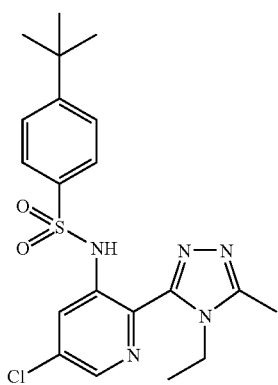

A 25 mL scintillation vial was charged with 4-tert-butyl-N-(6-chloro-2-hydrazinocarbonyl-pyridin-3-yl)-benzenesulfonamide (691 mg, 1.8 mmol), trimethyl orthoacetate (0.35 mL, 2.8 mmol), ethylamine (5 mL, 2.0 M), AcOH (3.0 mL), and dioxane (10 mL). The vial was sealed, heated to 130° C., and stirred for three hours. The volatiles were then evacuated in vacuo and the residue was purified via automated silica gel chromatography and then preparative HPLC to afford 4-tert-butyl-N-[6-chloro-2-(4-ethyl-5-methyl-4H-[1,2,4]triazol-3-yl)-pyridin-3-yl]-benzenesulfonamide as a white powder: MS (ES) M+H expected 434.1, found 434.1.

General Procedure C

Exemplified by 4-tert-Butyl-N-[6-chloro-2-(4-isopropyl-5-methoxymethyl-4H-[1,2,4]triazol-3-yl)-pyridin-3-yl]-benzenesulfonamide

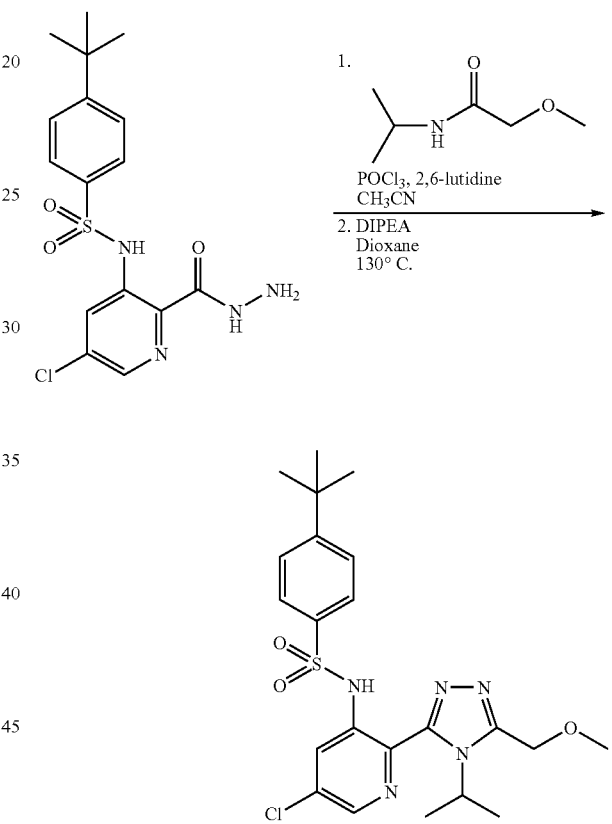

A 25 mL scintillation vial was charged with N-isopropyl-2-methoxyacetamide (132 mg, 1.0 mmol), POCl$_3$ (0.19 mL, 2.0 mmol), 2,6-lutidine (0.30 mL, 2.4 M), and CH$_3$CN (10 mL). The vial was sealed, heated to 40° C., and stirred for four hours. The volatiles were then evacuated in vacuo and to the residue was added 4-tert-butyl-N-(6-chloro-2-hydrazinocarbonyl-pyridin-3-yl)-benzenesulfonamide (193 mg, 0.5 mmol), DIPEA (2.0 mL), and dioxane (2.0 mL). The vial was sealed, heated to 130° C., and stirred for two hours. The volatiles was then evacuated in vacuo, and the residue was purified via automated silica gel chromatography and then preparative HPLC to afford 4-tert-butyl-N-[6-chloro-2-(4-isopropyl-5-methoxymethyl-4H-[1,2,4]triazol-3-yl)-pyridin-3-yl]-benzenesulfonamide as a white powder: MS (ES) M+H expected 478.2, found 478.1.

General Procedure D

Exemplified by 4-tert-Butyl-N-[5-chloro-2-(4-methyl-5-piperidin-4-yl-4H-[1,2,4]triazol-3-yl)-pyridin-3-yl]-benzenesulfonamide

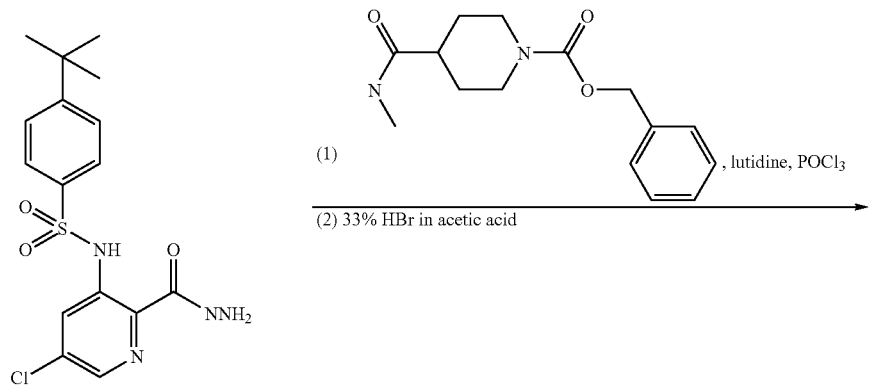

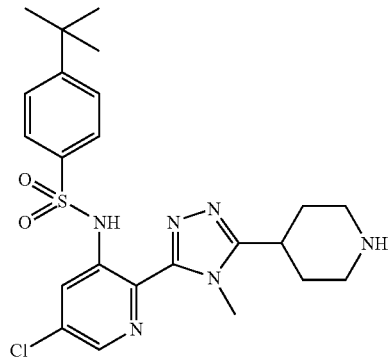

A 25 mL scintillation vial was charged with 4-methylcarbamoyl-piperidine-1-carboxylic acid benzyl ester (138 mg, 0.5 mmol), POCl$_3$ (0.095 mL, 1.0 mmol), 2,6-lutidine (130 mg, 1.25 mmol), and CH$_3$CN (1.5 mL). The vial was sealed, heated to 40° C., and stirred for four hours. The volatiles were then evacuated in vacuo and to the resultant residue was added 4-tert-butyl-N-(6-chloro-2-hydrazinocarbonyl-pyridin-3-yl)-benzenesulfonamide (193 mg, 0.5 mmol), DIPEA (0.5 mL), and dioxane (1.0 mL). The vial was sealed, heated to 130° C., and stirred for two hours. The volatiles were then removed in vacuo and to the residue was added 3 mL of 33% hydrobromic acid in acetic acid. The vial was sealed and stirred for 3 h. The volatiles were then evacuated in vacuo and the residue was purified via preparatory HPLC to afford 4-tert-butyl-N-[5-chloro-2-(4-methyl-5-piperidin-4-yl-4H-[1,2,4]triazol-3-yl)-pyridin-3-yl]-benzenesulfonamide as a white powder: MS (ES) M+H expected 489.2, found 488.5.

General Procedure E

Exemplified by 5-[3-(4-tert-Butyl-benzenesulfonylamino)-5-chloro-pyridin-2-yl]-4-isopropyl-4H-[1,2,4]triazole-3-carboxylic acid dimethylamide

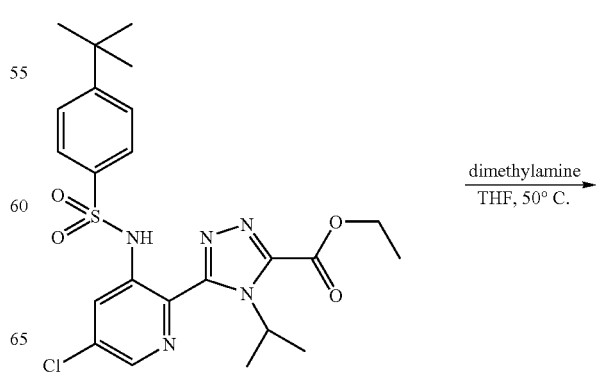

-continued

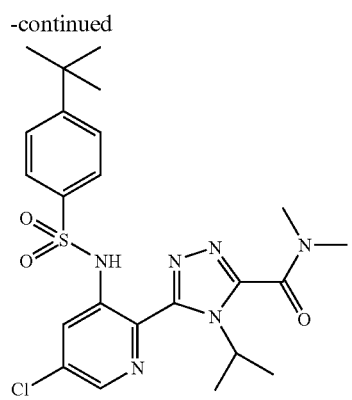

A 25 mL scintillation vial was charged with 5-[3-(4-tert-butyl-benzenesulfonylamino)-5-chloro-pyridin-2-yl]-4-isopropyl-4H-[1,2,4]triazole-3-carboxylic acid ethyl ester (prepared according to general procedure B, 11 mg, 0.02 mmol), dimethylamine in THF (2 mL, 2.0 M), and KCN (1 mg, 0.01 mmol). The vial was sealed and stirred at 50° C. for 16 h. The volatiles were then evacuated in vacuo and the residue was purified via preparatory HPLC to afford 4-tert-butyl-N-[6-chloro-2-(4-ethyl-5-methyl-4H-[1,2,4]triazol-3-yl)-pyridin-3-yl]-enzenesultonamide as a white powder: MS (ES) M+H expected 505.2, found 505.5.

General Procedure F

Exemplified by 4-tert-Butyl-N-{5-chloro-2-[5-(1-hydroxy-1-methyl-ethyl)-4-isopropyl-4H-[1,2,4]triazol-3-yl]-pyridin-3-yl}-benzenesulfonamide

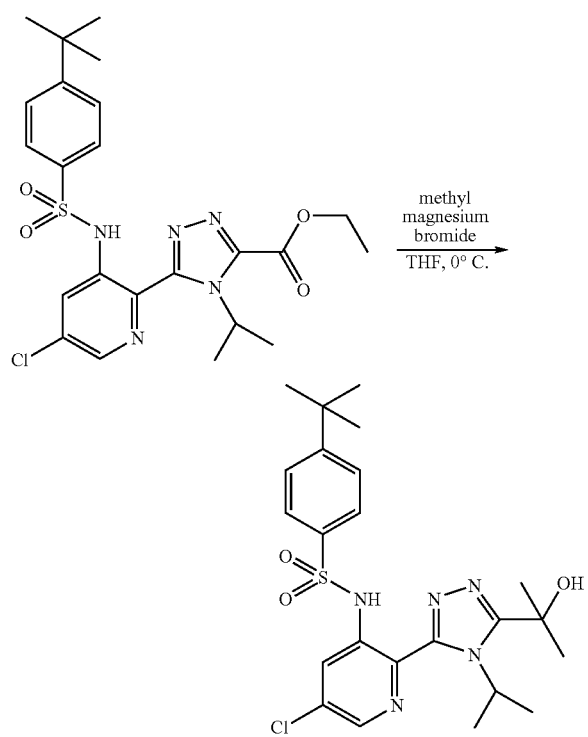

A 25 mL scintillation vial was charged with 5-[3-(4-tert-butyl-benzenesulfonylamino)-5-chloro-pyridin-2-yl]-4-isopropyl-4H-[1,2,4]triazole-3-carboxylic acid ethyl ester (prepared according to general procedure B, 11 mg, 0.02 mmol), methylmagnesium bromide in THF (0.2 mL, 3.0 M), and tetrahydrofuran (3 mL). The vial was sealed and stirred at 0° C. for 2 h. The volatiles were then evacuated in vacuo and the residue was purified via preparatory HPLC to afford 4-tert-butyl-N-{5-chloro-2-[5-(1-hydroxy-1-methyl-ethyl)-4-isopropyl-4H-[1,2,4]triazol-3-yl]-pyridin-3-yl}-benzenesulfonamide as a white powder: MS (ES) M+H expected 492.2, found 492.5.

General Procedure G

Exemplified by N-[2-(5-Amino-4-isopropyl-4H-[1,2,4]triazol-3-yl)-4-chloro-phenyl]-4-tert-butyl-benzenesulfonamide

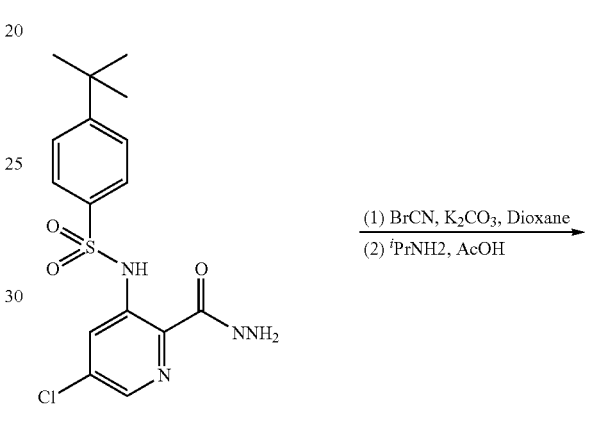

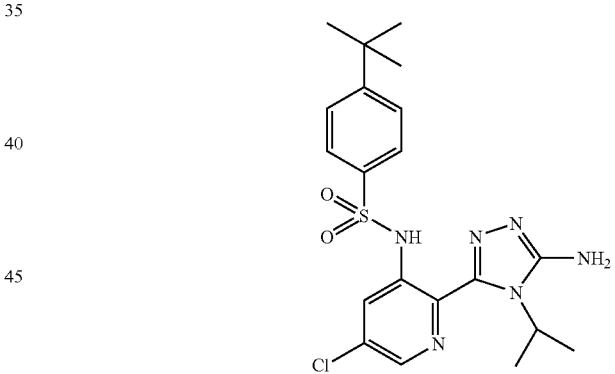

Cyanogen bromide (110.9 mg, 1.05 mmol) was added to a solution of 4-tert-butyl-N-(6-chloro-2-hydrazinocarbonyl-pyridin-3-yl)-benzenesulfonamide (200 mg, 0.524 mmol) and potassium carbonate (145 mg, 1.05 mmol) in dioxane (2 mL). The resultant mixture reaction was stirred for 18 h at room temperature. Isopropyl amine (0.18 mL, 2.09 mmol) and acetic acid (0.15 mL) were subsequently added and the reaction was heated at 135° C. for 18 h. The crude mixture was partitioned between ethyl acetate and water and the layers were separated. The organic phase was washed with 1 N HCl, saturated sodium bicarbonate, and brine; dried over magnesium sulfate, and concentrated in vacuo. The crude product was subsequently purified via flash column chromatography (10-100% ethyl acetate and hexane) followed by preparative HPLC (10-90% gradient of MeCN-water) to afford the title compound as a white solid: MS (ES) M+H expected 449.1, found 449.2.

General Procedure H

Exemplified by N-{5-[3-(4-tert-Butyl-benzenesulfonylamino)-5-chloro-pyridin-2-yl]-4-isopropyl-4H-[1,2,4]triazol-3-yl}-acetamide

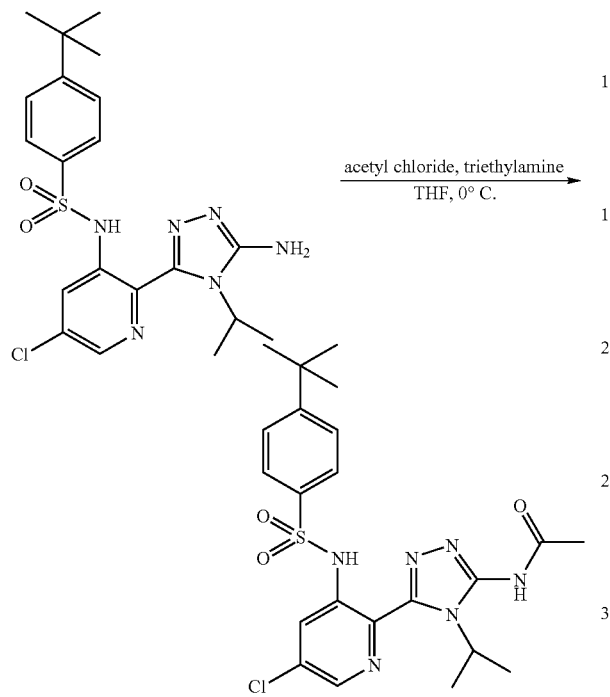

A 25 mL scintillation vial was charged with N-[2-(5-amino-4-isopropyl-4H-[1,2,4]triazol-3-yl)-4-chloro-phenyl]-4-tert-butyl-benzenesulfonamide (9 mg, 0.02 mmol), acetyl chloride (7.9 mg, 0.1 mmol), triethylamine (10 mg, 0.1 mmol), and tetrahydrofuran (2 mL). The vial was sealed and stirred at 0° C. for 2 h. The volatiles were then evacuated in vacuo and the crude product was purified by flash column chromatography (10-100% ethyl acetate and hexane) followed by preparative HPLC (10-90% gradient of MeCN-water) to afford the title compound as a white solid: MS (ES) M+H expected 491.5, found 491.5.

General Procedure I

Exemplified by 4-tert-Butyl-N-[5-chloro-2-(4-pyrrolidin-3-yl-4H-[1,2,4]triazol-3-yl)-pyridin-3-yl]-benzenesulfonamide

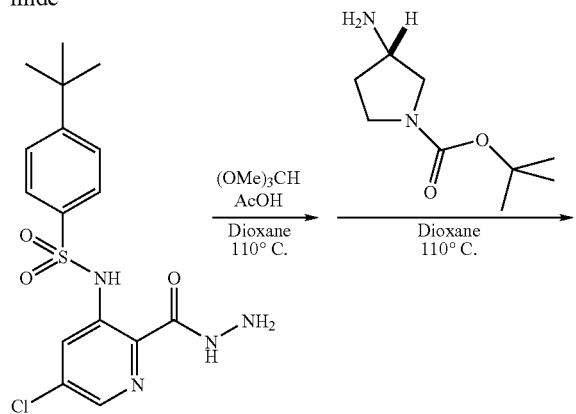

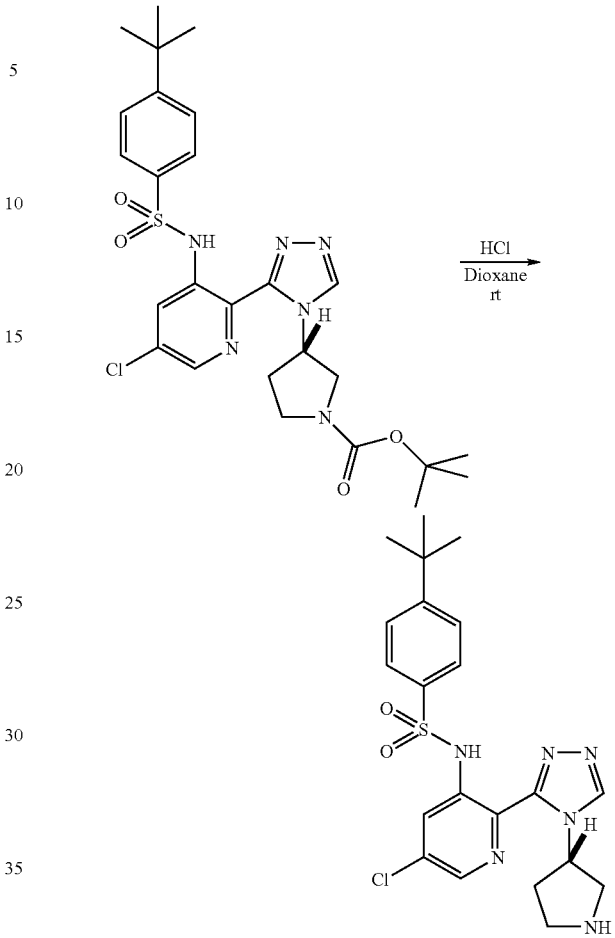

Step 1: A 25 mL scintillation vial was charged with 4-tert-butyl-N-(5-chloro-2-hydrazinocarbonyl-pyridin-3-yl)-benzenesulfonamide (191 mg, 0.50 mmol), trimethyl orthoformate (0.072 mL, 0.65 mmol), AcOH (0.60 mL), and dioxane (1.5 mL). The vial was sealed, heated to 110° C., and stirred overnight. The following day, the intermediate methyl carbazate was observed at m/z 425 (via LCMS). 1-Boc-3-aminopyrrolidine (187 mg, 1.0 mmol) was subsequently added and the reaction continued at 110° C. until LCMS analysis indicated consumption of the oxadiazole intermediate. The volatiles were subsequently evacuated in vacuo and the residue was purified via reverse-phase HPLC to provide 3-{3-[3-(4-tert-butyl-benzenesulfonylamino)-5-chloro-pyridin-2-yl]-[1,2,4]triazol-4-yl}-pyrrolidine-1-carboxylic acid tert-butyl ester as a white solid: MS (ES) M+H expected 561.1, found 561.1.

Step 2: The crude triazole, dissolved in a minimal amount of dioxane (0.3 mL), was treated with 4 N HCl in dioxane (1.0 mL). The vial was flushed with nitrogen, stirred 5 h (the reaction was monitored by LCMS), and then concentrated in vacuo. Purification by preparative HPLC provided 107 mg of the desired product, 4-tert-butyl-N-[5-chloro-2-(4-pyrrolidin-3-yl-4H-[1,2,4]triazol-3-yl)-pyridin-3-yl]-benzenesulfonamide, as a white solid: MS (ES) M+H expected 461.1, found 461.0.

1H-Pyrazol-4-ylamine

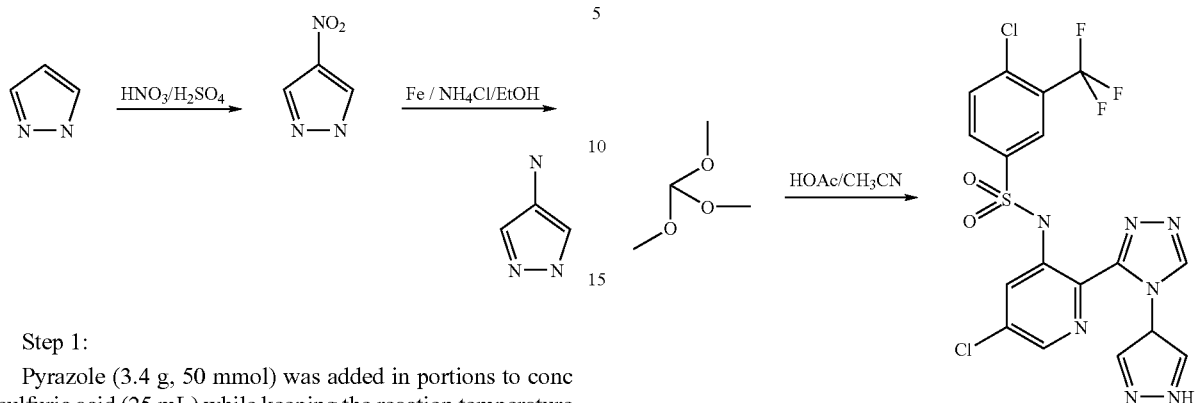

Step 1:

Pyrazole (3.4 g, 50 mmol) was added in portions to conc sulfuric acid (25 mL) while keeping the reaction temperature below 40° C. To this solution was then added 70% nitric acid (3.5 mL) dropwisely while maintaining the temperature below 55° C. The mixture was stirred at this temperature for 4 hours. After cooling to room temperature, the mixture was slowly poured into 500 grams of ice. The resultant mixture was neutralized with 50% aqueous NaOH and the resulting slurry was diluted with 500 mL of ethyl acetate. This mixture was filtered and the filtrate was washed with water (300 ml), brine (300 ml), and dried over $Na_2SO_4$. The solution was concentrated, and the precipitate was collected and dried in vacuo to afford the title compound as white crystals. MS (ES) $[M+H]^+$ expected 113.0, found 113.0.

Step 2:

To a stirred mixture of iron (1.68 g, 30 mmol), ammonium chloride (540 mg, 10 mmol), water (2 mL) and ethanol (8 mL) at 80° C. was added 4-nitro-1H-pyrazol (1.13 g, 10 mmol) in portions. After completion of addition, the mixture was stirred at 80° C. for additional 2 hours. After cooling to room temperature, the mixture was diluted with ethyl acetate, and the resultant mixture was filtered through a pad of celite. The filtrate was concentrated to afford the crude title compound which was used at next step without further purification. MS (ES) $[M+H]^+$ expected 84.0, found 84.0.

4-Chloro-N-{5-chloro-2-[4-(1H-pyrazol-4-yl)-4H-[1,2,4]triazol-3-yl]-pyridin-3-yl}-3-trifluoromethyl-benzenesulfonamide The title compound was prepared according to general Method B. Thusly, a mixture of trimethylorthoformate (53 mg, 0.50 mmol), acetonitrile (1.5 mL), and 1H-pyrazol-4-ylamine (83 mg, crude, 1.0 mmol) was stirred at 120° C. for 2 hours. After the mixture was cooled to room temperature, 4-Chloro-N-(5-chloro-2-hydrazinocarbonyl-pyridin-3-yl)-3-trifluoromethyl-benzenesulfonamide (42.8 mg, 0.10 mmol) and acetic acid (0.2 mL) was added and the resultant mixture was stirred at 120° C. for 2 hours. After evaporation of solvent under reduced pressure, the residue was further purified through automated normal-phase chromatography and dried (Lyophilizer) to afford title compound. 1H NMR: (DMSO-d6, ppm): 8.90 (s, 1H), 8.08 (m, 2H), 7.90 (m, 2H), 7.80 (m, 2H), 7.75 (m, 1H). MS (ES) $[M+H]^+$ expected 504.0, found 504.0.

4-Chloro-N-{5-chloro-2-[4-(2-methyl-2H-pyrazol-3-yl)-4H-[1,2,4]triazol-3-yl]-pyridin-3-yl}-3-trifluoromethyl-benzenesulfonamide

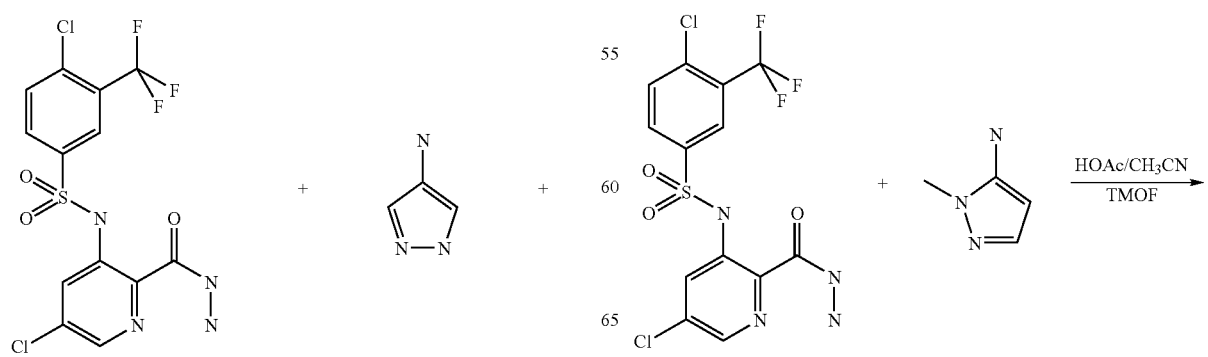

-continued

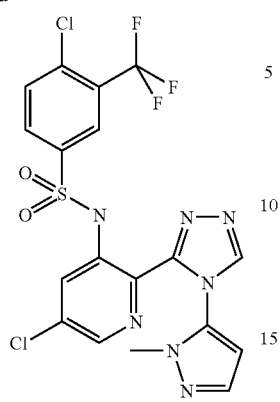

The title compound was prepared according to general Method B. using 4-Chloro-N-(5-chloro-2-hydrazinocarbonyl-pyridin-3-yl)-3-trifluoromethyl-benzenesulfonamide (100 mg, 0.234 mmol), trimethylorthoformate (80 mg, 0.75 mmol), acetonitrile (2 mL), 2-Methyl-2H-pyrazol-3-ylamine (48 mg, 0.50 mmol) and acetic acid (1.0 mL). MS (ES) [M+H]$^+$ expected 518.0, found 518.0.

3-{3-[5-Chloro-3-(4-chloro-3-trifluoromethyl-benzenesulfonylamino)-pyridin-2-yl]-[1,2,4]triazol-4-yl}-butyric acid ethyl ester

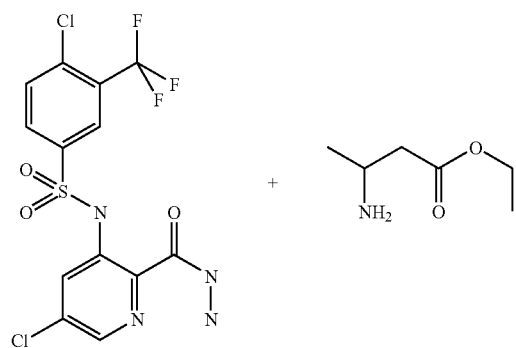

A mixture of 4-Chloro-N-(5-chloro-2-hydrazinocarbonyl-pyridin-3-yl)-3-trifluoromethyl-benzenesulfonamide (42.8 mg, 0.10 mmol), trimethylorthoformate (53 mg, 0.50 mmol), acetonitrile (1.5 mL), 3-Amino-butyric acid ethyl ester (131 mg, 1.0 mmol) and acetic acid (0.2 mL) was stirred at 120° C. for 2 hours. After evaporation of solvent under reduced pressure, the residue was further purified through automated normal-phase chromatography and dried (Lyophilizer) to afford title compound. MS (ES) [M+H]$^+$ expected 552.0, found 552.0.

4-Chloro-N-[5-chloro-2-(4-o-tolyl-4H-[1,2,4]triazol-3-yl)-pyridin-3-yl]-3-trifluoromethyl-benzenesulfonamide

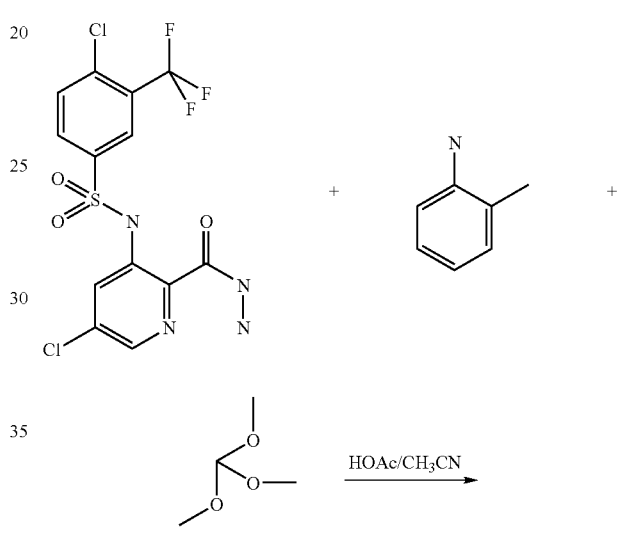

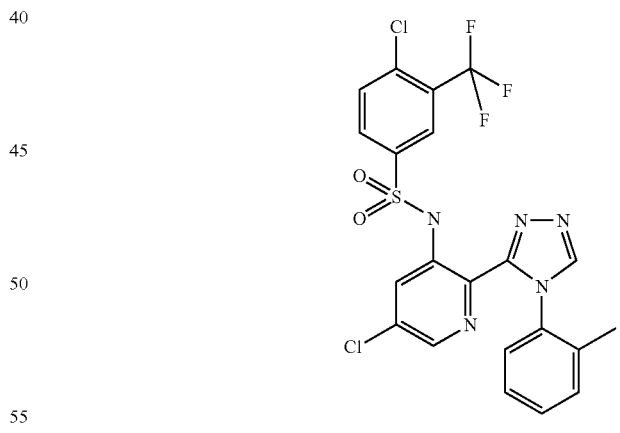

The title compound was prepared according to general Method B using 4-Chloro-N-(5-chloro-2-hydrazinocarbonyl-pyridin-3-yl)-3-trifluoromethyl-benzenesulfonamide (100 mg, 0.234 mmol), trimethylorthoformate (80 mg, 0.75 mmol), acetonitrile (2 mL), 2-methylaniline (62 mg, 0.50 mmol) and acetic acid (1.0 mL). 1H NMR: (CD3OD, ppm): 8.82 (s, 1H), 8.40 (s, 1H), 8.27 (d, 1H), 8.05 (m, 1H), 7.75 (d, 1H), 7.61 (s, 1H), 7.39 (m, 1H), 7.32 (m, 1H), 7.25 (m, 2H), 2.15 (s, 3H). MS (ES) [M+H]$^+$ expected 528.0, found 528.0.

4-Chloro-N-{5-chloro-2-[4-(5-fluoro-2-methoxy-phenyl)-4H-[1,2,4]triazol-3-yl]-pyridin-3-yl}-3-trifluoromethyl-benzenesulfonamide

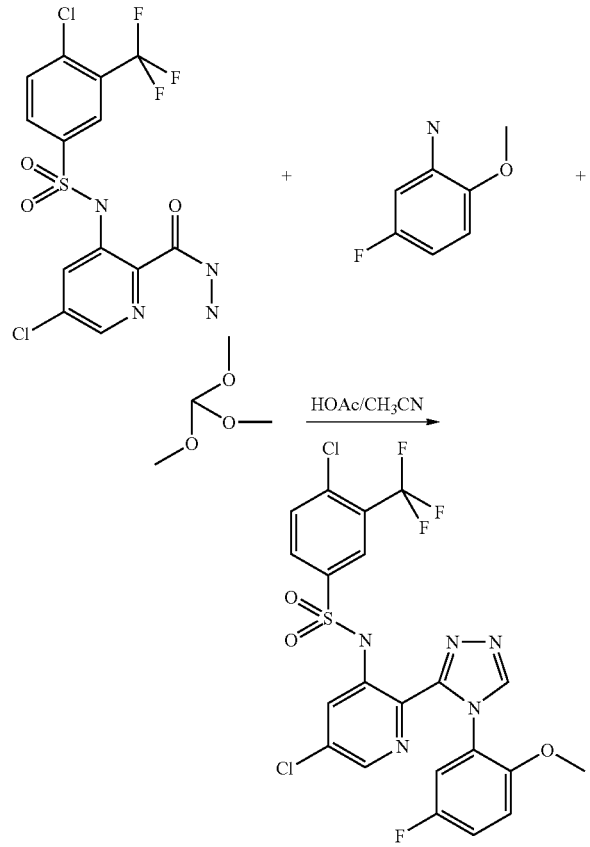

The title compound was prepared according to general Method B using 4-Chloro-N-(5-chloro-2-hydrazinocarbonyl-pyridin-3-yl)-3-trifluoromethyl-benzenesulfonamide (100 mg, 0.234 mmol), trimethylorthoformate (80 mg, 0.60 mmol), acetonitrile (2 mL), 2-methoxyl-5-fluoroaniline (70 mg, 0.50 mmol) and acetic acid (1.0 mL). MS (ES) [M+H]+ expected 562.0, found 562.0.

4-Chloro-N-{5-chloro-2-[4-(3-hydroxy-1-methyl-propyl)-4H-[1,2,4]triazol-3-yl]-pyridin-3-yl}-3-trifluoromethyl-benzenesulfonamide

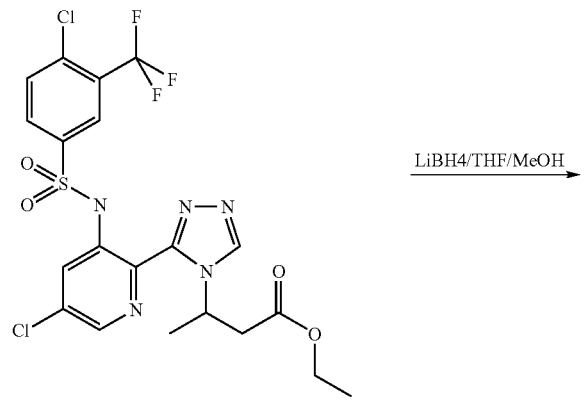

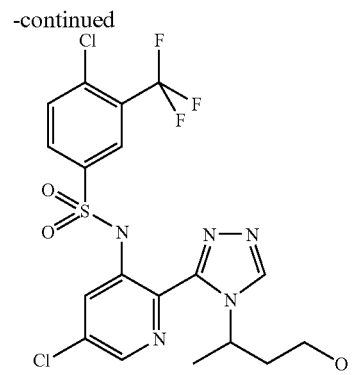

A mixture of 3-{3-[5-Chloro-3-(4-chloro-3-trifluoromethyl-benzenesulfonylamino)-pyridin-2-yl]-[1,2,4]triazol-4-yl}-butyric acid ethyl ester (27 mg, 0.05 mmol), lithium borohydride (2.0M, 0.14 ml, 0.28 mmol), 1.5 ml of THF and 0.02 ml of methanol was stirred at room temperature for 2 hours. The mixture was mixed with diluted HCl (1.0M), extracted with ethyl acetate, and the extracts were combined and washed with brine and dried. After concentration the residue was purified by prep TLC to afford title compound as a white solid. 1H NMR: (DMSO-d6, ppm): 9.03 (s, 1H), 8.30 (m, 1H), 8.11 (m, 1H), 8.02 (m, 1H), 7.91 (m, 1H), 7.83 (m, 1H), 3.28 (m, 1H), 3.19 (m, 2H), 1.91 (m, 2H), 1.42 (d, 3H). MS (ES) [M+H]+ expected 510.0, found 510.0.

4-Chloro-N-[5-chloro-2-(5-hydroxymethyl-4-isoxazol-3-yl-4H-[1,2,4]triazol-3-yl)-pyridin-3-yl]-3-trifluoromethyl-benzenesulfonamide

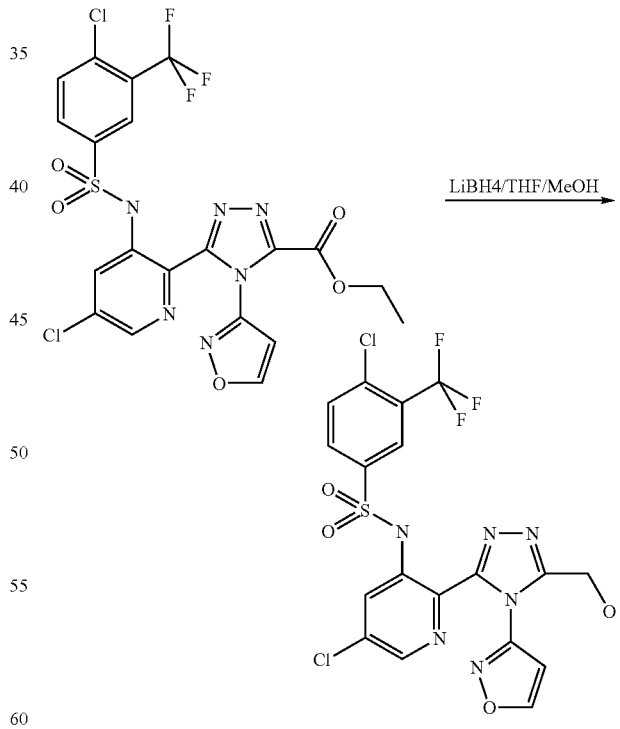

A mixture of 5-[5-Chloro-3-(4-chloro-3-trifluoromethyl-benzenesulfonylamino)-pyridin-2-yl]-4-isoxazol-3-yl-4H-[1,2,4]triazole-3-carboxylic acid ethyl ester (28 mg, 0.05 mmol), 0.14 ml (0.28 mmol) of lithium borohydride (2.0M) and 0.020 ml of methanol in 1.5 ml of THF was stirred at room temperature for 2 hours. The mixture was mixed with diluted HCl (1.0M), extracted with ethyl acetate, and the extracts were combined and washed with brine and dried. After concentration the residue was purified by prep TLC to afford title compound as a white solid. MS (ES) [M+H]+ expected 535.0, found 535.0

Ethyl 5-(3-(4-chloro-3-(trifluoromethyl)benzenesulfonamido)-5-chloropyridin-2-yl)-4-isopropyl-4H-1,2,4-triazole-3-carboxylate

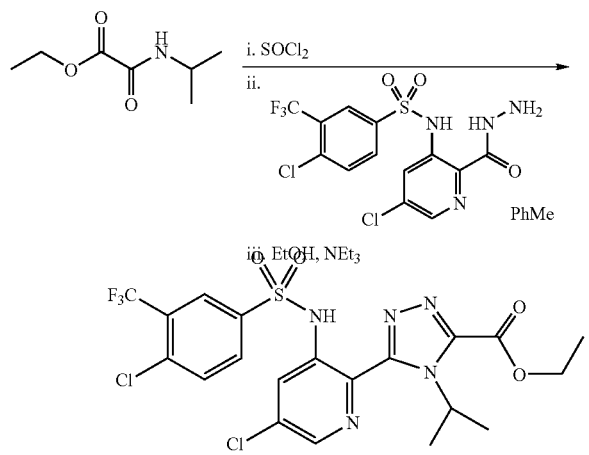

To a vial containing ethyl(isopropylcarbamoyl)formate (160 mg, 1.0 mmol) was added thionyl chloride (1.0 mL, 13.8 mmol). The vial was capped with a teflon coated septa and heated to 80° C. for 5 h. After cooling to room temperature, the volatiles were removed in vacuo. A solution of 4-chloro-N-(5-chloro-2-(hydrazinecarbonyl)pyridine-3-yl)-3-(trifluoromethyl)benzenesulfonamide (342 mg, 0.80 mmol) in toluene (3 mL) was added. The mixture was stirred at 40° C. for 16 h. After cooling to room temperature, the toluene was removed in vacuo. Ethanol (9 mL) and triethylamine (1 mL) were added, and the solution heated to 90° C. for 4 h. After cooling to room temperature, the volatiles were removed in vacuo, and the resulting residue purified by flash chromatography on 4 g of silica gel (0→20% gradient of MeOH in DCM). The pure fractions were collected, and the solvent removed in vacuo to afford the title compound (14 mg, 3% yield). HPLC retention time=3.17 minutes. ¹H NMR (400 MHz, CDCl₃) δ 8.39 (d, J=2.4, 1H), 8.19 (d, J=2.4, 1H), 8.04 (d, J=2.4, 1H), 7.89 (dd, J=2.0, 8.4, 1H), 7.53 (d, J=8.0, 1H), 5.66 (sept, J=7.0, 1H), 4.52 (q, J=7.4, 2H), 1.52 (d, J=7.0, 6H), 1.50 (t, J=7.4, 3H). MS (ES) [M+H]+ expected 552.0, found 552.0.

5-(3-(4-chloro-3-(trifluoromethyl)benzenesulfonamido)-5-chloropyridin-2-yl)-4-isopropyl-4H-1,2,4-triazole-3-carboxamide

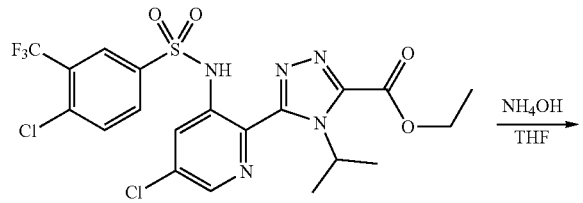

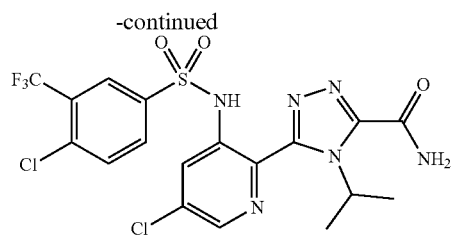

To a vial containing Ethyl 5-(3-(4-chloro-3-(trifluoromethyl)benzenesulfonamido)-5-chloropyridin-2-yl)-4-isopropyl-4H-1,2,4-triazole-3-carboxylate (59 mg, 0.1 mmol) was added THF (0.6 mL) and NH₄OH (0.2 mL). The solution was stirred at room temperature for 16 h. EtOAc (30 mL) was added. The organic phase washed with water (2×10 mL) and dried over Na₂SO₄. The volatiles were removed in vacuo. The resulting residue was purified by preparative HPLC (20→95% gradient of MeCN—H₂O with 0.1% TFA) and the pure fractions lyophilized to afford the title compound (4.0 mg, 8% yield). HPLC retention time=2.76 minutes. ¹H NMR (400 MHz, CDCl₃) δ 8.41 (d, J=2.0, 1H), 8.16 (d, J=2.0, 1H), 8.05 (d, J=2.4, 1H), 7.85 (dd, J=2.4, 8.4, 1H), 7.53 (d, J=8.4, 1H), 5.75 (sept, J=6.8, 1H), 1.52 (d, J=6.8, 6H). MS (ES) [M+H]+ expected 523.0, found 522.9.

5-(3-(4-chloro-3-(trifluoromethyl)benzenesulfonamido)-5-chloropyridin-2-yl)-isopropyl-N,N-dimethyl-4H-1,2,4-triazole-3-carboxamide

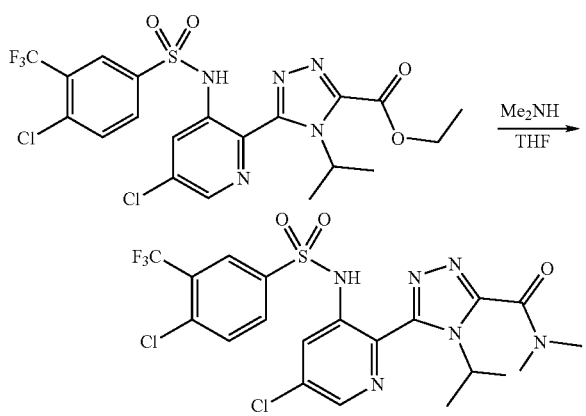

To a vial containing ethyl 5-(3-(4-chloro-3-(trifluoromethyl)benzenesulfonamido)-5-chloropyridin-2-yl)-4-isopropyl-4H-1,2,4-triazole-3-carboxylate (57 mg, 0.1 mmol) was added Me₂NH in THF (1.0 mL of a 2.0M solution). The solution was stirred at room temperature for 16 h. EtOAc (30 mL) was added. The organic phase washed with water (2×10 mL) and dried over Na₂SO₄. The volatiles were removed in vacuo. The resulting residue was purified by preparative HPLC (20→95% gradient of MeCN—H₂O with 0.1% TFA) and the pure fractions lyophilized to afford the title compound (3.7 mg, 7% yield). HPLC retention time=2.91 minutes. ¹H NMR (400 MHz, CDCl₃) δ 8.36 (d, J=2.0, 1H), 8.17 (d, J=2.4, 1H), 8.10 (d, J=2.4, 1H), 7.93 (dd, J=2.4, 8.4, 1H), 7.57 (d, J=8.4, 1H), 5.65 (sept, J=7.2, 1H), 3.20 (s, 3H), 3.12 (s, 3H), 1.52 (d, J=7.2, 6H). MS (ES) [M+H]+ expected 551.1, found 551.0.

Ethyl 5-(3-(4-chloro-3-(trifluoromethyl)benzene-sulfonamido)-5-chloropyridin-2-yl)-4-isoxazol-3-yl)-4H-1,2,4-triazole-3-carboxylate

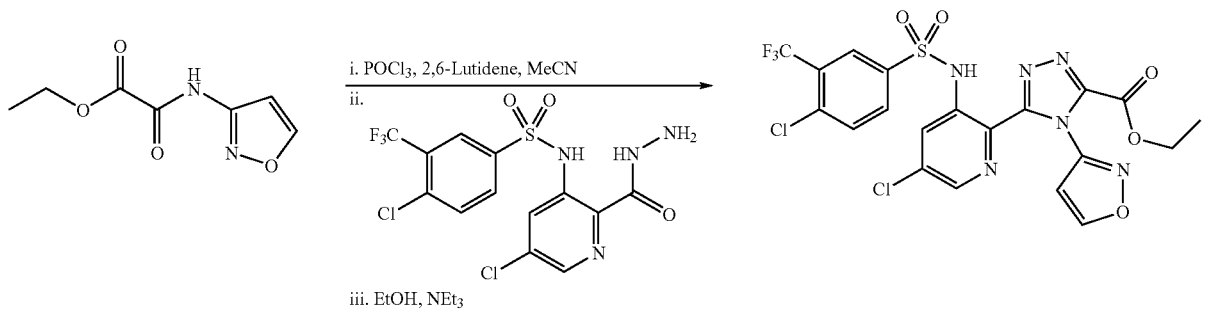

To a vial equipped with a teflon coated septum and a nitrogen inlet were added ethyl(isoxazol-3-ylcarbamoyl)formate (370 mg, 2.0 mmol), MeCN (2 mL) and 2,6-lutidine (0.6 mL, 5.2 mmol). The vial was cooled to 0° C. POCl$_3$ (0.4 mL, 4.3 mmol) was added, and the solution maintained at 0° C. for 30 min. The solution was then warmed to 40° C. for 3 h. After cooling to room temperature, solid 4-chloro-N-(5-chloro-2-(hydrazinecarbonyl)pyridine-3-yl)-3-(trifluoromethyl)-benzenesulfonamide (500 mg, 1.2 mmol) was added, and the reaction heated to 80° C. for 1 h. The volatiles were removed in vacuo. Ethanol (9 mL) and triethylamine (1 mL) were added, and the solution heated to 90° C. for 4 h. After cooling to room temperature, the volatiles were removed in vacuo, and the resulting residue purified by flash chromatography on 12 g of silica gel (50→100% gradient of EtOAc in hexanes). The pure fractions were collected, and the solvent removed in vacuo to afford the title compound (139 mg, 20% yield). HPLC retention time=2.96 minutes. $^1$H NMR (400 MHz, CDCl$_3$) δ 8.55 (d, J=2.0, 1H), 8.19 (d, J=2.0, 1H), 8.12 (d, J=2.4, 1H), 7.98 (d, J=2.0, 1H), 7.90 (dd, J=2.4, 8.4, 1H), 7.58 (d, J=8.4, 1H), 6.62 (d, J=2.0, 1H), 4.41 (q, J=7.2, 2H), 1.40 (t, J=7.2, 3H). MS (ES) [M+H]$^+$ expected 577.0, found 577.0.

General Procedure J: Aminolysis of Triazole Esters

To a vial containing ethyl 5-(3-(4-chloro-3-(trifluoromethyl)benzenesulfonamido)-5-chloropyridin-2-yl)-4-(isoxazol-3-yl)-4H-1,2,4-triazole-3-carboxylate (60 mg, 0.1 mmol) was added THF (1 mL) and the appropriate amine (20 mmol). The solution was maintained for 18 h at room temperature. EtOAc (30 mL) was added. The organic phase was washed with water (2×10 mL) and dried over Na$_2$SO$_4$. The volatiles were removed in vacuo, and the resulting residue purified by flash chromatography on 12 g of silica gel (50→100% gradient of EtOAc in hexanes). The pure fractions were collected, and the solvent removed in vacuo to afford the desired compound.

5-(3-(4-chloro-3-trifluoromethyl)benzenesulfonamido)-5-chloropyridin-2-yl)-4-(isoxazol-3-yl)-4H-1,2,4-triazole-3-carboxamide

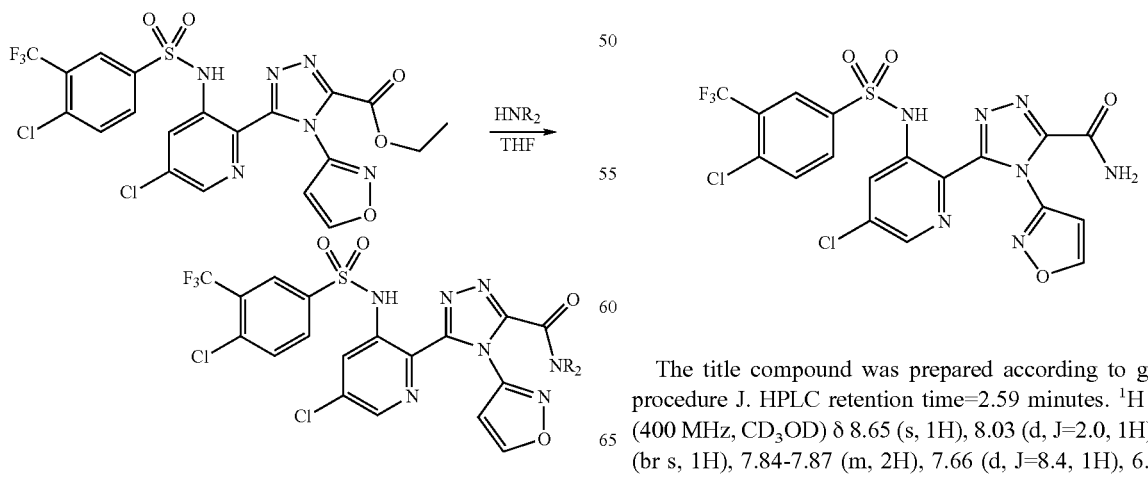

The title compound was prepared according to general procedure J. HPLC retention time=2.59 minutes. $^1$H NMR (400 MHz, CD$_3$OD) δ 8.65 (s, 1H), 8.03 (d, J=2.0, 1H), 7.98 (br s, 1H), 7.84-7.87 (m, 2H), 7.66 (d, J=8.4, 1H), 6.75 (d, J=2.0, 1H). MS (ES) [M+H]$^+$ expected 548.0, found 547.9.

5-(3-(4-chloro-3-(trifluoromethyl)benzenesulfonamido)-5-chloropyridin-2-yl)-4-(isoxazol-3-yl)-N,N-dimethyl-4H-1,2,4-triazole-3-carboxamide

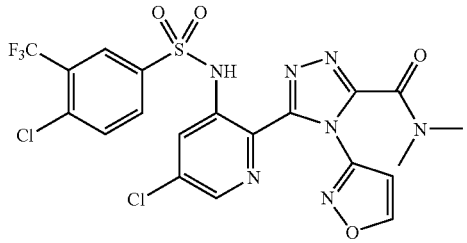

The title compound was prepared according to general procedure J. HPLC retention time=2.79 minutes. $^1$H NMR (400 MHz, CDCl$_3$) δ 8.46 (br s, 1H), 8.18 (br s, 1H), 8.12 (br s, 1H), 7.93-7.95 (m, 2H), 7.59 (d, J=8.4, 1H), 6.60 (br s, 1H), 3.34 (s, 3H), 3.06 (s, 3H). MS (ES) [M+H]$^+$ expected 576.0, found 576.0.

5-(3-(4-chloro-3-(trifluoromethyl)benzenesulfonamido)-5-chloropyridin-2-yl)-4-(isoxazol-3-yl)-N-ethyl-4H-1,2,4-triazole-3-carboxamide

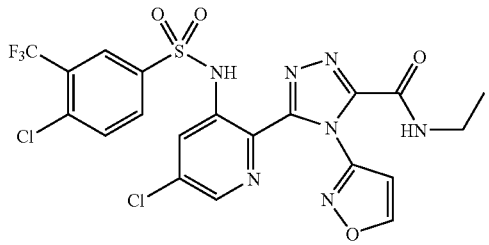

The title compound was prepared according to general procedure J. HPLC retention time=2.77 minutes. $^1$H NMR (400 MHz, CDCl$_3$) δ 8.52 (s, 1H), 8.14-8.15 (m, 2H), 7.98 (s, 1H), 7.85 (d, J=8.4, 1H), 7.58 (d, J=8.4, 1H), 6.43-6.51 (m, 1H), 3.41-3.48 (m, 2H), 1.24-1.28 (m, 3H). MS (ES) [M+H]$^+$ expected 576.0, found 576.0.

(5-(3-(4-chloro-3-(trifluoromethyl)benzenesulfonamido)-5-chloropyridin-2-yl)-4-(isoxazol-3-yl)-4H-1,2,4-triazol-3-yl)(pyrolidin-1-yl)methanone

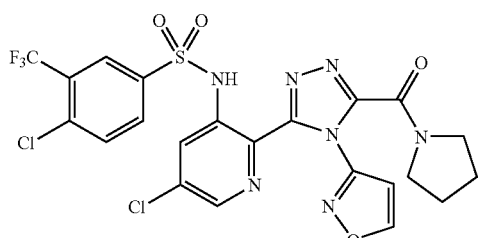

The title compound was prepared according to general procedure J. HPLC retention time=2.91 minutes. $^1$H NMR (400 MHz, CDCl$_3$) δ 8.48 (s, 1H), 8.14-8.19 (m, 2H), 7.92-7.97 (m, 2H), 7.58-7.60 (m, 1H), 6.65-6.66 (m, 1H), 3.96-4.02 (m, 2H), 3.54-3.60 (m, 2H), 1.96-2.04 (m, 4H). MS (ES) [M+H]$^+$ expected 602.0, found 602.0.

(5-(3-(4-chloro-3-(fluoromethyl)sulfonamido)-5-chloropyridin-2-yl)-4-isoxazol-3-yl)-4H-1,2,4-triazol-3-yl)(morpholino)methanone

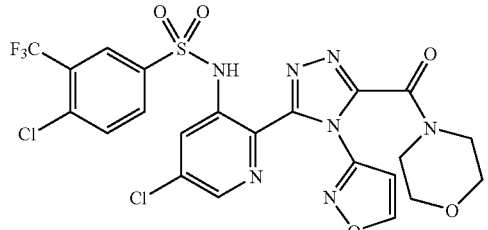

The title compound was prepared according to general procedure J. HPLC retention time=2.54 minutes. $^1$H NMR (400 MHz, CDCl$_3$) δ 8.49 (d, J=2.0, 1H), 8.17-8.20 (m, 2H), 7.95-8.00 (m, 2H), 7.57-7.62 (m, 1H), 6.63-6.64 (m, 1H), 3.69-3.96 (m, 4H). MS (ES) [M+H]$^+$ expected 618.0, found 618.0.

5-(3-(4-chloro-3-(trifluoromethyl)benzenesulfonamido)-5-chloropyridin-2-yl)-4-(isoxazol-3-yl)-N-ethyl-4H-1,2,4-triazole-3-carboxamide

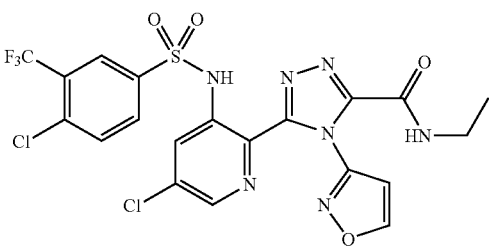

The title compound was prepared according to general procedure J. HPLC retention time=2.92 minutes. MS (ES) [M+H]$^+$ expected 590.0, found 590.0. $^1$H NMR (400 MHz, CDCl$_3$) δ 8.52 (s, 1H), 8.14-8.16 (m, 2H), 7.99 (s, 1H), 7.85 (d, J=8.0, 1H), 7.58 (d, J=8.0, 1H), 6.51-6.66 (m, 1H), 4.11-4.19 (m, 1H), 1.27-1.29 (m, 6H).

5-(3-(4-chloro-3-(trifluoromethyl)benzenesulfonamido)-5-chloropyridin-2-yl)-4-(isoxazol-3-yl)-N-methyl-N-ethyl-4H-1,2,4-triazole-3-carboxamide

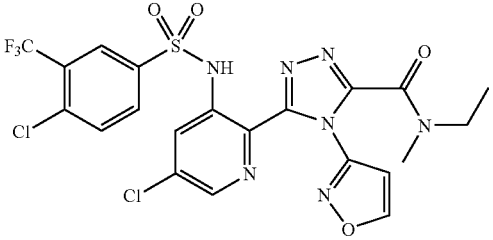

The title compound was prepared according to general procedure J. HPLC retention time=2.87 minutes. $^1$H NMR (400 MHz, CDCl$_3$) δ 8.47-8.48 (m, 1H), 8.15-8.21 (m, 2H), 7.95-7.99 (m, 2H), 7.61 (d, J=8.4, 1H), 6.61-6.62 (m, 1H), 3.70 and 3.51 (q, J=7.0, 2H), 3.31 and 3.03 (s, 3H), 1.36 and 1.18 (t, J=7.0, 3H), MS (ES) [M+H]$^+$ expected 590.0, found 590.0.

N-(4-chloro-3-(trifluoromethyl)benzenesulfona-mido)-5-chloro-2-(4-(isoxazol-3-yl)-5-(methoxym-ethyl)-4H-1,2,4-triazol-3-yl)pyridin-3-amine

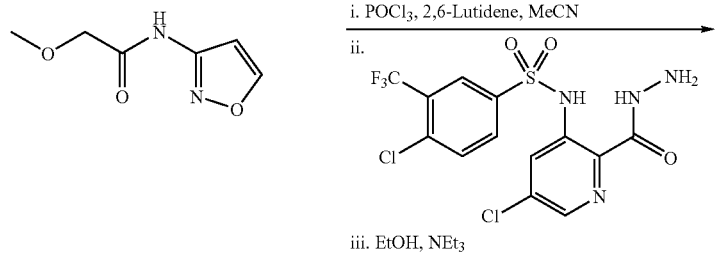

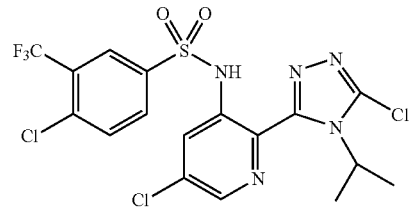

To a vial equipped with a teflon coated septum and a nitrogen inlet were added N-(isoxazol-3-yl)-2-methoxyac-etamide (330 mg, 2.1 mmol), MeCN (4 mL) and 2,6-lutidine (0.5 mL, 4.3 mmol). The vial was cooled to 0° C. POCl$_3$ (0.25 mL, 2.7 mmol) was added, and the solution maintained at 0° C. for 30 min. The solution was then warmed to 80° C. for 1 h. After cooling to room temperature, solid 4-chloro-N-(5-chloro-2-(hydrazinecarbonyl)pyridine-3-yl)-3-(trifluorom-ethyl)benzenesulfonamide (430 mg, 1.0 mmol) was added, and the reaction heated to 80° C. for 1 h. The volatiles were removed in vacuo. Ethanol (9 mL) and triethylamine (1 mL) were added, and the solution heated to 90° C. for 4 h. After cooling to room temperature, the volatiles were removed in vacuo, and the resulting residue purified by flash chromatog-raphy on 12 g of silica gel (0→40% gradient of MeOH in DCM). The pure fractions were collected, and the solvent removed in vacuo to afford the title compound (55 mg, 10% yield). HPLC retention time=2.82 minutes. MS (ES) [M+H]$^+$ expected 549.0, found 549.0.

N-(4-chloro-3-(trifluoromethyl)benzenesulfona-mido)-5-chloro-2-(5-chloro-4-isopropyl-4H-1,2,4-triazol-3-yl)pyridin-3-amine To a vial equipped with a teflon coated septum and a nitrogen inlet were added 4-chloro-N-[5-chloro-2-(4-isopro-pyl-4H-1,2,4-triazol-3-yl)pyridin-3-yl]-3-(trifluoromethyl) benzenesulfonamide (50 mg, 0.10 mmol) and DCM (0.2 mL). The reaction mixture was cooled to 5° C. N-Chlorosuccinim-ide (16 mg, 0.12 mmol) was added, and the reaction warmed to room temperature. After 48 h, EtOAc (10 mL) was added. The solution was stirred with 5% aq. NaHSO$_3$ solution (10 mL) for 15 min. The layers were then partitioned. The organic phase was washed with water (1×5 mL) and dried over Na$_2$SO$_4$. The volatiles were removed in vacuo. The resulting residue was purified by preparative HPLC (20→95% gradi-ent of MeCN—H$_2$O with 0.1% TFA) and the pure fractions lyophilized to afford the title compound (10 mg, 19% yield). HPLC retention time=3.13 minutes. $^1$H NMR (400 MHz, CDCl$_3$) δ 8.47 (s, 1H), 8.31 (s, 1H), 8.11 (d, J=2.0, 1H), 7.94 (dd, J=2.0, 8.0, 1H), 7.57 (d, J=8.0, 1H), 5.57 (sept, J=6.4, 1H), 1.52 (d, J=6.4, 6H). MS (ES) [M+H]$^+$ expected 514.0, found 513.9.

4-Chloro-N-{5-chloro-2-[4-(2-hydroxy-1-methyl-ethyl)-4H-[1,2,4]triazol-3-yl]-pyridin-3-yl}-3-trif-luoromethyl-benzenesulfonamide

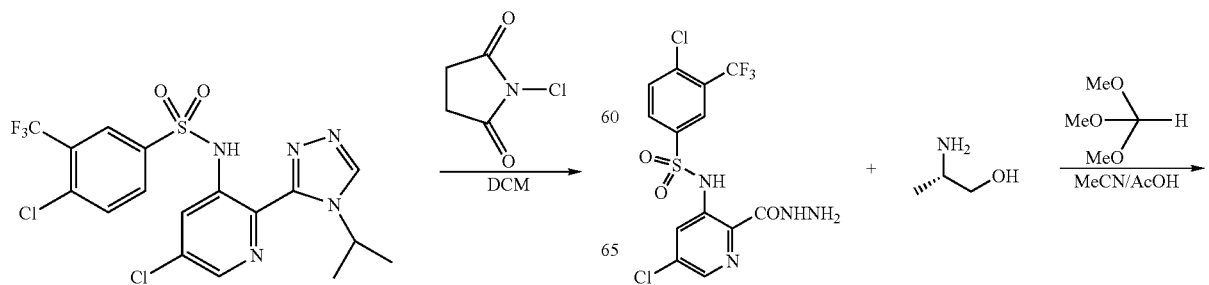

-continued

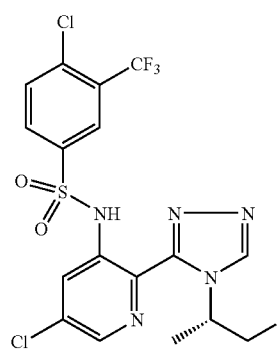

The title compound was prepared according to general Method B. ¹H NMR (400 MHz, DMSO-d⁶) δ 8.90 (s, 1H), 8.51 (m, 1H), 8.05 (m, 1H), 7.99 (m, 2H), 7.85 (d, 1H), 5.19 (m, 1H), 4.98 (brs., 1H, —OH), 3.70 (dd, 1H), 3.40 (dd, 1H), 1.30 (s, 3H). MS (ES) [M+H]⁺ expected 496.0, found 495.9.

4-Chloro-N-{5-chloro-2-[4-(2-dimethylamino-1-methyl-ethyl)-4H-[1,2,4]-triazol-3-yl]-pyridin-3-yl}-3-trifluoromethyl-benzenesulfonamide

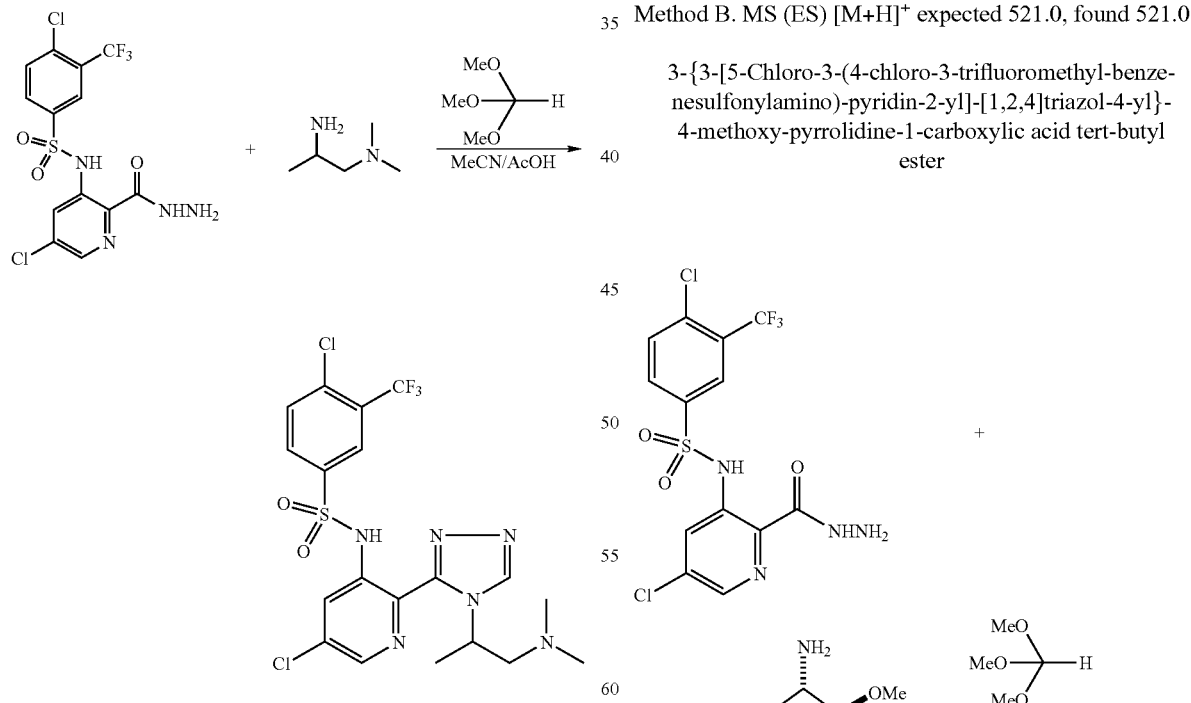

The title compound was prepared according to general Method B. ¹H NMR (400 MHz, CD₃OD) δ 8.95 (s, 1H), 8.52 (d, 1H), 8.25 (d, 1H), 8.10 (m, 1H), 8.00 (dd, 1H), 7.74 (d, 1H), 6.11 (m, 1H), 3.86 (dd, 1H), 3.58 (d, 1H), 2.98 (s, 6H), 1.47 (d, 3H). MS (ES) [M+H]⁺ expected 523.0, found 523.0.

4-Chloro-N-[5-chloro-2-(4-piperidin-4-yl-4H-[1,2,4]triazol-3-yl)-pyridin-3-yl]-3-trifluoromethyl-benzenesulfonamide

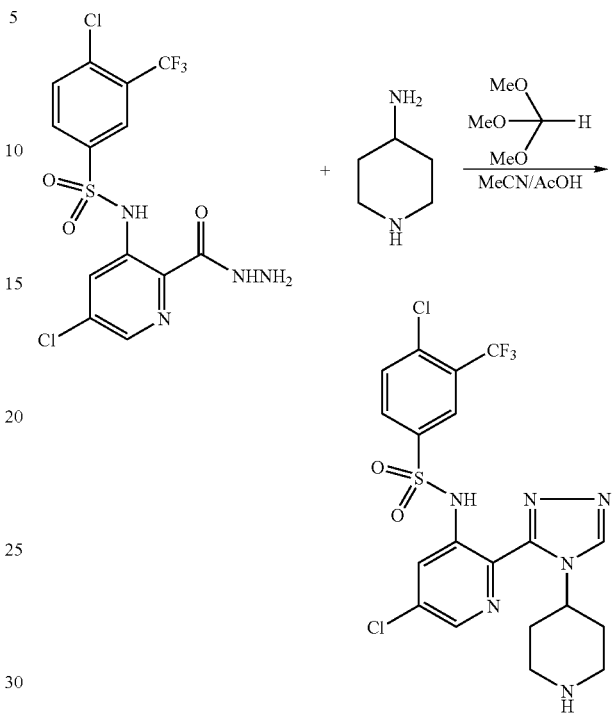

The title compound was prepared according to general Method B. MS (ES) [M+H]⁺ expected 521.0, found 521.0.

3-{3-[5-Chloro-3-(4-chloro-3-trifluoromethyl-benzenesulfonylamino)-pyridin-2-yl]-[1,2,4]triazol-4-yl}-4-methoxy-pyrrolidine-1-carboxylic acid tert-butyl ester Tetrahedron: Assymm., 12(21), 2001, 2989-2997

-continued

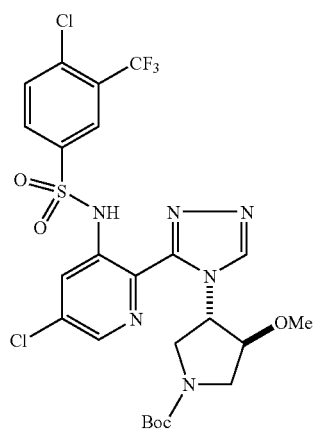

The title compound was prepared according to general Method B. MS (ES) [M+H]⁺ expected 637.0, found 637.0.

4-Chloro-N-{5-chloro-2-[4-(4-methoxy-pyrrolidin-3-yl)-4H-[1,2,4]triazol-3-yl]-pyridin-3-yl}-3-trifluoromethyl-benzenesulfonamide

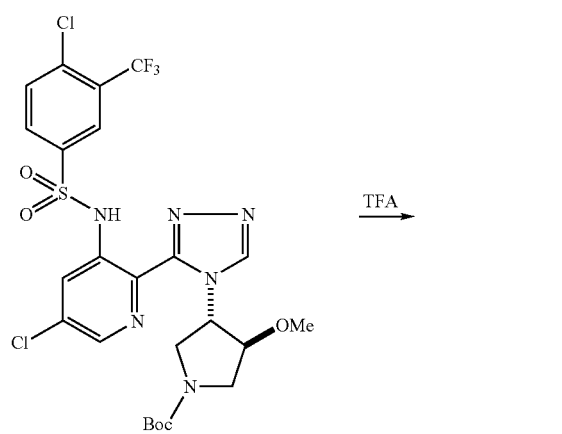

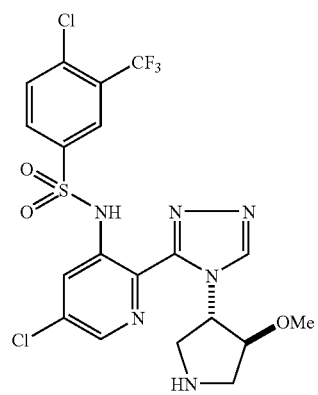

To 3-{3-[5-chloro-3-(4-chloro-3-trifluoromethyl-benzenesulfonylamino)-pyridin-2-yl]-[1,2,4]triazol-4-yl}-4-methoxy-pyrrolidine-1-carboxylic acid tert-butyl ester (71 mg, 0.11 mmol) was added 1:1 mixture of TFA-CH₂Cl₂ (2 mL) at room temperature and stirred for 2 h. Solvents were evaporated, 1:1 mixture of CH₃CN—H₂O (5 mL) and lyophilized to obtain 4-chloro-N-{5-chloro-2-[4-(4-methoxy-pyrrolidin-3-yl)-4H-[1,2,4]triazol-3-yl]-pyridin-3-yl}-3-trifluoromethyl-benzenesulfonamide as a white solid in quantitative yield. MS (ES) [M+H]⁺ expected 537.0, found 537.0.

4-Chloro-N-{5-chloro-2-[5-isopropyl-4-(1H-pyrazol-3-yl)-4H-[1,2,4]triazol-3-yl]pyridin-3-yl}-3-trifluoromethyl-benzenesulfonamide

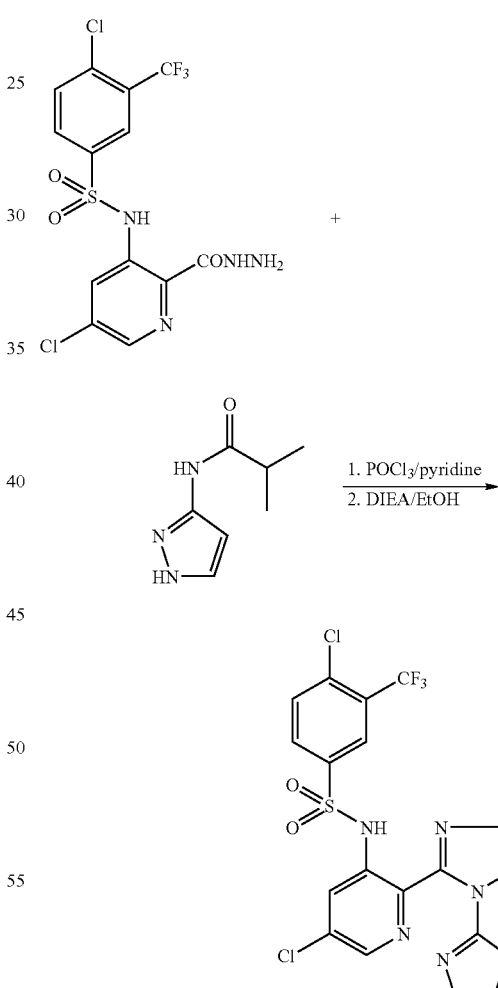

The title compound was prepared according to general procedure C. ¹H NMR (400 MHz, CDCl₃) δ 8.32 (m, 2H), 8.05 (s, 1H), 7.95 (m, 1H), 7.62 (m, 1H), 7.58 (m, 1H), 6.28 (s, 1H), 2.90 (m, 1H), 1.28 (m, 6H). MS (ES) [M+H]⁺ expected 546.0, found 545.9.

4-Chloro-N-{5-chloro-2-[5-cyclopropyl-4-(1H-pyrazol-3-yl)-4H-[1,2,4]-triazol-3-yl]-pyridin-3-yl}-3-trifluoromethyl-benzenesulfonamide

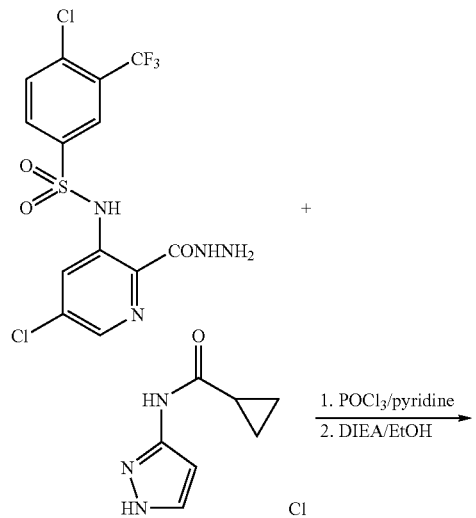

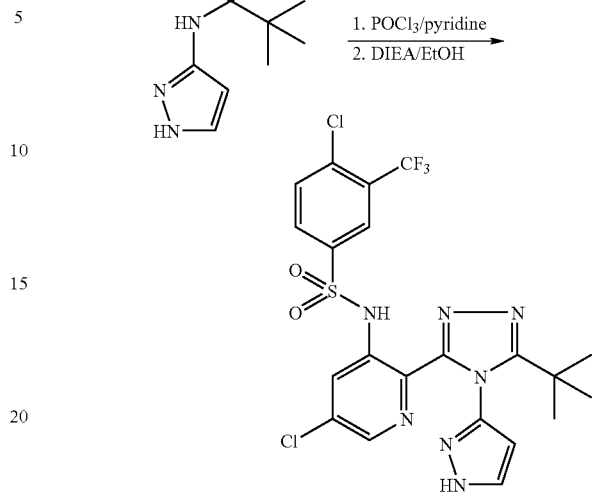

The title compound was prepared according to general procedure C. $^1$H NMR (400 MHz, CDCl$_3$) δ 8.15 (m, 2H), 7.95 (m, 2H), 7.70 (s, 1H), 7.58 (d, 1H), 6.28 (s, 1H), 3.05 (m, 1H), 1.28 (m, 4H). MS (ES) [M+H]$^+$ expected 544.0, found 543.9.

N-{2-[5-tert-Butyl-4-(1H-pyrazol-3-yl)-4H-[1,2,4]triazol-3-yl]-5-chloro-pyridin-3-yl}-4-chloro-3-trifluoromethyl-benzenesulfonamide

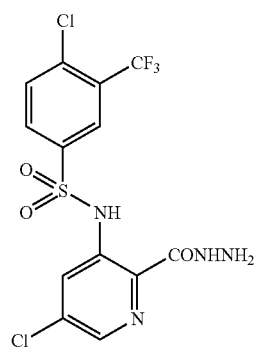

The title compound was prepared according to general procedure C. MS (ES) [M+H]$^+$ expected 560.0, found 560.0.

5-[3-(4-Chloro-3-trifluoromethyl-benzenesulfonylamino)-5-methyl-pyridin-2-yl]-4-isoxazol-3-yl-4H-[1,2,4]triazole-3-carboxylic acid ethyl ester

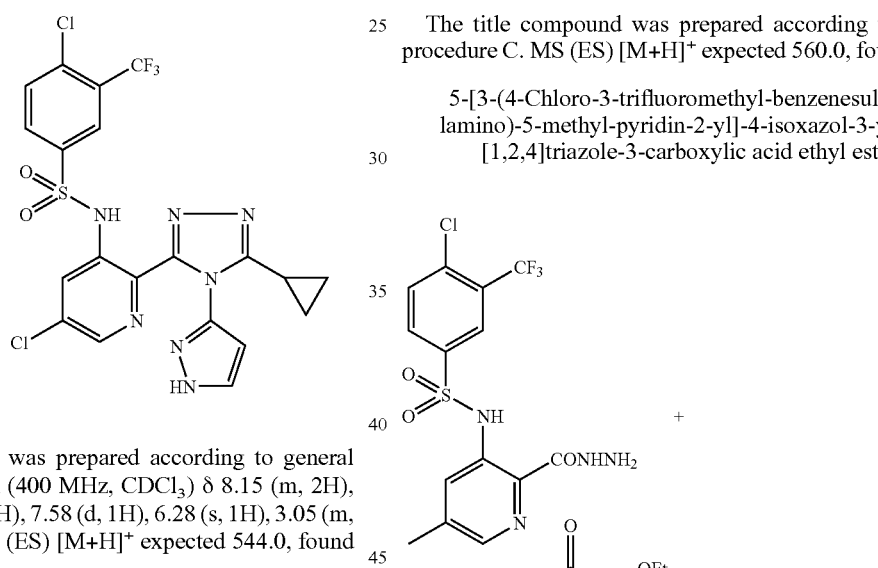

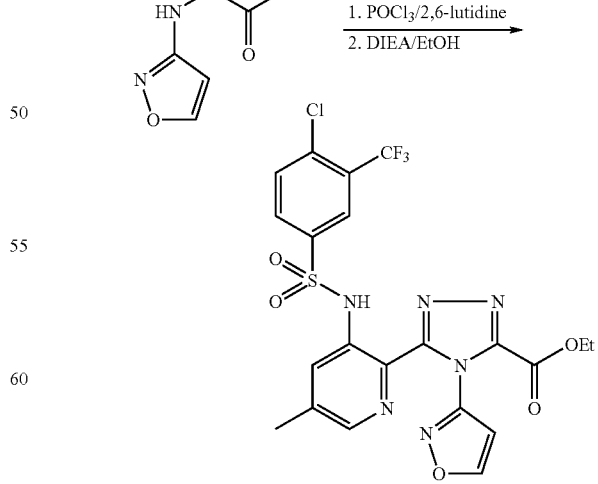

The title compound was prepared according to general procedure C. MS (ES) [M+H]$^+$ expected 557.0, found 556.9.

5-[3-(4-Chloro-3-trifluoromethyl-benzenesulfonylamino)-5-methyl-pyridin-2-yl]-4-isoxazol-3-yl-4H-[1,2,4]-triazole-3-carboxylic acid amide

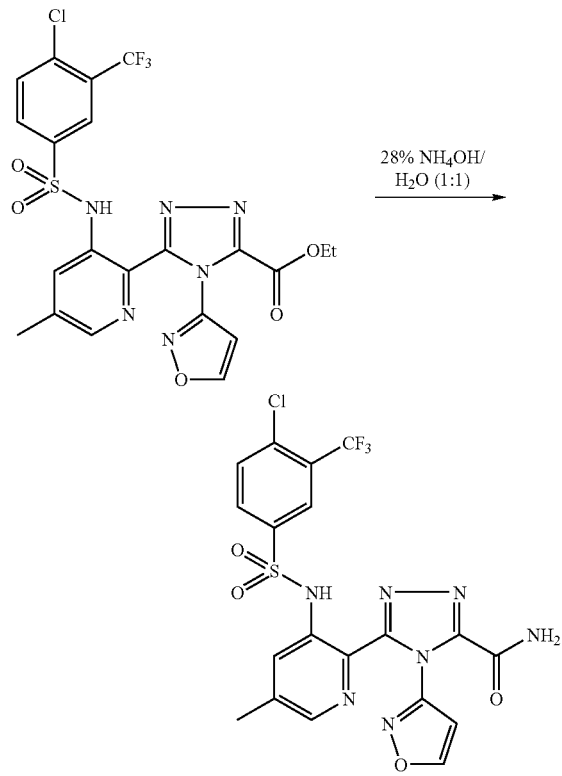

The title compound was prepared according to general procedure J. $^1$H NMR (400 MHz, CDCl$_3$) δ 8.50 (s, 1H), 8.08 (s, 1H), 7.91 (m, 2H), 7.80 (d, 1H), 7.55 (d, 1H), 6.61 (s, 1H), 2.34 (s, 3H). MS (ES) [M+H]$^+$ expected 528.0, found 528.0.

General Method K. 4-Chloro-N-[5-chloro-3-E4-methyl-3-(trifluoromethyl)phenylsulfonamido)pyridin-2-yl)-4H-1,2,4-triazole-3-carboxamide

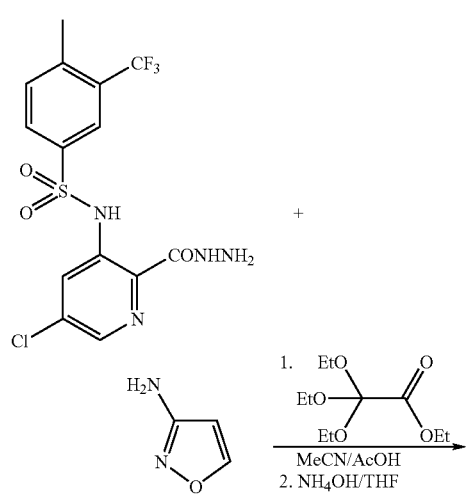

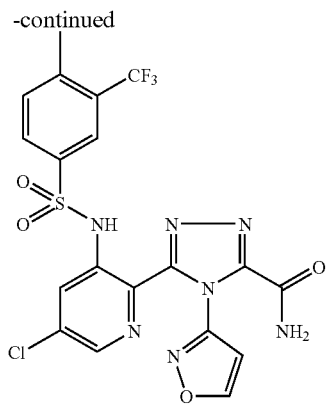

A 35 mL scintillation vial was charged with N-(4-chloro-2-hydrazinecarbonyl)pyridine-3-yl)-4-methyl-3-(trifluoromethyl)benzenesulfonamide (MS, 409 [M+H]$^+$) (205 mg, 0.5 mmol), ethyl triethoxyacetate (*J. Am. Chem. Soc.* 1951, 73, 5168-5169.) (165 mg, 0.75 mmol), and anhydrous MeCN (3 mL). The resultant mixture was heated to 65° C. and stirred for 1 h. After cooling to room temperature, 3-aminoisoxazole (85 mg, 1 mmol) was added followed by AcOH (0.2 mL), and mixture was heated to 65° C. for 30 min and then to 135° C. and stirred for 2 h. After cooling to room temperature, the reaction mixture was concentrated under reduced pressure. The residue was purified through automated normal-phase chromatography (10% to 100% gradient of EtOAc-Hexane) and dried (Lyophilizer) to afford the desired triazole ester (MS (ES) [M+H]$^+$ expected 557.0, found 557.0), which was used directly for the next step.

To the above ester in THF (2 mL) was added aqueous ammonia (28%, 1 mL), and the resultant mixture was stirred at room temperature for 3 h. The reaction mixture was diluted with 1N HCl and extracted EtOAc (50 mL×2), the combined organic layer was concentrated under reduced pressure. The residue was purified through automated normal-phase chromatography (10% to 100% gradient of EtOAc-Hexane) and dried (Lyophilizer) to afford the title compound. $^1$H NMR (400 MHz, d$^6$-DMSO) δ 11.0 (br, 1H), 8.98 (d, 1H), 8.60 (s, 1H), 8.27 (s, 1H), 8.08 (s, 1H), 7.95 (m, 2H), 7.87 (s, 1H), 7.61 (d, 1H), 6.78 (d, 1H), 2.49 (s, 3H). MS (ES) [M+H]$^+$ expected 528.0, found 528.0.

5-(5-Chloro-3-(3,4-dichlorophenylsulfonamido)pyridin-2-yl)-4-(isoxazol-3-yl)-4H-1,2,4-triazole-3-carboxamide

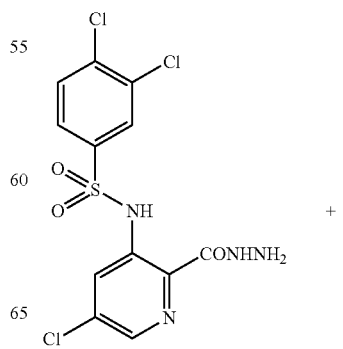

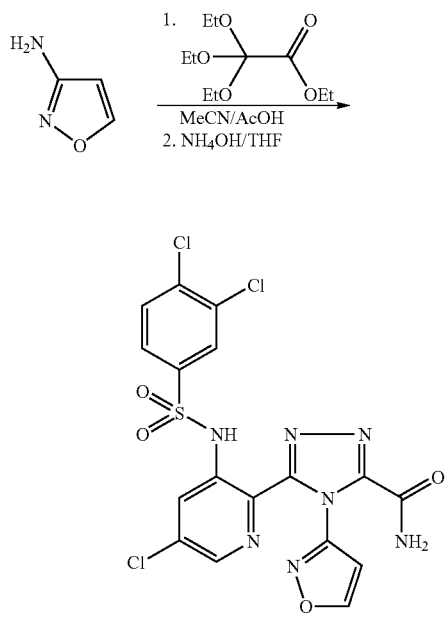

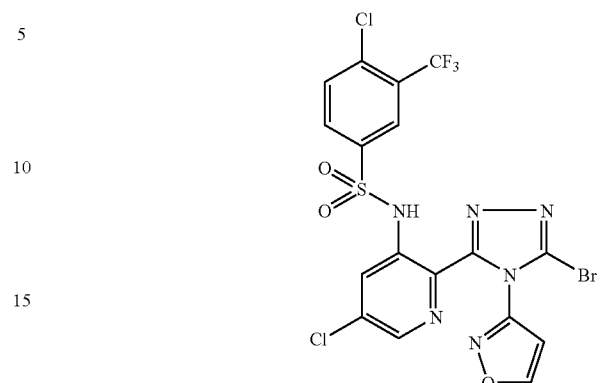

The title compound was prepared by procedure analogous to that described in Example [00458] using 3,4-dichloro-N-(4-chloro-2-hydrazinecarbonyl)pyridine-3-yl)benzenesulfonamide (200 mg, 0.5 mmol) (MS, 396.9 [M+H]$^+$), ethyl triethoxyacetate (*J. Am. Chem. Soc.* 1951, 73, 5168-5169.) (165 mg, 0.75 mmol), and 3-aminoisoxazole (85 mg, 1 mmol). $^1$H NMR (400 MHz, d$^6$-DMSO) δ 8.82 (d, 1H), 8.47 (s, 1H), 7.79 (s, 1H), 7.67 (d, 1H), 7.59 (s, 1H), 7.56 (s, 1H), 7.40 (dd, 1H), 7.23 (d, 1H), 6.64 (d, 1H). MS (ES) [M+H]$^+$ expected 514.0, found 513.9.

N-[2-(5-bromo-4-(isoxazol-3-yl)-4H-1,2,4-triazol-3-yl)-5-chloropyridin-3-yl]-4-chloro-3-(trifluoromethyl)benzenesulfonamide

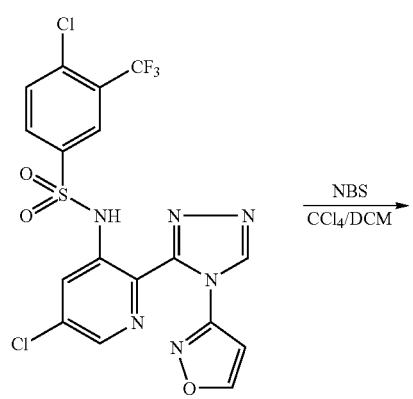

4-Chloro-N-[5-chloro-2-(4-(isoxazol-3-yl)-4H-1,2,4-triazol-3-yl)pyridin-3-yl]-3-(trifluoromethyl)benzenesulfonamide (80 mg) in CCl4/DCM (3 mL/1 mL) was charged with NBS (30 mg). The resulting mixture was stirred at room temperature for 6 h. The reaction mixture was diluted with sat NaHCO3 and extracted EtOAc (50 mL×2), the combined organic layer was concentrated under reduced pressure. The residue was purified through automated normal-phase chromatography (10% to 100% gradient of EtOAc-Hexane), and followed by preparative HPLC (10% to 90% gradient of MeCN-water) and dried (Lyophilizer) to afford the title compound. $^1$H NMR (400 MHz, CDCl$_3$) δ 11.6 (br, 1H), 8.60 (d, 1H), 8.46 (s, 1H), 8.27 (s, 1H), 8.19 (d, 1H), 7.98 (dd, 1H), 7.62 (d, 1H), 6.63 (d, 1H). MS (ES) [M+H]$^+$ expected 584.0, found 584.0.

N-[2-(5-bromo-4-isopropyl-4H-1,2,4-triazol-3-yl)-5-chloropyridin-3-yl]-4-chloro-3-(trifluoromethyl)benzenesulfonamide

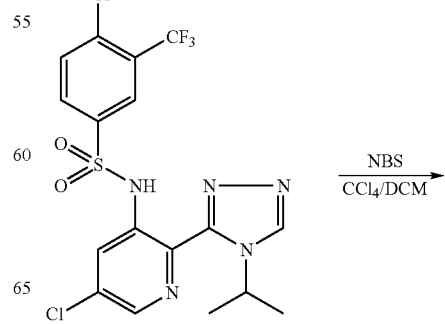

-continued

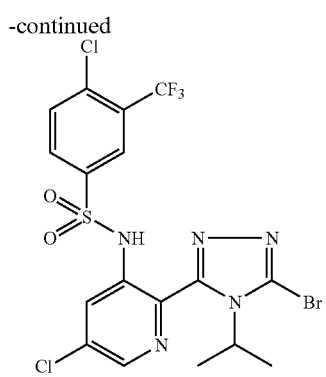

The title compound was prepared by procedure analogous to that described in Example [00463] using 4-Chloro-N-[5-chloro-2-(4-isopropyl-4H-1,2,4-triazol-3-yl)pyridin-3-yl]-3-(trifluoromethyl)benzenesulfonamide. $^1$H NMR (400 MHz, CDCl$_3$) 8.35 (s, 1H), 8.26 (s, 1H), 8.12 (d, 1H), 7.92 (dd, 1H), 7.56 (d. 1H), 5.50 (m, 1H), 1.48 (d, 6H). MS (ES) [M+H]$^+$ expected 559.9, found 559.9.

N-[2-(4-(4-bromo-1H-pyrazole-3-yl)-4H-1,2,4-triazol-3-yl)-5-chloropyridin-3-yl]-3,4-dichlorobenzenesulfonamide

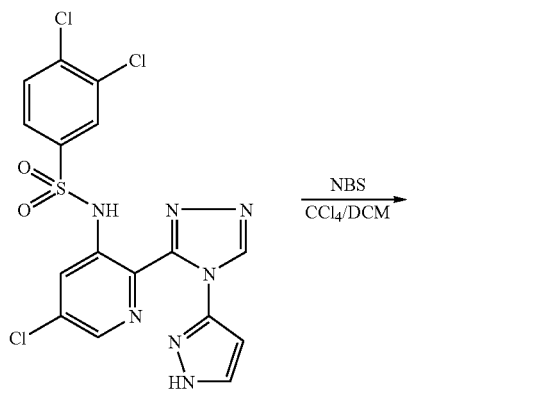

The title compound was prepared by procedure analogous to that described in Example [00463] using N-[2-(4-(1H-pyrazol-3-yl)-4H-1,2,4-triazol-3-yl)-5-chloropyridin-3-yl]-3,4-dichlorobenzenesulfonamide. $^1$H NMR (400 MHz, CDCl$_3$) 11.67 (br, 1H), 10.20 (br, 1H), 8.27 (s, 1H), 8.16 (d, t H), 7.95 (d, 1H), 7.90 (d, 1H), 7.68 (dd, 2H), 7.46 (d, 1H). MS (ES) [M+H]$^+$ expected 549.9, found 549.9.

N-[2-(5-bromo-4-(4-bromo-1H-pyrazole-3-yl)-4H-1,2,4-triazol-3-yl)-5-chloropyridin-3-yl]-3,4-dichlorobenzenesulfonamide

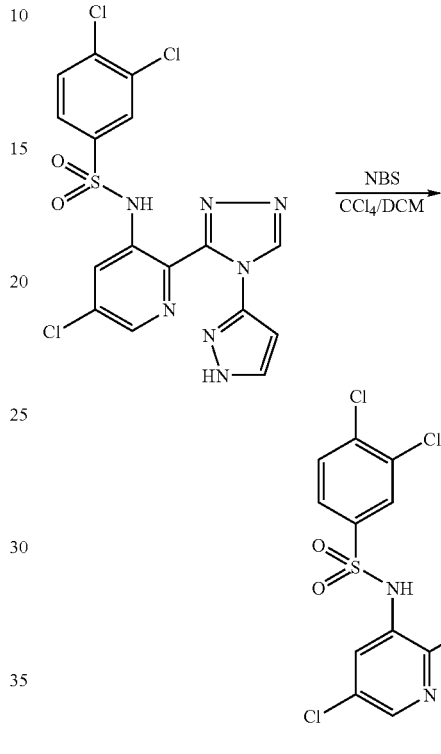

The same experiment described in Example [00467] also produced the title compound. $^1$H NMR (400 MHz, CDCl$_3$) 11.60 (br, 1H), 10.25 (br, 1H), 8.30 (s, 1H), 8.22 (s, 1H), 7.72 (d, 1H), 7.68 (dd, 2H), 7.49 (d, 1H). MS (ES) [M+H]$^+$ expected 629.8, found 629.8.

N-[2-(4-(4-bromo-1H-pyrazole-3-yl)-5-methyl-4H-1,2,4-triazol-3-yl)-5-chloropyridin-3-yl]-4-chloro-3-(trifluoromethyl)benzenesulfonamide

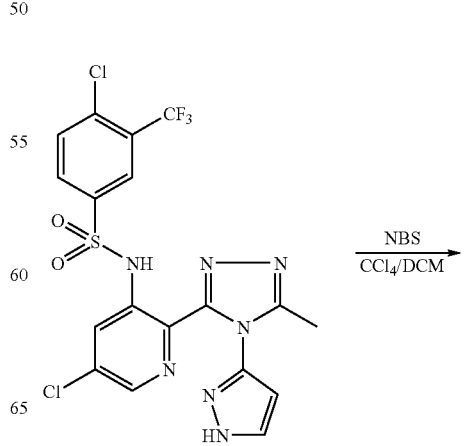

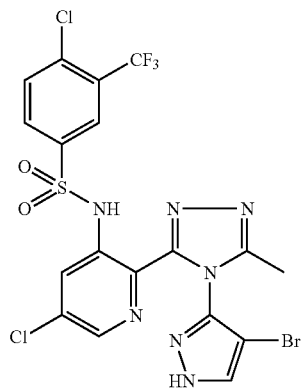

The title compound was prepared by procedure analogous to that described in Example [00463] using 4-chloro-N-[5-Chloro-2-(5-methyl-4-(1H-pyrazol-3-yl)-4H-1,2,4-triazol-3-yl)pyridin-3-yl]-3-(trifluoromethyl)benzenesulfonamide (MS, 518.0 [M+H]$^+$). $^1$H NMR (400 MHz, CDCl$_3$) 8.12 (m, 2H), 7.94 (dd, 1H), 7.88 (d, 1H), 7.72 (s, 1H), 7.56 (d, 1H), 2.40 (s, 3H). MS (ES) [M+H]$^+$ expected 597.9, found 597.9.

N-[2-(4-(1H-pyrazol-3-yl)-5-(trifluoromethyl)-4H-1,2,4-triazol-3-yl)-5-chloropyridin-3-yl]-4-chloro-3-trifluoromethyl)benzenesulfonamide

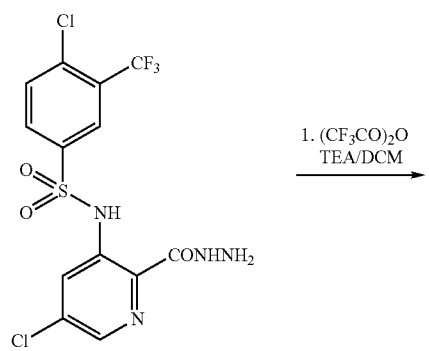

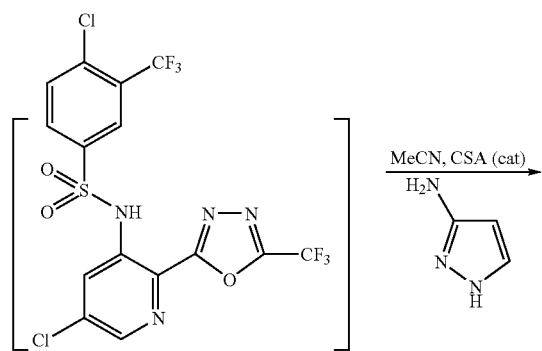

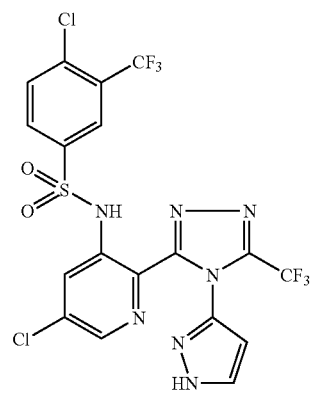

To a solution of 4-dichloro-N-(4-chloro-2-(hydrazinecarbonyl)pyridine-3-yl)-3-(trifluoromethyl)benzenesulfonamide (210 mg, 0.5 mmol) in DCM (10 mL) was added TEA (0.2 mL), followed by trifluoroacetic acid anhydride (210 mg, 1 mmol).

The resulting mixture was stirred at room temperature for 6 h. The reaction mixture was diluted with sat NaHCO$_3$ and extracted DCM (50 mL×2), the combined organic layer was concentrated under reduced pressure. The residue was purified through automated normal-phase chromatography (10% to 100% gradient of EtOAc-Hexane) to afford the intermediate oxodiazole ((MS (ES) [M+H]$^+$ expected 506.9, found 506.9) which was used directly for the next step.

A 35 mL scintillation vial was charged with the above oxodiazole (110 mg, 0.2 mmol), anhydrous MeCN (3 mL), 3-aminopyrazole (45 mg, 0.5 mmol) was added followed by CSA (10 mg, cat), and mixture was heated to 135° C. and stirred for 2 h. After cooling to room temperature, the reaction mixture was concentrated under reduced pressure. The residue was purified through automated normal-phase chromatography (10% to 100% gradient of EtOAc-Hexane) and dried in vacuo to afford the title compound. $^1$H NMR (400 MHz, CDCl$_3$) δ 10.15 (br, 1H), 8.18 (d, 1H), 8.10 (d, 1H), 7.96 (d, 1H), 7.90 (dd, 1H), 7.70 (d, 1H), 7.57 (d, 1H), 6.40 (d, 1H). (MS (ES) [M+H]$^+$ expected 572.0, found 572.0).

N-[2-(4-(1H-pyrazol-3-yl)-4H-1,2,4-triazol-3-yl)-5-chloropyridin-3-yl]-3,4-dichlorobenzenesulfonamide

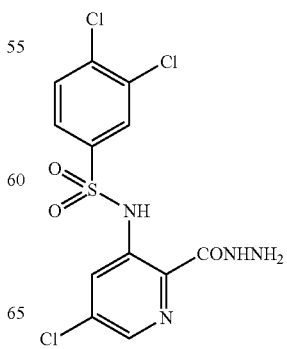

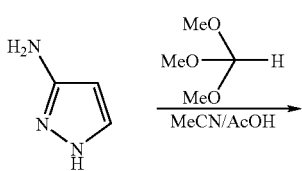

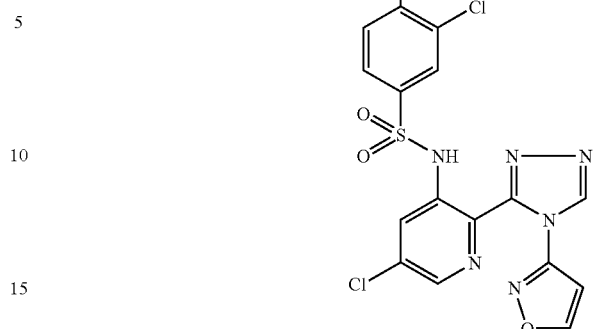

The titled compound was prepared according to general Method B using 3,4-dichloro-N-(4-chloro-2-hydrazinecarbonyl)pyridine-3-yl)benzenesulfonamide and 3-aminoisoxazole. MS (ES) (M+H)$^+$ expected 471.0, found 470.9.

N-[2-(4-(1H-pyrazol-3-yl)-4H-1,2,4-triazol-3-yl)-5-bromopyridin-3-yl]-4-chloro-3-(trifluoromethyl)benzenesulfonamide

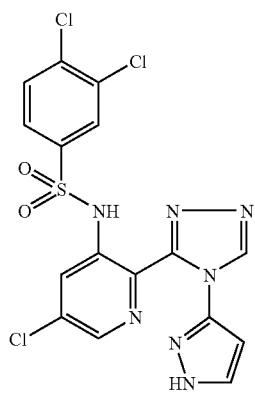

The titled compound was prepared according to general Method C described in Example 5 using 3,4-dichloro-N-(4-chloro-2-hydrazinecarbonyl)pyridine-3-yl)benzenesulfonamide and 3-aminopyrazole: $^1$H NMR (400 MHz, CDCl$_3$) δ 8.37 (s, 1H), 8.12 (d 1H), 8.02 (d, 1H), 7.88 (d, 1H), 7.65 (d, 1H), 7.62 (d, 1H), 7.46 (d, 1H), 6.25 (d, 1H). MS (ES) [M+H$^+$ expected 470.0, found 470.0.

3,4-dichloro-N-(5-chloro-2-(4-(isoxazol-3-yl)-4H-1,2,4-triazol-3-yl)pyridin-3-yl]-benzenesulfonamide

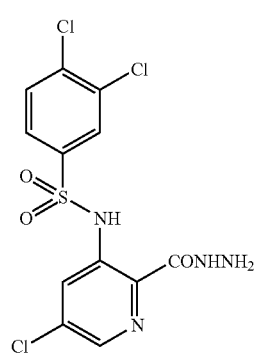

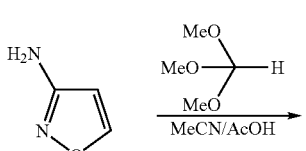

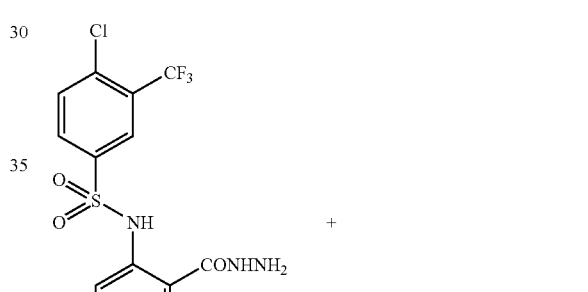

The titled compound was prepared according to general Method B using 3,4-dichloro-N-(4-bromo-2-hydrazinecarbonyl)pyridine-3-yl)benzenesulfonamide (MS, 474.9

(M+H)) and 3-aminopyrazole: ¹H NMR (400 MHz, CDCl₃) δ 8.34 (s, 1H), 8.30 (d, 1H), 8.12 (d, 1H), 8.08 (d, 1H), 7.90 (dd, 1H), 7.61 (d, 1H), 7.54 (d, 1H), 6.25 (d, 1H). MS (ES) [M+H]⁺ expected 549.9, found 549.9.

N-(5-bromo-2-(4-(isoxazol-3-yl)-4H-1,2,4-triazol-3-yl)pyridin-3-yl]-4-chloro-3-(trifluoromethyl)benzenesulfonamide

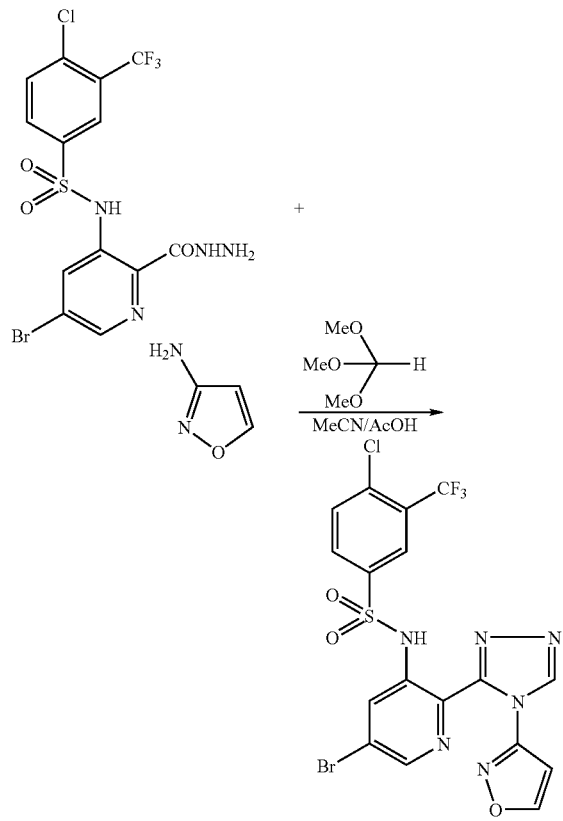

The titled compound was prepared according to general Method B using 3,4-dichloro-N-(4-bromo-2-hydrazinecarbonyl)pyridin-3-yl)benzenesulfonamide and 3-aminoisoxazole. MS (ES) [M+H]⁺ expected 550.9, found 550.9.

N-[2-(4-(1H-pyrazol-3-yl)-4H-1,2,4-triazol-3-yl)-5-methylpyridin-3-yl]-4-chloro-3-(trifluoromethyl)benzenesulfonamide

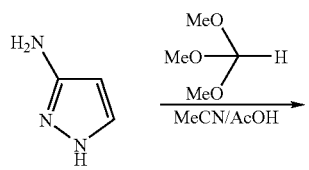

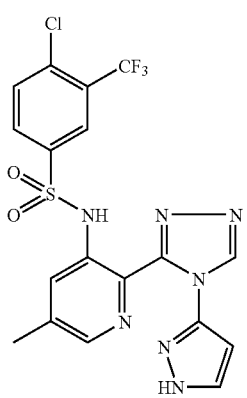

The titled compound was prepared according to general Method B using 4-chloro-N-(2-(hydrazinecarbonyl)-5-methylpyridin-3-yl)-3-(trifluoromethyl)benzenesulfonamide (MS, 409 (M+H)) and 3-aminopyrazole: ¹H NMR (400 MHz, CDCl₃) δ 11.05 (br, 1H), 8.41 (d, 1H), 7.98 (m, 3H), 7.84 (d, 2H), 7.61 (dd, 1H), 7.49 (d, 1H), 6.22 (d, 1H), 2.36 (s, 3H). MS (ES) [M+H]⁺ expected 484.0, found 484.0.

N-[2-(4-(4-bromo-1H-pyrazol-3-yl)-4H-1,2,4-triazol-3-yl)-5-chloropyridin-3-yl]-4-chloro-3-(trifluoromethyl)benzenesulfonamide

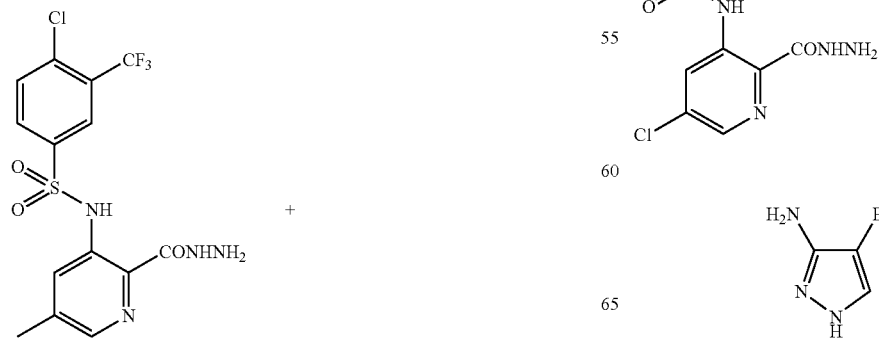

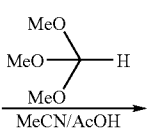

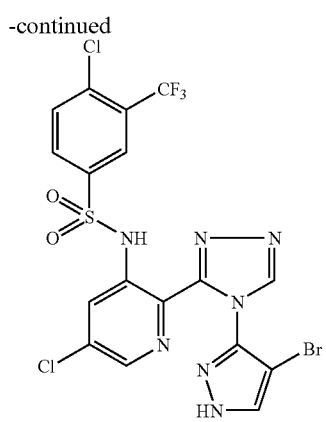

The titled compound was prepared according to general Method B using 4-chloro-N-(2-(hydrazinecarbonyl)-5-chloropyridin-3-yl)-3-(trifluoromethyl)benzenesulfonamide and 3-amino-4-bromopyrazole: $^1$H NMR (400 MHz, CDCl$_3$) δ 11.70 (br, 1H), 8.30 (s, 1H), 8.18 (d, 1H), 8.13 (d, 1H), 7.98 (d, 1H), 7.95 (dd, 1H), 7.68 (s, 1H), 7.55 (d. 1H). MS (ES) [M+H]$^+$ expected 583.9, found 583.9.

4-Chloro-N-[5-chloro-2-(4-(3-methyl-1H-pyrazol-4-yl)-4H-1,2,4-triazol-3-yl)pyridin-3-yl]-3-(trifluoromethyl)benzenesulfonamide The titled compound was prepared according to general Method B using 4-chloro-N-(2-(hydrazinecarbonyl)-5-chloropyridin-3-yl)-3-(trifluoromethyl)benzenesulfonamide and 4-amino-2-methylpyrazole: $^1$H NMR (400 MHz, CDCl$_3$) δ 8.15 (d, 2H), 8.12 (dd, 1H), 8.03 (dd, 1H), 7.97 (dd, 1H), 7.57 (d, 1H), 7.47 (d. 1H), 1.98 (s, 3H). MS (ES) [M+H]$^+$ expected 518.0, found 518.0.

4-Chloro-N-[5-chloro-2-(4-(4-methyl-1H-pyrazol-3-yl)-4H-1,2,4-triazol-3-yl)pyridin-3-yl]-3-(trifluoromethyl)benzenesulfonamide

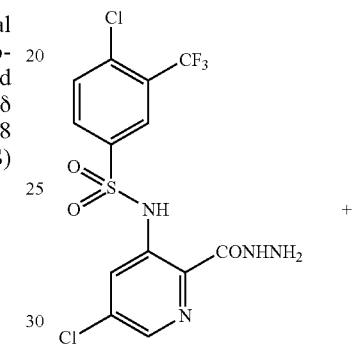

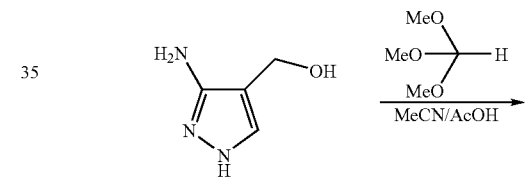

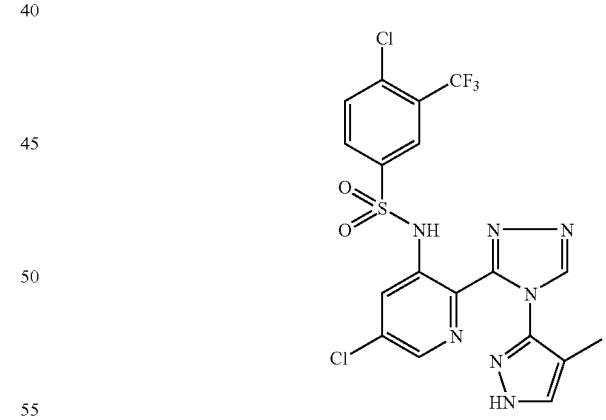

The titled compound was prepared according to general Method B using 4-chloro-N-(2-(hydrazinecarbonyl)-5-chloropyridin-3-yl)-3-(trifluoromethyl)benzenesulfonamide and 3-amino-4-hydroxymethylpyrazole((MS, 409 [M+H]$^+$, which was generated in situ by reduction of ethyl 3-amino-1H-pyrazole-4-carboxylate using LAH in THF): $^1$H NMR (400 MHz, CDCl$_3$) δ 8.28 (s, 1H), 8.16 (d, 1H), 8.13 (d, 1H), 7.97 (d, 1H), 7.94 (dd, 1H), 7.56 (d, 1H), 7.42 (d. 1H), 1.65 (s, 3H). MS (ES) [M+H]$^+$ expected 518.0, found 518.0.

N-[2-(5-amino-4-isopropyl-4H-1,2,4-triazol-3-yl)-5-chloropyridin-3-yl]-4-chloro-3-(trifluoromethyl)benzenesulfonamide

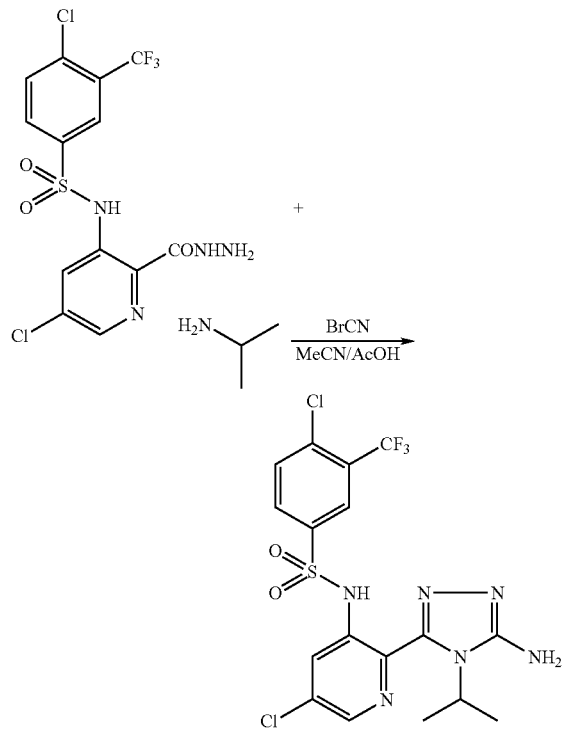

A 35 mL scintillation vial was charged with 4-chloro-N-(5-chloro-2-(hydrazinecarbonyl)pyridine-3-yl)-3-(trifluoromethyl)benzenesulfonamide (500 mg, 1.1 mmol), cyanogenbromide (200 mg, 2.0 mmol) anhydrous MeCN (5 mL). The resultant mixture was heated to 65° C. and stirred for 2 h. After cooling to room temperature, isopropylamine (500 mg, 8.2 mmol) was added followed by AcOH (0.5 mL) and the mixture was heated to 135° C. and stirred for 2 h. After cooling to room temperature, reaction mixture was concentrated under reduced pressure. The residue was further purified through automated normal-phase chromatography (10% to 100% gradient of EtOAc-Hexane) and followed by preparative HPLC (10% to 90% gradient of MeCN-water) and dried (Lyophilizer) to afford the title compound. $^1$H NMR (400 MHz, CDCl$_3$) 8.28 (d, 1H), 8.18 (d, 1H), 8.10 (d, 1H), 7.90 (dd, 1H), 7.58 (d, 1H), 4.32 (br, 1H), 3.88 (m, 1H), 1.34 (d (d, 6H). MS (ES) [M+H]$^+$ expected 495.0, found 495.0.

4-Chloro-N-[5-chloro-2-(5-(dimethylamino)methyl-4-isopropyl-4H-1,2,4-triazol-3-yl)pyridin-3-yl]-3-(trifluoromethyl)benzenesulfonamide

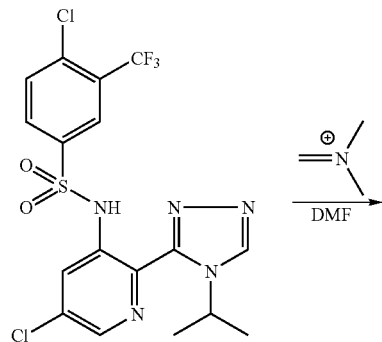

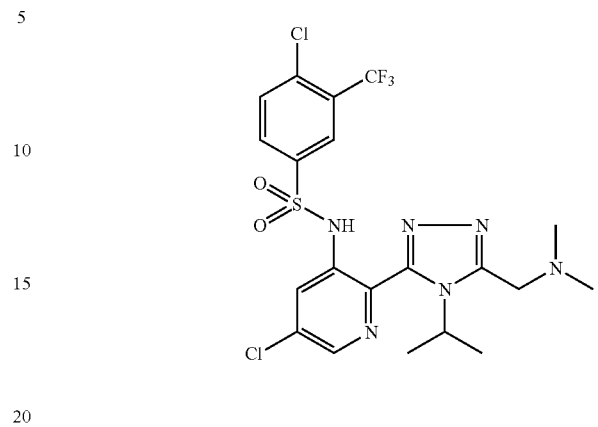

A 25 mL scintillation vial was charged with 4-Chloro-N-[5-chloro-2-(4-isopropyl-4H-1,2,4-triazol-3-yl)pyridin-3-yl]-3-(trifluoromethyl)benzenesulfonamide (60 mg, 0.14 mmol), Eschenmoser salt (25 mg, 0.2 mmol) and anhydrous DMF (2 mL). The resultant mixture was heated to 130° C. and stirred for 3 h. After cooling to room temperature, the residue was purified through preparative HPLC (10% to 90% gradient of MeCN-water) and dried (Lyophilizer) to afford the title compound. $^1$H NMR (400 MHz, CDCl$_3$) 8.35 (d, 1H), 8.16 (d, 1H), 8.02 (d, 1H), 7.88 (dd, 1H), 7.50 (d, 1H), 5.40 (m, 1H), 3.65 (s, 2H), 2.23 (s, 6H), 1.42 (d, 6H). MS (ES) [M+H]$^+$ expected 537.0, found 537.0.

4-Chloro-N-[5-chloro-2-(5-(methoxymethyl)-4-(1H-pyrazol-3-yl)-4H-1,2,4-triazol-3-yl)pyridin-3-yl]-3-(trifluoromethyl)benzenesulfonamide

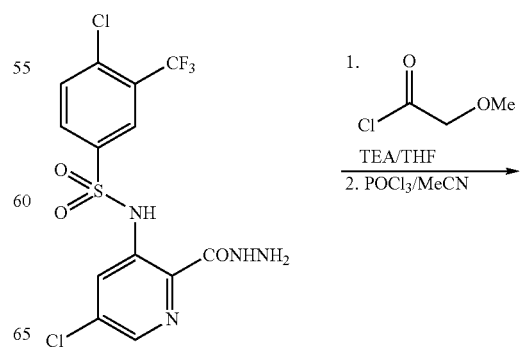

4-Chloro-N-[5-chloro-2-(4-phenyl-5-(trifluoromethyl)-4H-1,2,4-triazol-3-yl)pyridin-3-yl]-3-trifluoromethyl)benzenesulfonamide

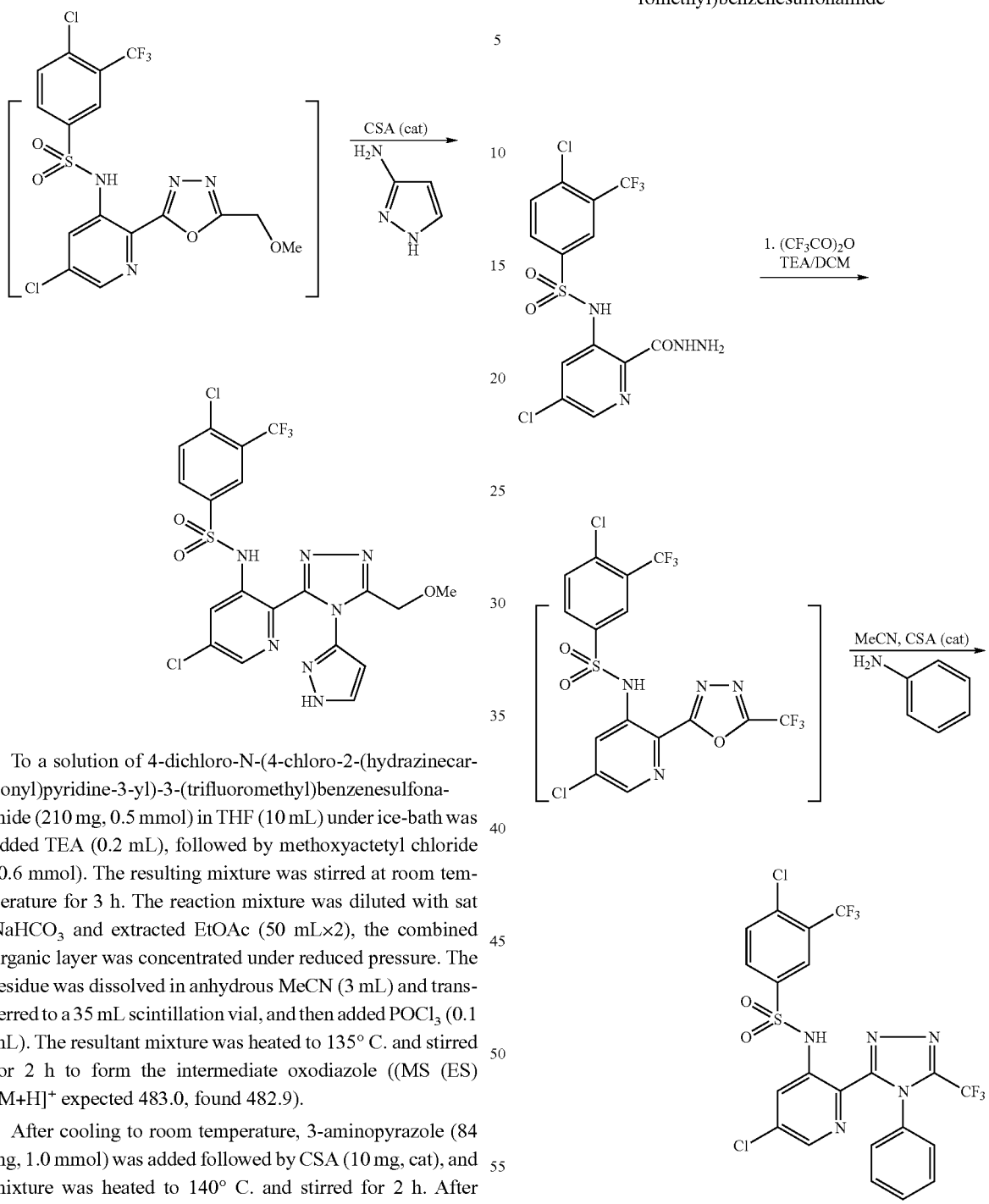

To a solution of 4-dichloro-N-(4-chloro-2-(hydrazinecarbonyl)pyridine-3-yl)-3-(trifluoromethyl)benzenesulfonamide (210 mg, 0.5 mmol) in THF (10 mL) under ice-bath was added TEA (0.2 mL), followed by methoxyactetyl chloride (0.6 mmol). The resulting mixture was stirred at room temperature for 3 h. The reaction mixture was diluted with sat NaHCO$_3$ and extracted EtOAc (50 mL×2), the combined organic layer was concentrated under reduced pressure. The residue was dissolved in anhydrous MeCN (3 mL) and transferred to a 35 mL scintillation vial, and then added POCl$_3$ (0.1 mL). The resultant mixture was heated to 135° C. and stirred for 2 h to form the intermediate oxodiazole ((MS (ES) [M+H]$^+$ expected 483.0, found 482.9).

After cooling to room temperature, 3-aminopyrazole (84 mg, 1.0 mmol) was added followed by CSA (10 mg, cat), and mixture was heated to 140° C. and stirred for 2 h. After cooling to room temperature, the reaction mixture was concentrated under reduced pressure. The residue was purified through automated normal-phase chromatography (10% to 100% gradient of EtOAc-Hexane) preparative HPLC (10% to 90% gradient of MeCN-water) and dried (Lyophilizer) to afford the title compound. $^1$H NMR (400 MHz, CDCl$_3$) δ 8.16 (d, 1H), 8.10 (d, 1H), 7.95 (d, 1H), 7.92 (dd, 1H), 7.68 (d, 1H), 7.55 (d, 1H), 6.33 (d, 1H), 4.52 (s, 2H), 3.32 (s, 3H). MS (ES) [M+H]$^+$ expected 548.0, found 548.0.

The title compound was prepared according to the procedure described in Example [00473] using aniline. MS (ES) [M+H]$^+$ expected 582.0, found 581.9.

The compounds in Table 2 were prepared by the indicated general procedure described above. MS (ES) [M+H]$^+$ data was collected and compared to the expected value to confirm the identity of the compound.

TABLE 2

Compounds prepared by General Procedures and MS Data

| STRUCTURE | Synthetic Method | Observed Molecular Ion (M + 1) |
|---|---|---|
| (4-tert-butylphenyl)sulfonyl-N-[5-chloro-2-(4-isopropyl-5-methyl-4H-1,2,4-triazol-3-yl)pyridin-3-yl] | B | 448.1 |
| (4-tert-butylphenyl)sulfonyl-N-[5-chloro-2-(4,5-dimethyl-4H-1,2,4-triazol-3-yl)pyridin-3-yl] | B | 420.0 |
| (4-tert-butylphenyl)sulfonyl-N-[5-chloro-2-(1-isopropyl-1H-1,2,4-triazol-5-yl)pyridin-3-yl] | B | 434.1 |
| (4-tert-butylphenyl)sulfonyl-N-[5-chloro-2-(4-methyl-5-(pyridin-3-yl)-4H-1,2,4-triazol-3-yl)pyridin-3-yl] | C | 483.0 |

TABLE 2-continued

Compounds prepared by General Procedures and MS Data

| STRUCTURE | Synthetic Method | Observed Molecular Ion (M + 1) |
|---|---|---|
| | C | 483.1 |
| | D | 475.1 |
| | B | 446.1 |
| | B | 434.1 |

TABLE 2-continued

Compounds prepared by General Procedures and MS Data

| STRUCTURE | Synthetic Method | Observed Molecular Ion (M + 1) |
|---|---|---|
| | C | 450.2 |
| | C | 478.1 |
| | B | 420.0 |
| | B | 406.1 |

TABLE 2-continued

Compounds prepared by General Procedures and MS Data

| STRUCTURE | Synthetic Method | Observed Molecular Ion (M + 1) |
|---|---|---|
| 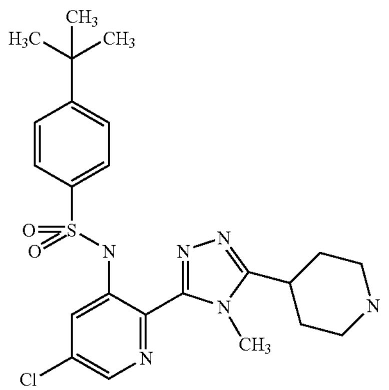 | D | 490.1 |
| 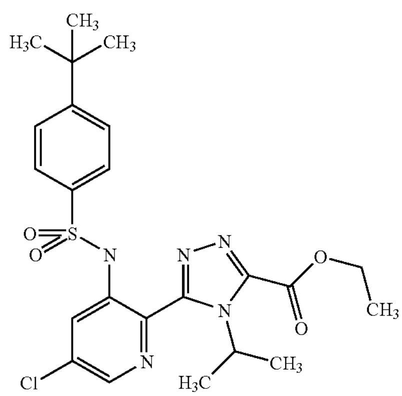 | B | 506.0 |
| 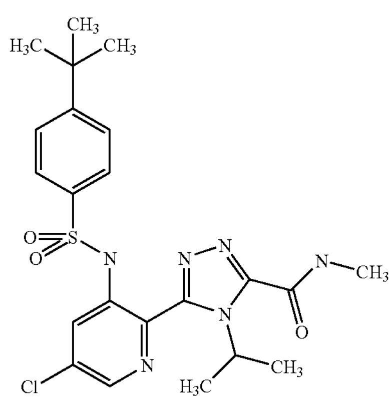 | E | 491.1 |

TABLE 2-continued

Compounds prepared by General Procedures and MS Data

| STRUCTURE | Synthetic Method | Observed Molecular Ion (M + 1) |
|---|---|---|
| [structure] | F | 492.1 |
| [structure] | E | 505.1 |
| [structure] | G | 449.1 |

TABLE 2-continued

Compounds prepared by General Procedures and MS Data

| STRUCTURE | Synthetic Method | Observed Molecular Ion (M + 1) |
|---|---|---|
| | C | 520.1 |
| 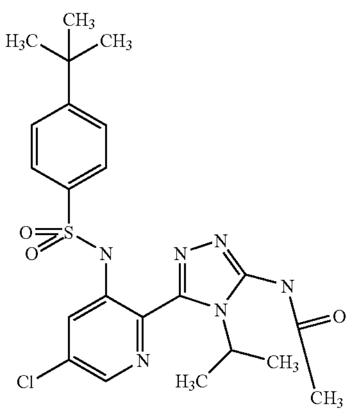 | H | 491.1 |
| | C | 464.0 |

TABLE 2-continued

Compounds prepared by General Procedures and MS Data

| STRUCTURE | Synthetic Method | Observed Molecular Ion (M + 1) |
|---|---|---|
| | B | 541.2 |
| | I | 441.1 |
| | B | 455.1 |

TABLE 2-continued

Compounds prepared by General Procedures and MS Data

| STRUCTURE | Synthetic Method | Observed Molecular Ion (M + 1) |
|---|---|---|
| [structure] | I | 461.0 |
| [structure] | I | 475.0 |
| [structure] | B | 468.0 |

TABLE 2-continued

Compounds prepared by General Procedures and MS Data

| STRUCTURE | Synthetic Method | Observed Molecular Ion (M + 1) |
|---|---|---|
| [structure: N-(5-chloro-2-(4-(2-fluorophenyl)-4H-1,2,4-triazol-3-yl)pyridin-3-yl)-4-tert-butylbenzenesulfonamide] | B | 486.0 |
| [structure: N-(5-chloro-2-(5-(isoxazol-5-yl)-4-methyl-4H-1,2,4-triazol-3-yl)pyridin-3-yl)-4-tert-butylbenzenesulfonamide] | C | 459.0 |
| [structure: N-(5-chloro-2-(5,6-dihydro-8H-[1,2,4]triazolo[3,4-c][1,4]oxazin-3-yl)pyridin-3-yl)-4-tert-butylbenzenesulfonamide] | C | 448.0 |

TABLE 2-continued

Compounds prepared by General Procedures and MS Data

| STRUCTURE | Synthetic Method | Observed Molecular Ion (M + 1) |
|---|---|---|
| [structure] | D | 447.7 |
| [structure] | B | 448.1 |

Measuring Efficacy of Chemokine Modulators

In Vitro Assays

A variety of assays can be used to evaluate the compounds provided herein, including signaling assays, migration assays, ligand binding assays, and other assays of cellular response. Chemokine receptor signaling assays can be used to measure the ability of a compound, such as a potential CCR2 antagonist, to block CCR2 ligand-(e.g. MCP-1)-induced signaling or a potential CCR9 antagonist, to block CCR9 ligand- (e.g. TECK)-induced signaling. A migration assay can be used to measure the ability of a compound of interest, such as a possible chemokine antagonist, to block chemokine-mediated cell migration in vitro. The latter is believed to resemble chemokine-induced cell migration in vivo. A ligand binding assay can be used to measure the ability of a compound, such as a potential CCR2 antagonist, to block the interaction of MCP-1 with its receptor or a potential CCR9 antagonist, to block the interaction of TECK with its receptor.

In a suitable assay, a chemokine protein (whether isolated or recombinant) is used which has at least one property, activity, or functional characteristic of a mammalian chemokine protein. The property can be a binding property (to, for example, a ligand or inhibitor), a signaling activity (e.g., activation of a mammalian G protein, induction of rapid and transient increase in the concentration of cytosolic free calcium ion), cellular response function (e.g., stimulation of chemotaxis or inflammatory mediator release by leukocytes), and the like.

The assay can be a cell-based assay that utilizes cells stably or transiently transfected with a vector or expression cassette having a nucleic acid sequence that encodes the chemokine receptor. Cell lines naturally expressing the chemokine can also be used. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., MCP-1 or TECK) as a competitor.

Binding inhibition assays can be used to evaluate the present compounds. In these assays, the compounds are evaluated as inhibitors of ligand binding using, for example, MCP-1 or TECK. In one embodiment, the CCR2 receptor is contacted with a ligand such as MCP-1 and a measure of ligand binding is made. The receptor is then contacted with a test agent in the presence of a ligand (e.g., MCP-1) and a second measurement of binding is made. In another embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express the chemokine, or a membrane fraction from cells which express the chemokine.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., *Cell*, 72:415425 (1993); Van Riper et al., *J. Exp. Med.*, 177:851-856 (1993) and Dahinden et al., *J. Exp. Med.*, 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer et al., WO 94/20142; Berman et al., *Immunol. Invest.*, 17:625-677 (1988); and Kavanaugh et al., *J. Immunol.*, 146:4149-4156 (1991)).

Calcium signaling assays measure calcium concentration over time, preferably before and after receptor binding. These assays can be used to quantify the generation of a receptor-signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between a chemokine receptor and a known chemokine ligand, chemokine receptor-expressing cells (CCR2-expressing cells such as THP-1 cells or CCR9-expressing cells such as T cell line MOLT-4 cells) are first incubated with a compound of interest, such as a potential chemokine antagonist, at increasing concentrations. The cell number can be from $10^5$ to $5 \times 10^5$ cells per well in a 96-well microtiter plate. The concentration of the compound being tested may range from 0 to 100 µM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the chemokine ligand (MCP-1 for CCR2 or TECK for CCR9) at 5-100 nM final concentration, and the signal of intracellular calcium increase (also called calcium flux) is recorded. The efficacy of a compound as an inhibitor of binding between the chemokine and the ligand can be calculated as an $IC_{50}$ (the concentration needed to cause 50% inhibition in signaling) or $IC_{90}$ (at 90% inhibition).

In vitro cell migration assays can be performed (but are not limited to this format) using the 96-well microchamber (called ChemoTX™). The ChemoTX™ system is well known to those skilled in the art as a type of chemotactic/cell migration instrument. In this assay, CCR2-expressing cells (such as THP-1) or CCR9-expressing cells (such as MOLT-4) are first incubated with a compound of interest, such as a possible CCR2 or CCR9 antagonist, respectively, at increasing concentrations. Typically, fifty thousand cells per well are used, but the amount can range from $10^3$-$10^6$ cells per well. The chemokine ligand (for example, CCR2 ligand MCP-1, typically at 0.1 nM (but can range from 5-100 nM); or CCR9 ligand TECK, typically at 50 nM (but can range from 5-100 nM)), is placed at the lower chamber and the migration apparatus is assembled. Twenty microliters of test compound-treated cells are then placed onto the membrane. Migration is allowed to take place at 37° C. for a period of time, typically 1.5 hours for CCR2 or 2.5 hours for CCR9. At the end of the incubation, the number of cells that migrated across the membrane into the lower chamber is then quantified. The efficacy of a compound as an inhibitor of chemokine-mediated cell migration is calculated as an $IC_{50}$ (the concentration needed to reduce cell migration by 50%) or $IC_{90}$ (for 90% inhibition).

In vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala, et al., *J Immunol*, 161(10):5733-44 (1998)) involves genetic deletion of the murine multi-drug resistant gene (MDR). MDR knockout mice (MDR–/–) are susceptible to developing a severe, spontaneous intestinal inflammation when maintained under specific pathogen-free facility conditions. The intestinal inflammation seen in MDR–/– mice has a pathology similar to that of human inflammatory bowel disease (IBD) and is defined by Th1 type T cells infiltration into the lamina propria of the large intestine.

Another murine model was described by Davidson et al., *J. Exp. Med.*, 184(1):241-51(1986). In this model, the murine IL-10 gene was deleted and mice rendered deficient in the production of interleukin 10 (IL-10–/–). These mice develop a chronic inflammatory bowel disease (IBD) that predominates in the colon and shares histopathological features with human IBD.

Another murine model for IBD has been described by Powrie et al., *Int Immunol.*, 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Murine Models with Pathology Similar to Human Crohn's Disease

The TNF ARE(−/−) model. The role of TNF in Crohn's disease in human has been demonstrated more recently by success of treatment using anti-TNF alpha antibody by Targan et al., *N. Engl. J. Med.*, 337(15):1029-35 (1997). Mice with aberrant production of TNF-alpha due to genetic alteration in the TNF gene (ARE−/−) develop Crohn's-like inflammatory bowel diseases (see Kontoyiannis et al., *Immunity*, 10(3):387-98 (1999)).

The SAMP/yit model. This is model described by Kosiewicz et al., *J. Clin. Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Examples of in vitro Assays

Reagents

THP-1 cells and MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine proteins MCP-1 and TECK were obtained from R&D Systems (Minneapolis, Minn.). $^{125}$I-labeled MCP-1 protein was obtained from Amersham (Piscataway, N.J.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Conventional Migration Assay

Conventional migration assay was used to determine the efficacy of potential receptor antagonists in blocking migration mediated through chemokines (such as CCR2 or CCR9). This assay was routinely performed using the ChemoTX® microchamber system with a 5-μm pore-sized polycarbonate membrane. To begin such an assay, chemokine expressing cells (such as THP-1 cells for CCR2 assay or MOLT-4 cells for CCR9 assay) were harvested by centrifugation of cell suspension at 1000 RPM on a GS-6R Beckman centrifuge. The cell pellet was resuspended in chemotaxis buffer (HBSS with 0.1% BSA) at $10\times10^6$ cells/mL for CCR2 assay ($5\times10^6$ cells/mL for CCR9 assay). Test compounds at desired concentrations were prepared from 10 mM stock solutions by serial dilutions in chemotaxis buffer. An equal volume of cells and compounds were mixed and incubated at room temperature for 15 minutes. Afterwards, 20 μL of the mixture was transferred onto the porous membrane of a migration microchamber, with 29 μL of chemokine ligand (0.1 nM chemokine MCP-1 protein for CCR2 assay or 50 nm chemokine TECK protein for CCR9 assay) placed at the lower chamber. Following an incubation at 37° C. (90-minute for CCR2; 150-minute for CCR9), during which cells migrated against the chemokine gradient, the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. $IC_{50}$ calculation was further performed by non-linear squares regression analysis using Graphpad Prism (Graphpad Software, San Diego, Calif.).

BiRAM Assay

The primary screen to identify chemokine antagonists was carried out using BiRAM assay (WO 02101350, US2004023286), which detects potential hits by their ability to activate cell migration under inhibitory chemokine concentration. To begin such an assay, chemokine expressing cells (such as THP-1 cells for CCR2 assay or MOLT-4 cells for CCR9 assay) were harvested by centrifugation of cell suspension at 1000 RPM on a GS-6R Beckman centrifuge. The cell pellet was resuspended in chemotaxis buffer (HBSS/0.1% BSA) at $10\times10^6$ cells/mL for CCR2 assay ($5\times10^6$ cells/mL for CCR9 assay). Twenty-five microliters of cells was mixed with an equal volume of a test compound diluted to 20 μM in the same buffer. Twenty microliters of the mixture was transferred onto the filter in the upper chemotaxis chamber, with 29 μL of chemokine solution containing chemokine ligand (100 nM chemokine MCP-1 and MIP-1α protein for CCR2 assay or 500 nm chemokine TECK protein for CCR9 assay) was placed in the lower chamber. Following an incubation at 37° C. (90-minute for CCR2; 150-minute for CCR9), the assay was terminated by removing the cell drops from atop the filter. To quantify cells migrated across the membrane, 5 μL of 7× CyQUANT® solution was added to each well in the lower chamber, and the fluorescence signal measured on a Spectrafluor Plus fluorescence plate reader (TECAN, Durham, N.C.).

For selection of potential hits, the level of migration activation was calculated as a RAM index—the ratio between the signal of a particular well and the median signal of the whole plate. Compounds with a RAM index of greater than 1.5 for CCR2 assay (1.8 for CCR9 assay) were regarded as RAM positive, and were selected for $IC_{50}$ determinations in conventional functional assays.

Calcium Flux Assay

Calcium flux assay measures an increase in intracellular calcium following ligand-induced receptor activation. In the screen of chemokine antagonists, it was used as a secondary assay carried out on a FLIPR® machine (Molecular Devices, Mountain View, Calif.). To begin an assay, chemokine expressing cells (such as THP-1 cells for CCR2 assay or MOLT-4 cells for CCR9 assay) were harvested by centrifugation of cell suspension, and resuspended to $1.5\times10^6$ cells/mL in HBSS (with 1% fetal calf serum). Cells were then labeled with a calcium indicator dye Fluo-4 AM for 45 minutes at 37° C. with gentle shaking. Following incubation, cells were pelleted, washed once with HBSS and resuspended in the same buffer at a density of $1.6\times10^6$ cells/mL. One hundred microliters of labeled cells were mixed with 10 μL of test compound at the appropriate concentrations on an assay plate. Chemokine protein (MCP-1 at a final concentration of 0.1 nM for CCR2 assay or TECK at a final concentration of 25 nM for CCR9 assay) to activate the receptor. The degree of inhibition was determined by comparing calcium signals between compound-treated and untreated cells. $IC_{50}$ calculations were further performed by non-linear squares regression analysis using Graphpad Prism (Graphpad Software, San Diego, Calif.).

Ligand Binding Assay

Ligand binding assay was used to determine the ability of potential CCR2 antagonists to block the interaction between CCR2 and its ligand MCP-1. CCR2 expressing THP-1 cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $2.2 \times 10^5$ cells/mL. Binding assays were set up as follows. First, 0.09 mL of cells ($1 \times 10^5$ THP-1 cells/well) was added to the assay plates containing the compounds, giving a final concentration of ~2-10 μM each compound for screening (or part of a dose response for compound $IC_{50}$ determinations). Then 0.09 mL of $^{125}I$ labeled MCP-1 (obtained from Amersham; Piscataway, N.J.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 μL; Microscint 20, Packard Instruments) was added to each well, the plates were sealed and radioactivity measured in a Top Count scintillation counter (Packard Instruments). Control wells containing either diluent only (for total counts) or excess MCP-1 (1 μg/mL, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled MCP-1 to the receptor by 50%.

Discovery of Chemokine Antagonists

The discovery of chemokine antagonists was carried out in two steps: First, BiRAM assay was used to screen a compound library in a high-throughput manner. The assay detected compounds by their ability to cause a positive migration signal under BiRAM condition. Secondly, BiRAM positive compounds were tested to determine their $IC_{50}$ values using the conventional migration, calcium flux assays and ligand binding assays.

For instance, in a screen of approximately 100,000 compounds, 2000 individual wells representing approximately 2% of total compounds showed a desired RAM index (greater than 1.5 for CCR2; greater than 1.8 for CCR9). These compounds were cheery-picked and retested in duplicate wells by RAM assay. A total of 156 compounds were confirmed BiRAM positives.

Since a BiRAM positive signal indicates only the presence of a receptor antagonist and not how strongly it blocks receptor functions, the BiRAM positive compounds were further tested for potency in conventional migration, calcium flux and ligand binding assays. $IC_{50}$ determinations on this subset discovered several compounds with an $IC_{50}$ less than 1 μM and that did not inhibit other chemokine receptors examined at significant levels.

In Vivo Efficacy

A 17-day study of type II collagen-induced arthritis is conducted to evaluate the effects of a modulator on arthritis-induced clinical ankle swelling. Rat collagen-induced arthritis is an experimental model of polyarthritis that has been widely used for preclinical testing of numerous anti-arthritic agents (see Trentham et al., *J. Exp. Med.*, 146(3):857-868 (1977), Bendele et al., *Toxicologic Pathol.*, 27:134-142 (1999), Bendele et al., *Arthritis Rheum.*, 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. The test modulator is dosed daily by sub-cutaneous injection from day 9 to day 17 at a dose of 100 mg/kg and a volume of 1 mL/kg in the following vehicle (24.5% Cremaphore EL, 24.5% common oil, 1% Benzylalcohol and 50% Distilled water). Caliper measurements of the ankle joint diameter are taken daily, and reducing joint swelling is taken as a measure of efficacy.

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, a CCR9 antagonist is evaluated by prophylactic administration for its ability to delay disease onset. Female mice (n=34) are dosed with 50 mg/kg twice a day by subcutaneous injections for 14 consecutive weeks starting at age 10 weeks. The study is evaluated for IBD-associated growth retardation.

Evaluation of a Test Modulator in a Rat Model of Thioglycollate-Induced Peritoneal Inflammation A 2-day study of thioglycollate-induced inflammation is conducted to evaluate the effects of the test modulator. The hallmarks of this model are reliable onset and progression of robust, easily measurable inflammatory cellular infiltrate. For the induction of inflammatory peritonitis in Lewis rats, Brewer-Thioglycollate (1.0 mL, 4% solution in distilled water) is injected intra peritoneal (i.p.). Before this injection, the treatment group received test modulator or vehicle and the control group received the same volume of PBS as i.p. injection. After 2 days, a peritoneal lavage as performed with ice-cold PBS containing 1 mM EDTA. The recovered cells are counted with a cell counter (Coulter Counter; Coulter Pharmaceutical, Palo Alto, Calif.) and monocytes/macrophages were identified by flow cytometry using light-scatter properties.

Evaluation of a Test Modulator in a Mouse Model of Bacterial Infection

A 1-day study of *streptococcus pneumoniae* infection is conducted to evaluate the effects of the test modulator. The model measures bacterial infection and spread in an animal following pulmonary infection with live bacterial cultures, measured by inflammatory cellular infiltrate, and assessment of bacterial burden. C57/B6 mice are inoculated intra nasally with LD50 400 CFU at day 0. Groups are either test modulator or vehicle control treated 1 day prior to bacterial inoculation and twice daily throughout the study. Bacterial burden is measured at 24 hours by plating serial dilutions of homogenized lung tissue on agar plates and counting colonies.

Pharmacologics to be Used in Conjunction with CCR2 Compounds

Pharmacological agents that can be used in conjunction with the CCR2 antagonists of the current invention include those used for the treatments of atherosclerosis, restenosis, multiple sclerosis, pulmonary fibrosis, inflammatory bowel disease, rheumatoid arthritis, graft-versus-host disease, renal fibrosis, psoriasis, transplantation rejection, obesity, diabetes, hypercholesterolemia and cancer.

In the tables below, structures and activity are provided for representative compounds described herein. Activity is provided as follows for either or both of the chemotaxis assay and/or calcium mobilization assays, described above.

TABLE 3
Compounds with CCR2 activity in one of the chemotaxis, binding or calcium mobilization assays, with IC50 < 1000 nM.
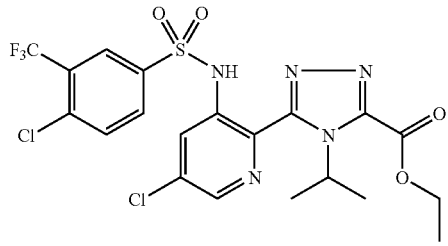
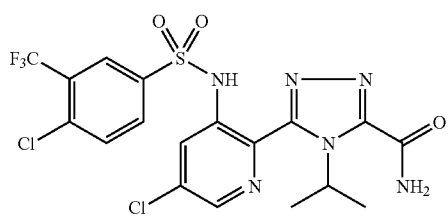
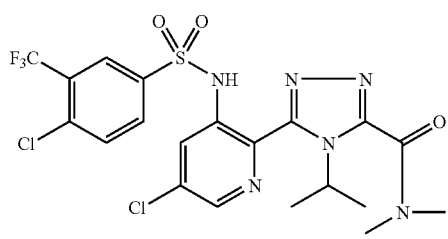
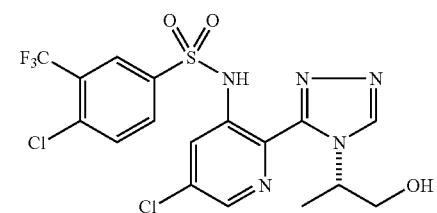
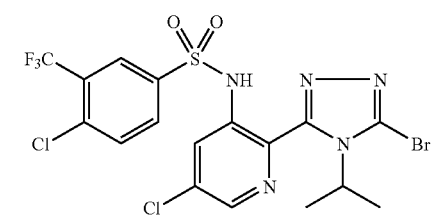
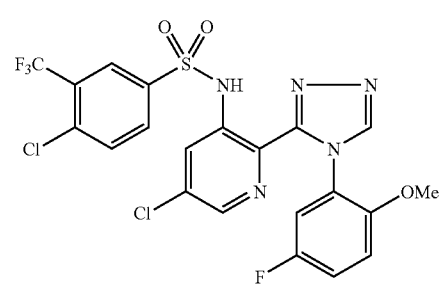
TABLE 3-continued
Compounds with CCR2 activity in one of the chemotaxis, binding or calcium mobilization assays, with IC50 < 1000 nM.
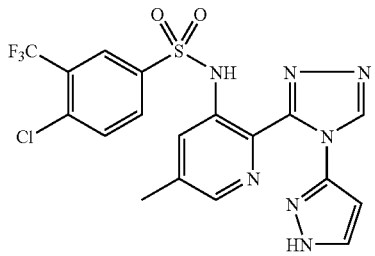
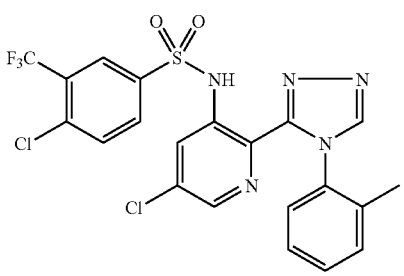
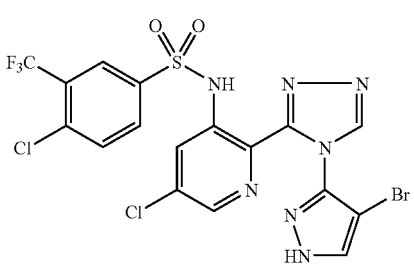
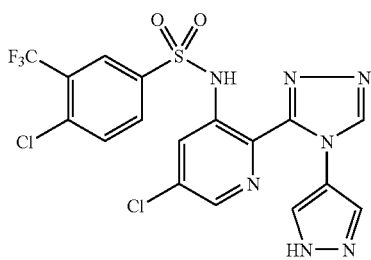
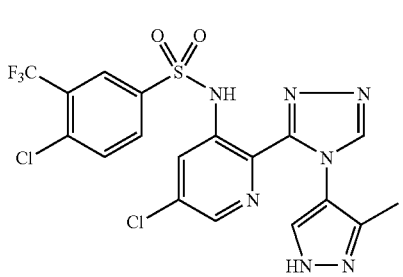

TABLE 3-continued
Compounds with CCR2 activity in one of the chemotaxis, binding or calcium mobilization assays, with IC50 < 1000 nM.
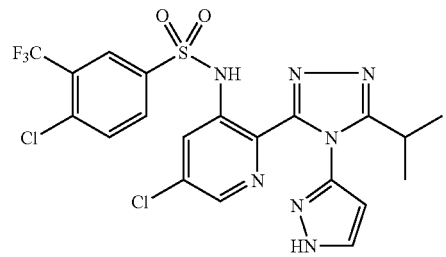
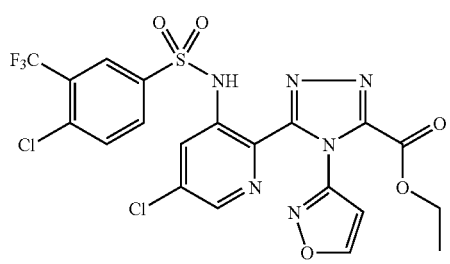
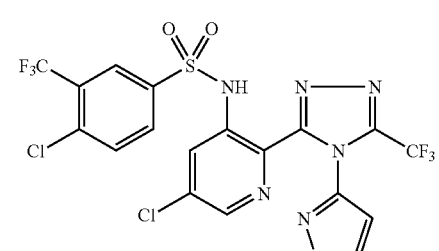
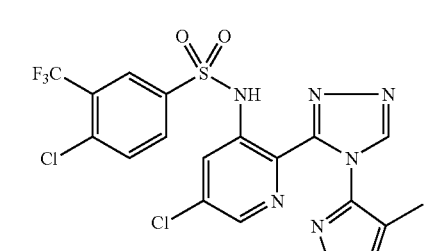
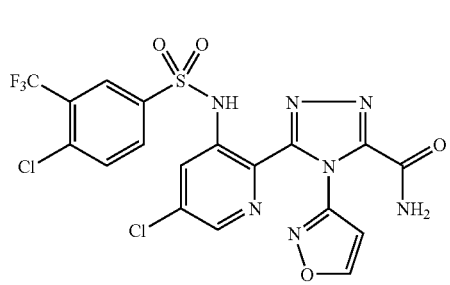
TABLE 3-continued
Compounds with CCR2 activity in one of the chemotaxis, binding or calcium mobilization assays, with IC50 < 1000 nM.
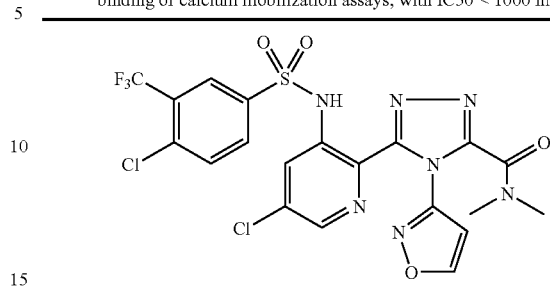
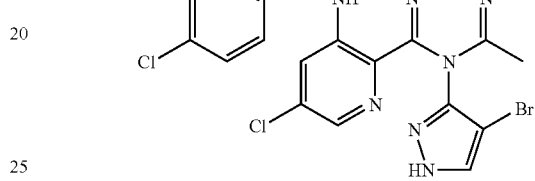
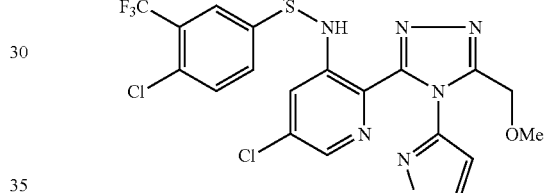
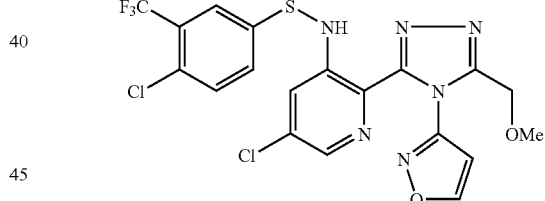
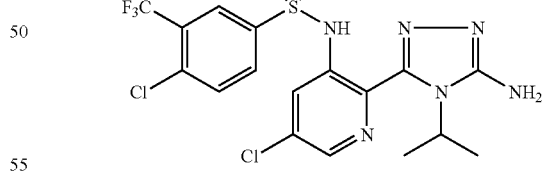
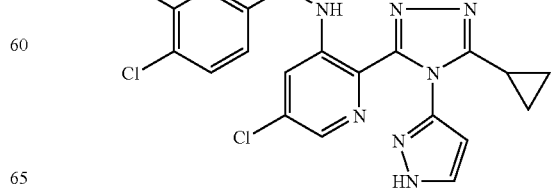

TABLE 3-continued
Compounds with CCR2 activity in one of the chemotaxis, binding or calcium mobilization assays, with IC50 < 1000 nM.
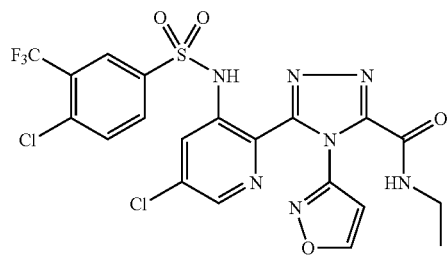
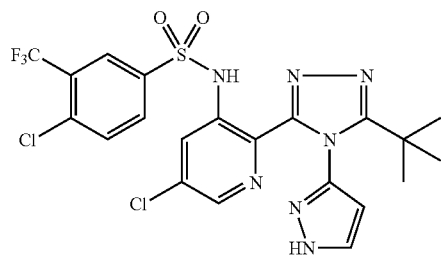
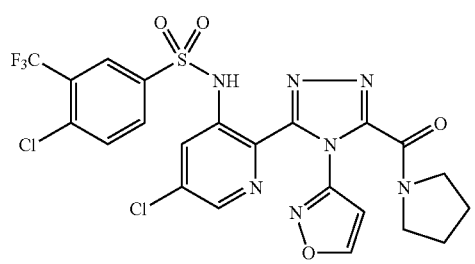
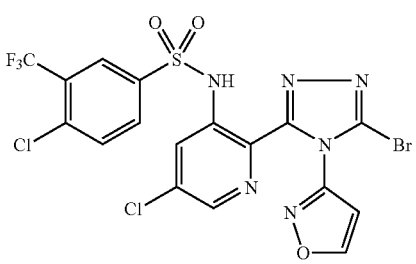
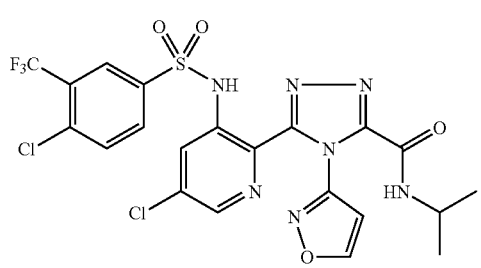
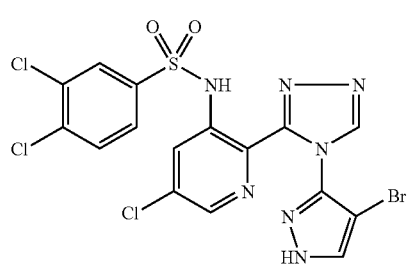
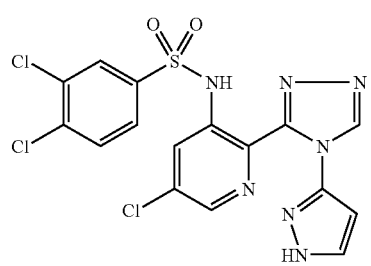
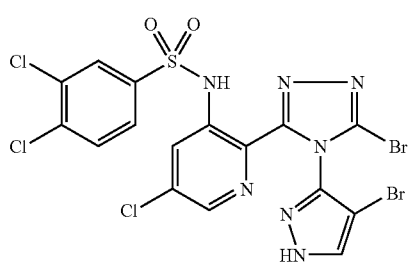
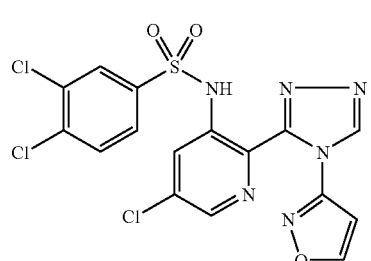
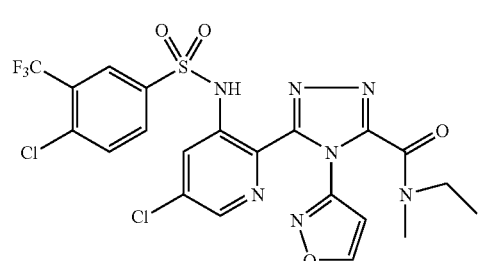

TABLE 3-continued
Compounds with CCR2 activity in one of the chemotaxis, binding or calcium mobilization assays, with IC50 < 1000 nM.
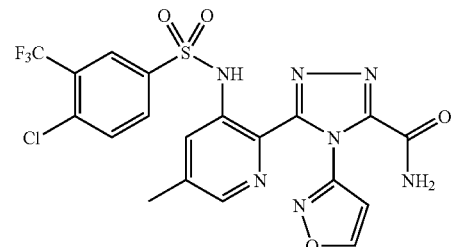
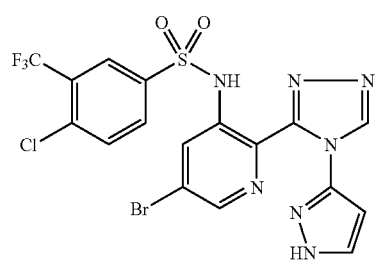
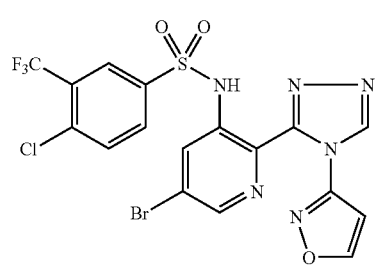
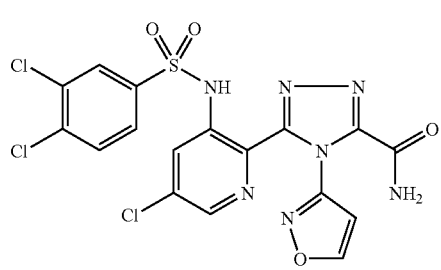
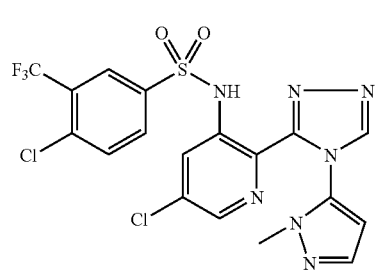
TABLE 3-continued
Compounds with CCR2 activity in one of the chemotaxis, binding or calcium mobilization assays, with IC50 < 1000 nM.
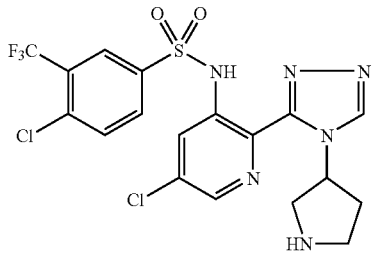
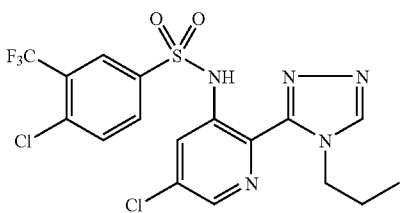
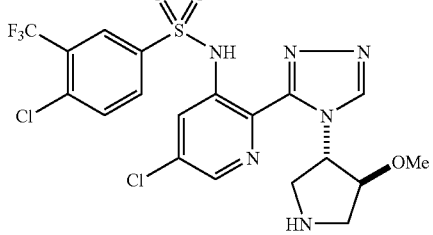
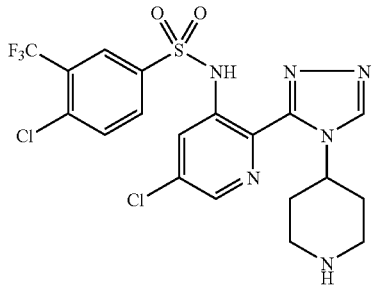
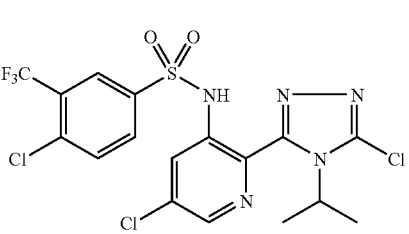
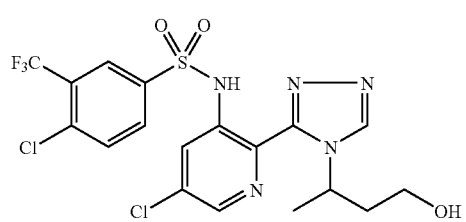

TABLE 3-continued
Compounds with CCR2 activity in one of the chemotaxis, binding or calcium mobilization assays, with IC50 < 1000 nM.
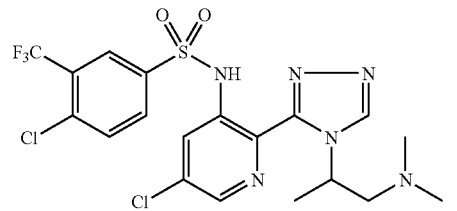
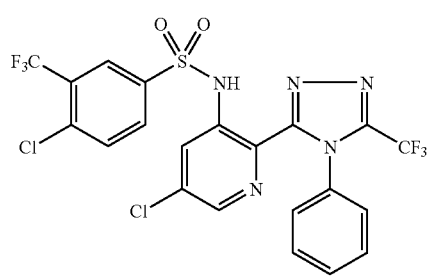
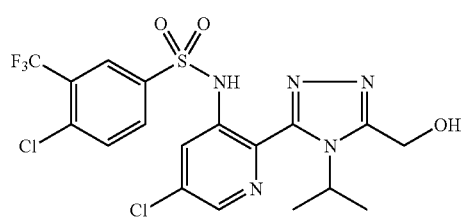
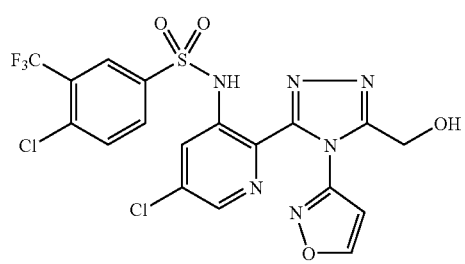
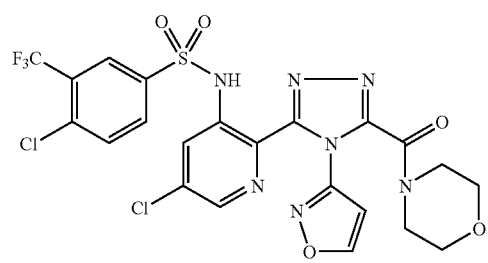
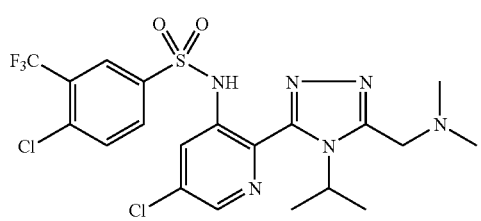
TABLE 3-continued
Compounds with CCR2 activity in one of the chemotaxis, binding or calcium mobilization assays, with IC50 < 1000 nM.
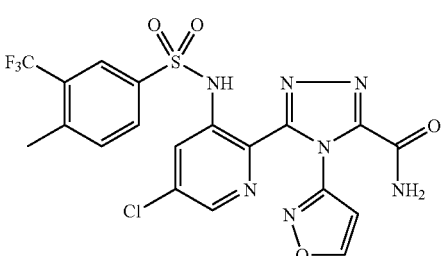
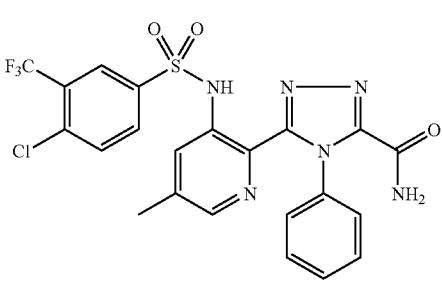
TABLE 4
Compounds with CCR9 activity in one of the chemotaxis, binding or calcium mobilization assays, with IC50 < 1000 nM
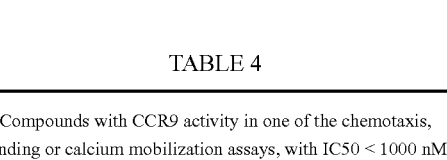
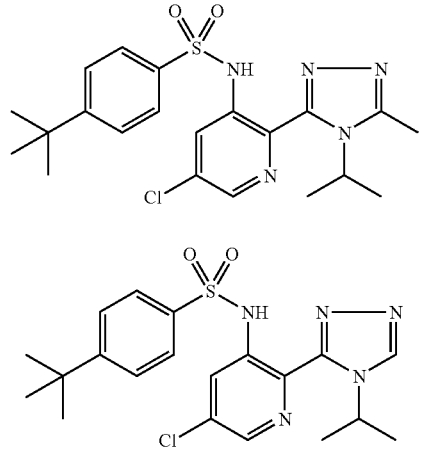
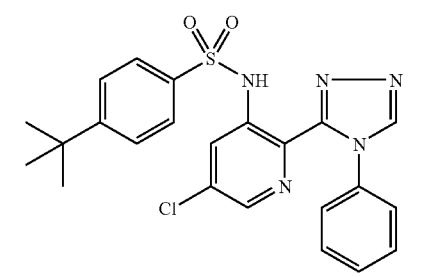

TABLE 4-continued
Compounds with CCR9 activity in one of the chemotaxis, binding or calcium mobilization assays, with IC50 < 1000 nM
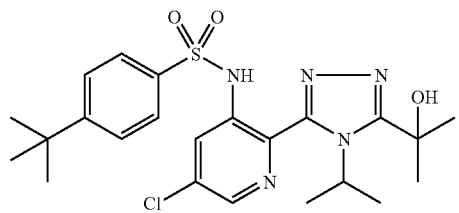
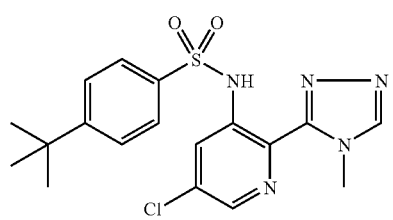
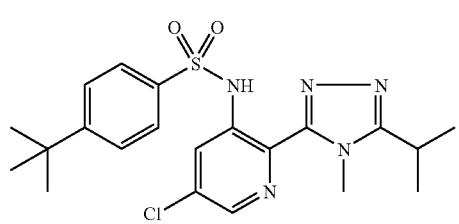
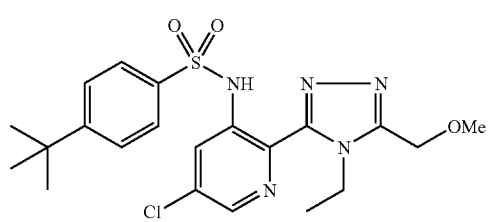
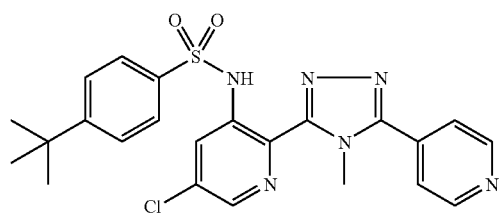
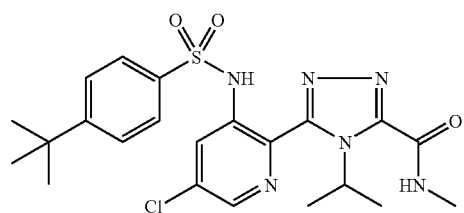
TABLE 4-continued
Compounds with CCR9 activity in one of the chemotaxis, binding or calcium mobilization assays, with IC50 < 1000 nM
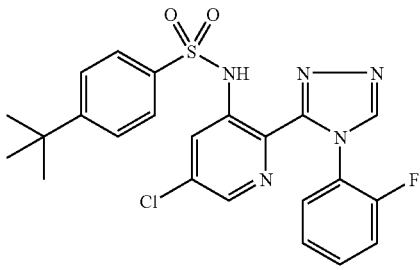
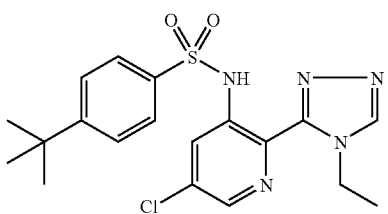
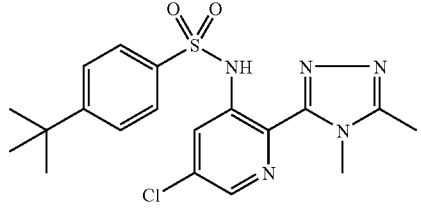
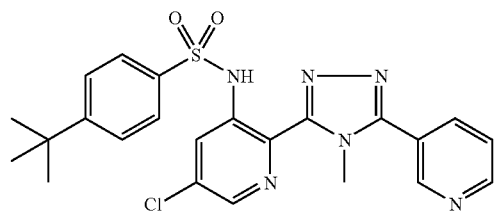
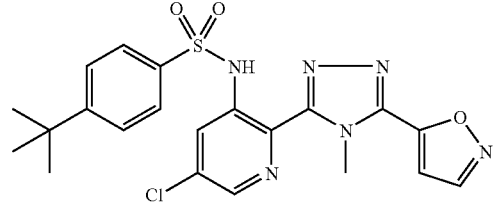
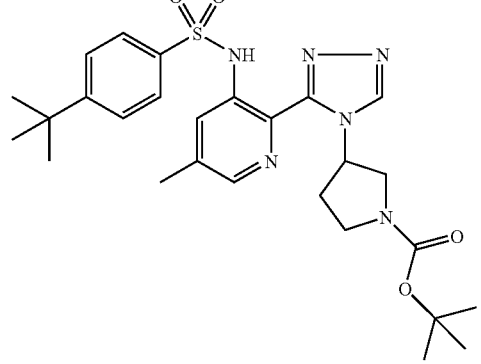

TABLE 4-continued
Compounds with CCR9 activity in one of the chemotaxis, binding or calcium mobilization assays, with IC50 < 1000 nM
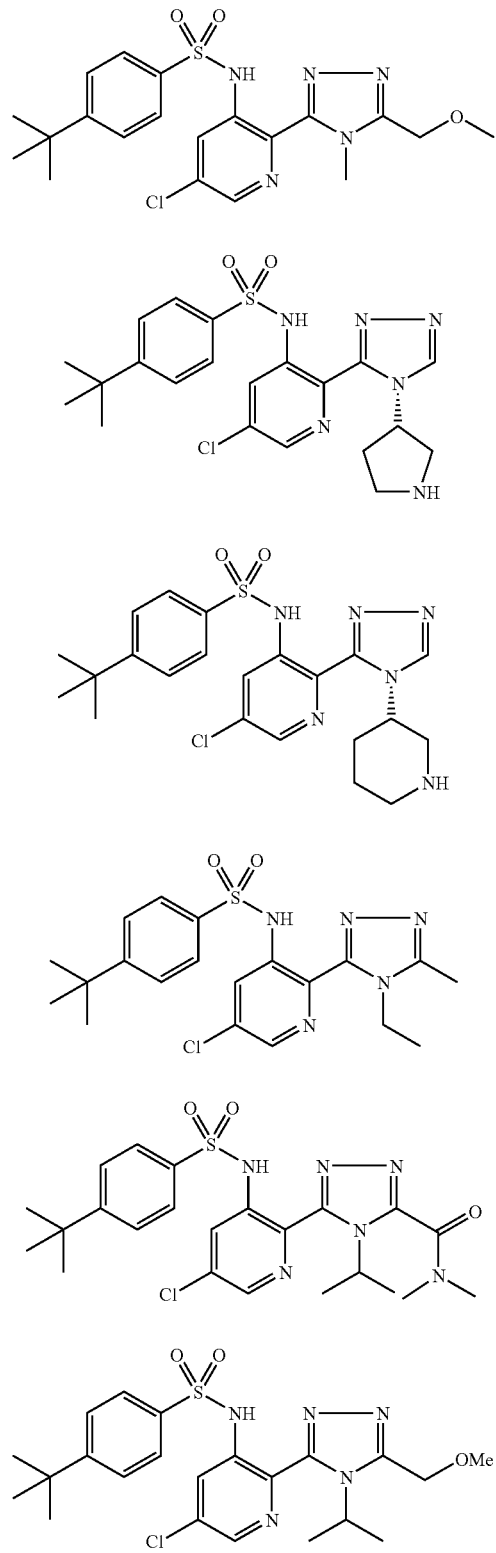
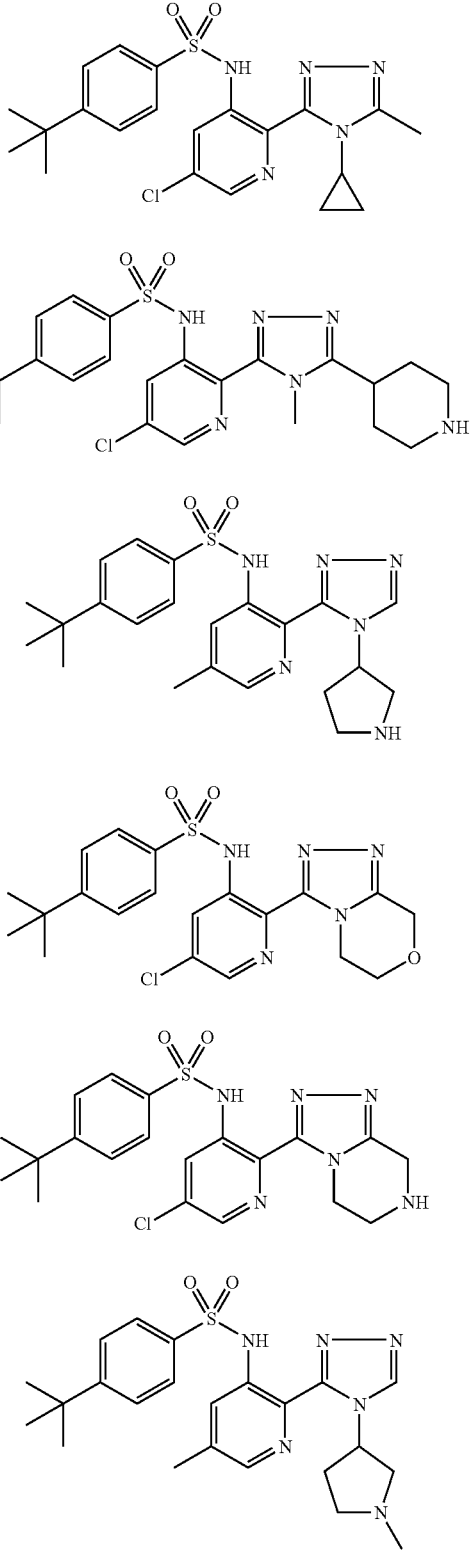

TABLE 4-continued

Compounds with CCR9 activity in one of the chemotaxis, binding or calcium mobilization assays, with IC50 < 1000 nM

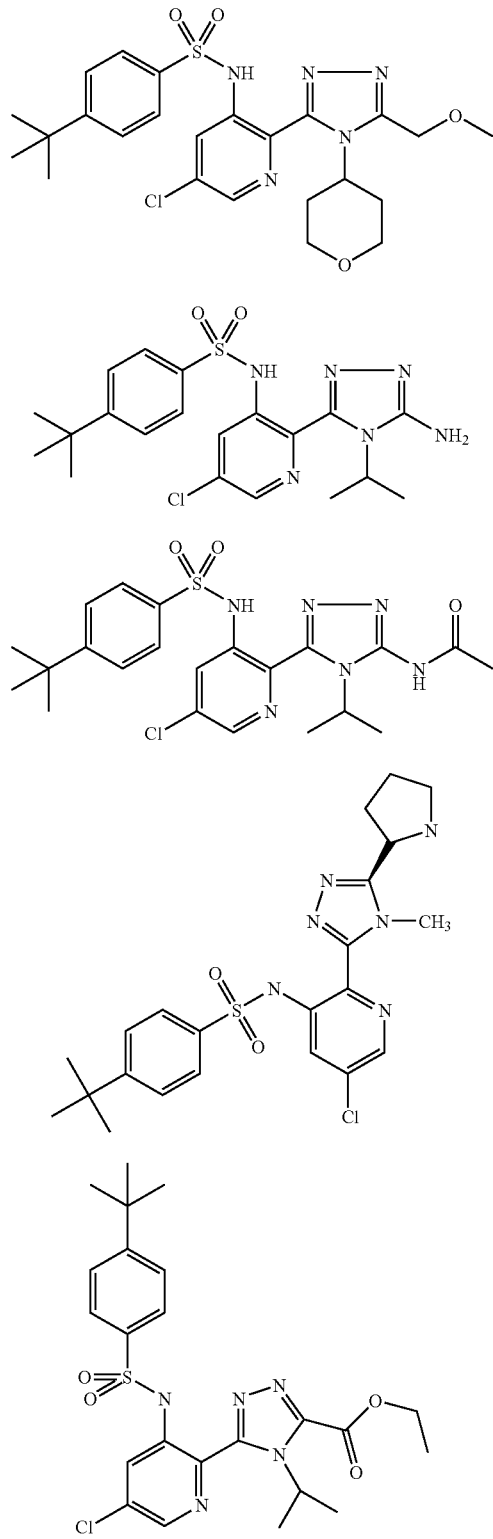

It is therefore intended that the foregoing detailed description be regarded as illustrative rather than limiting, and that it be understood that it is the following claims, including all equivalents, that are intended to define the spirit and scope of this invention.

We claim:

1. A compound of the formula (I), or a salt thereof:

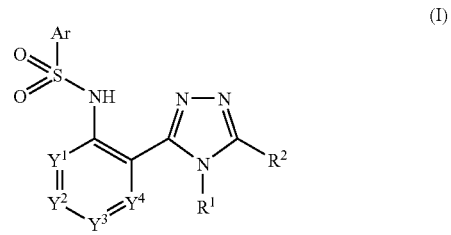

wherein
Ar is selected from the group consisting of substituted or unsubstituted $C_{6-10}$ aryl;
$Y^1$ is —$CR^{3a}$;
$Y^2$ is —$CR^{3b}$;
$Y^3$ is —$CR^{3b}$;
$Y^4$ is —N;
$R^{3a}$, $R^{3b}$, and $R^{3c}$ are each independently selected from the group consisting of hydrogen, halogen, —CN, —C(O)R$^4$, —CO$_2$R$^4$, —C(O)NR$^4$R$^5$, —OR$^4$, —OC(O)R$^4$, —OC(O)NR$^4$R$^5$, —SR$^4$, —S(O)R$^4$, —S(O)$_2$R$^4$, —S(O)$_2$NR$^4$R$^5$, —NO$_2$, —NR$^4$R$^5$, —NR$^4$C(O)R$^5$, —NR$^4$C(O)OR$^5$, —NR$^4$S(O)$_2$R$^5$, —NR$^4$C(O)NR$^5$R$^6$, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl;
$R^4$, $R^5$, and $R^6$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl;
$R^1$ is an unsubstituted isoxazolyl or an isoxazolyl substituted with 1 or 2 substituents independently selected from the group consisting of halogen, —CN, —CO$_2$R', —C(O)R', —C(O)NR'R'', —OR', —OC(O)R', —OC(O)NR'R'', —NO$_2$, —NR'C(O)R'', —NR'''C(O)NR'R'', —NR'R'', —NR'CO$_2$R'', —NR'S(O)R'', —NR'S(O)$_2$R''', —NR'''S(O)NR'R'', —NR'''S(O)$_2$NR'R'', —SR', —S(O)R', —S(O)$_2$R', —S(O)$_2$NR'R'', —NR'—C(NHR'')=NR''', —SiR'R''R''', —N$_3$, and unsubstituted $C_{6-10}$ aryl;
$R^2$ is selected from the group consisting of hydrogen, halogen, —CN, —C(O)R$^7$, —CO$_2$R$^7$, —C(O)NR$^7$R$^8$, —OR$^7$, —OC(O)R$^7$, —OC(O)NR$^7$R$^8$, —SR$^7$, —S(O)R$^7$, —S(O)$_2$R$^7$, —S(O)$_2$NR$^7$R$^8$, —NO$_2$, —NR$^7$R$^8$, —NR$^7$C(O)R$^8$, —NR$^7$C(O)OR$^8$, —NR$^7$S(O)$_2$R$^8$, —NR$^7$C(O)NR$^8$R$^9$, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl; and
$R^7$, $R^8$, and $R^9$ are each independently selected from the group consisting of hydrogen, substituted or unsubstituted $C_{1-8}$ alkyl, substituted or unsubstituted $C_{2-8}$alkenyl, substituted or unsubstituted $C_{2-8}$alkynyl, and substituted or unsubstituted $C_{6-10}$ aryl;
wherein said substituted $C_{1-8}$ alkyl, substituted $C_{2-8}$ alkenyl, and substituted $C_{2-8}$ alkynyl have 1 to (2m'=1) substituents, where the substituents are independently selected from the group consisting of halogen, —CN, —CO₂R', —C(O)R', —C(O)NR'R", —OR', —OC(O)R', —OC(O)NR'R", —NO₂, —NR'C(O)R", —NR'"C(O)NR'R", —NR'R", —NR'CO₂R", —NR'S(O)R", —NR'S(O)₂R'", —NR'"S(O)NR'R", —NR'"S(O)₂NR'R", —SR', —S(O)R', —S(O)₂R', —S(O)₂NR'R", —NR'—C(NHR")=NR'", —SiR'R"R'", —N₃, and unsubstituted C₆₋₁₀ aryl;

wherein m' is the total number of carbons in said substituted alkyl, substituted alkenyl, and substituted alkynyl;

wherein said substituted C₆₋₁₀ aryl have 1 to 5 substituents independently selected from the group consisting of halogen, —CN, —CO₂R', —C(O)R', —C(O)NR'R", oxo(=O or —O⁻), —OR', —OC(O)R', —OC(O)NR'R", —NO₂, —NR'C(O)R", —NR'"C(O)NR'R", —NR'R", —NR'CO₂R", —NR'S(O)R", —NR'S(O)₂R'", —NR'"S(O)NR'R", —NR'"S(O)₂NR'R", —SR', —S(O)R', —S(O)₂R', —S(O)₂NR'R", —NR'—C(NHR")=NR'", —SiR'R"R'", —N₃, and unsubstituted C₆₋₁₀ aryl; and wherein R', R" and R'" are each independently selected from the group consisting of: hydrogen, unsubstituted C₁₋₈ alkyl, unsubstituted C₂₋₈ alkenyl, unsubstituted C₂₋₈ alkynyl, and unsubstituted C₆₋₁₀ aryl.

2. A compound which is represented by formula (II) or a salt thereof:

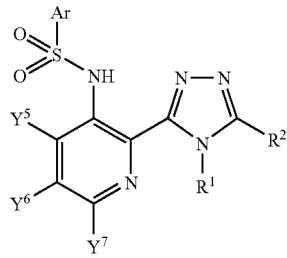

II wherein

Ar is selected from the group consisting of substituted or unsubstituted C₆₋₁₀ aryl;

Y⁵, Y⁶ and Y⁷ are each independently selected from the group consisting of hydrogen, halogen, —CN, —C(O)R¹⁵, —CO₂R¹⁵, —C(O)NR¹⁵R¹⁶, —OR¹⁵, —OC(O)R¹⁵, —OC(O)NR¹⁵R¹⁶, —SR¹⁵, —S(O)R¹⁵, —S(O)₂R¹⁵, —S(O)₂NR¹⁵R¹⁶, —NO₂, —NR¹⁵R¹⁶, —NR¹⁵C(O)R¹⁶, —NR¹⁵C(O)OR¹⁶, —NR¹⁵S(O)₂R¹⁶, —NR¹⁵C(O)NR¹⁶R¹⁷, substituted or unsubstituted C₁₋₈ alkyl, substituted or unsubstituted C₂₋₈ alkenyl, substituted or unsubstituted C₂₋₈ alkynyl, and substituted or unsubstituted C₆₋₁₀ aryl; and R¹⁵, R¹⁶ and R¹⁷ are each independently selected from the group consisting of hydrogen, substituted or unsubstituted C₁₋₈ alkyl, substituted or unsubstituted C₂₋₈ alkenyl, substituted or unsubstituted C₂₋₈ alkynyl, and substituted or unsubstituted C₆₋₁₀ aryl R¹ is an unsubstituted isoxazolyl or an isoxazolyl substituted with 1 or 2 substituents independently selected from the group consisting of halogen, —CN, —CO₂R', —C(O)R', —C(O)NR'R", —OR', —OC(O)R', —OC(O)NR'R", —NO₂, —NR'C(O)R", —NR'"C(O)NR'R", —NR'R", —NR'CO₂R", —NR'S(O)R", —NR'S(O)₂R'", —NR'"S(O)NR'R", —NR'"S(O)₂NR'R", —SR', —S(O)R', —S(O)₂R', —S(O)₂NR'R", —NR'—C(NHR")=NR'", —SiR'R"R'", —N₃, and unsubstituted C₆₋₁₀ aryl; R² is selected from the group consisting of hydrogen, halogen, —CN, —C(O)R⁷, —CO₂R⁷, —C(O)NR⁷R⁸, —OR⁷, —OC(O)R⁷, —OC(O)NR⁷R⁸, —SR⁷, —S(O)R⁷, —S(O)₂R⁷, —S(O)₂NR⁷R⁸, —NO₂, —NR⁷R⁸, —NR⁷C(O)R⁸, —NR⁷C(O)OR⁸, —NR⁷S(O)₂R⁸, —NR⁷C(O)NR⁸R⁹, substituted or unsubstituted C₁₋₈ alkyl, substituted or unsubstituted C₂₋₈ alkenyl, substituted or unsubstituted C₂₋₈ alkynyl, and substituted or unsubstituted C₆₋₁₀ aryl;

wherein said substituted C₁₋₈ alkyl, substituted C₂₋₈ alkenyl, and substituted C₂₋₈ alkynyl have 1 to (2m'=1) substituents, where the substituents are independently selected from the group consisting of halogen, —CN, —CO₂R', —C(O)R', —C(O)NR'R", —OR', —OC(O)R', —OC(O)NR'R", —NO₂, —NR'C(O)R", —NR'"C(O)NR'R", —NR'R", —NR'CO₂R", —NR'S(O)R", —NR'S(O)₂R'", —NR'"S(O)NR'R", —NR'"S(O)₂NR'R", —SR', —S(O)R', —S(O)₂R', —S(O)₂NR'R", —NR'—C(NHR")=NR'", —SiR'R"R'", —N₃, and unsubstituted C₆₋₁₀ aryl;

wherein m' is the total number of carbons in said substituted alkyl, substituted alkenyl, and substituted alkynyl;

wherein said substituted C₆₋₁₀ aryl have 1 to 5 substituents independently selected from the group consisting of halogen, —CN, —CO₂R', —C(O)R', —C(O)NR'R", oxo(=O or —O⁻), —OR', —OC(O)R', —OC(O)NR'R", —NO₂, —NR'C(O)R", —NR'"C(O)NR'R", —NR'R", —NR'CO₂R", —NR'S(O)R", —NR'S(O)₂R'", —NR'"S(O)NR'R", —NR'"S(O)₂NR'R", —SR', —S(O)R', —S(O)₂R', —S(O)₂NR'R", —NR'—C(NHR")=NR'", —SiR'R"R'", —N₃, and unsubstituted C₆₋₁₀ aryl; and wherein R', R" and R'" are each independently selected from the group consisting of: hydrogen, unsubstituted C₁₋₈ alkyl, unsubstituted C₂₋₈ alkenyl, unsubstituted C₂₋₈ alkynyl, and unsubstituted C₆₋₁₀ aryl.

3. The compound of claim 2, which is represented by formula (III) or a salt thereof:

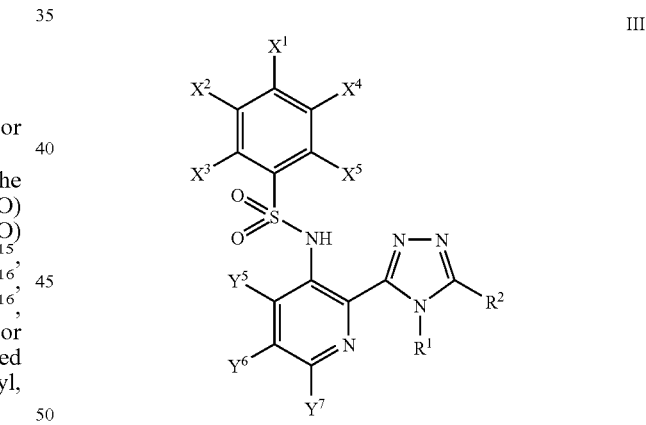

III wherein

X¹, X², X³, X⁴, and X⁵ are each independently selected from the group consisting of hydrogen, halogen, substituted or unsubstituted C₁₋₈ alkyl, substituted or unsubstituted C₂₋₈ alkenyl, substituted or unsubstituted C₂₋₈ alkynyl, —CN, —NO₂, —C(O)R¹⁸, —CO₂R¹⁸, —C(O)NR¹⁸R¹⁹, —OR¹⁸, —OC(O)R¹⁹, —OC(O)NR¹⁸R¹⁹, —NO₂, —NR¹⁸C(O)R¹⁹, —NR¹⁸C(O)NR¹⁹R²⁰, —NR¹⁸R¹⁹, —NR¹⁸CO₂R¹⁹, —NR¹⁸S(O)₂R¹⁹, —SR¹⁸, —S(O)R¹⁸, —S(O)₂R¹⁸, —S(O)₂NR¹⁸R¹⁹, and substituted or unsubstituted C₆₋₁₀ aryl; and R¹⁸, R¹⁹ and R²⁰ are each independently selected from the group consisting of hydrogen, substituted or unsubstituted C₁₋₈ alkyl, substituted or unsubstituted C₂₋₈ alkenyl, substituted or unsubstituted C₂₋₈ alkynyl, and substituted or unsubstituted C₆₋₁₀ aryl.

4. The compound of claim 3, which is represented by formula (IV), or a salt thereof:

(IV)

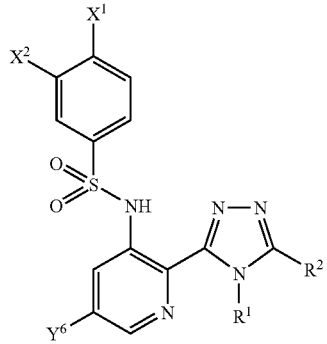

wherein $X^1$ and $X^2$ are each independently from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —CO$_2$R$^{18}$, —OR$^{18}$, —OC(O)R$^{19}$, —OC(O)NR$^{18}$R$^{19}$, —NR$^{18}$C(O)R$^{19}$, —NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —NO$_2$, and —SR$^{18}$;

$Y^6$ is selected from the group consisting of halogen, —CN, —OR$^{18}$, and substituted or unsubstituted $C_{1-8}$ alkyl;

$R^2$ is selected from the group consisting of hydrogen, halogen, —CN, —C(O)R$^7$, —CO$_2$R$^7$, —C(O)NR$^7$R$^8$, —OR$^7$, —OC(O)R$^7$, —OC(O)NR$^7$R$^8$, —SR$^7$, —S(O)R$^7$, —S(O)$_2$R$^7$, —S(O)$_2$NR$^7$R$^8$, —NO$_2$, —NR$^7$R$^8$, —NR$^7$C(O)R$^8$, —NR$^7$C(O)OR$^8$, —NR$^7$S(O)$_2$R$^8$, —NR$^7$C(O)NR$^8$R$^9$, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl;

$R^7$, $R^8$, and $R^9$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl; and $R^{18}$, $R^{19}$ and $R^{20}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl.

5. The compound of claim 3, which is represented by formula (V), or a salt thereof:

(V)

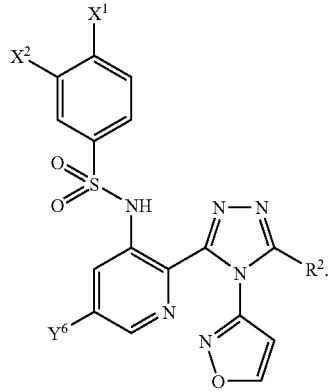

6. The compound of claim 5 wherein $Y_6$ is selected from the group consisting of halogen and methyl.

7. The compound of claim 5 wherein $X_1$ and $X_2$ are independently selected from the group consisting of hydrogen, halogen, substituted and unsubstituted $C_1$-$C_4$ alkyl, and OR$^{18}$.

8. The compound of claim 7 wherein $X_1$ is Cl and $X_2$ is CF$_3$.

9. The compound of claim 2 which is represented by formula (VIII), or a salt thereof:

(VIII)

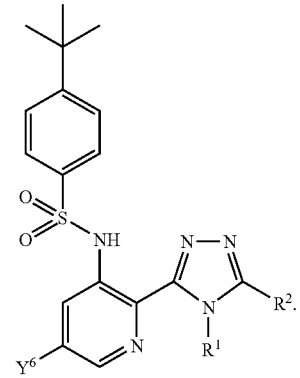

10. The compound of claim 9 which is represented by formula (IX), or a salt thereof:

(IX)

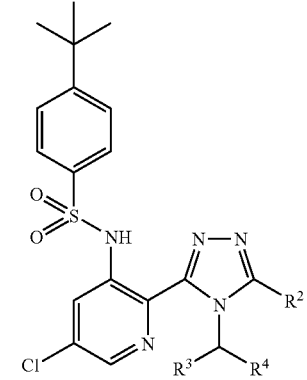

$R^3$ and $R^4$ together with the carbon which they substitute form a unsubstituted or substituted isoxazolyl.

11. The compound of claim 10 wherein $R^2$ is hydrogen.

12. The compound of claim 3 which is represented by formula (XI), or a salt thereof:

(XI)

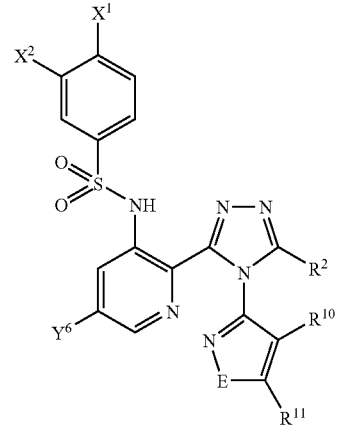

wherein $X^1$ and $X^2$ are each independently from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —$CO_2R^{18}$, —$OR^{18}$, —$OC(O)R^{19}$, —$OC(O)NR^{18}R^{19}$, —$NR^{18}C(O)R^{19}$, —$NR^{18}C(O)NR^{19}R^{20}$, —$NR^{18}R^{19}$, —$NR^{18}CO_2R^{19}$, —$NR^{18}S(O)_2R^{19}$, —$NO_2$, and —$SR^{18}$;

$Y^6$ is selected from the group consisting of halogen, —CN, —$OR^{18}$, and substituted or unsubstituted $C_{1-8}$ alkyl;

E is O;

$R^{10}$ and $R^{11}$ are each independently selected from the group consisting of hydrogen, halogen, and substituted or unsubstituted $C_{1-8}$ alkyl;

$R^2$ is selected from the group consisting of hydrogen, halogen, —CN, —$C(O)R^7$, —$CO_2R^7$, —$C(O)NR^7R^8$, —$OR^7$, —$OC(O)R^7$, —$OC(O)NR^7R^8$, —$SR^7$, —$S(O)R^7$, —$S(O)_2R^7$, —$S(O)_2NR^7R^8$, —$NO_2$, —$NR^7R^8$, —$NR^7C(O)R^8$, —$NR^7C(O)OR^8$, —$NR^7S(O)_2R^8$, —$NR^7C(O)NR^8R^9$, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl;

$R^7$, $R^8$, and $R^9$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl; and $R^{18}$, $R^{19}$ and $R^{20}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, and substituted or unsubstituted $C_{6-10}$ aryl.

13. The compound of claim 11 which is represented by formula (IX), or salts thereof wherein $R^2$ is hydrogen.

14. A compound selected from the following:

ethyl 5-(5-chloro-3-(4-chloro-3-(trifluoromethyl) phenylsulfonamido)pyridin-2-yl)-4-(isoxazol-3-yl)-4H-1,2,4-triazole-3-carboxylate;

5-(3-(4-chloro-3-(trifluoromethyl)phenylsulfonamido)-5-methylpyridin-2-yl)-4-(isoxazol-3-yl)-4H-1,2,4-triazole-3-carboxamide;

5-(5-chloro-3-(3,4-dichlorophenylsulfonamido)pyridin-2-yl)-4-(isoxazol-3-yl)-4H-1,2,4-triazole-3-carboxamide;

5-(5-chloro-3-(4-chloro-3-(trifluoromethyl)phenylsulfonamido) pyridin-2-yl)-4-(isoxazol-3-yl)-4H-1,2,4-triazole-3-carboxamide;

5-(5-chloro-3-(4-chloro-3-(trifluoromethyl)phenylsulfonamido) pyridin-2-yl)-4-(isoxazol-3-yl)-N,N-dimethyl-4H-1,2,4-triazole-3-carboxamide;

5-(5-chloro-3-(4-chloro-3-(trifluoromethyl) phenylsulfonamido) pyridin-2-yl)-N-ethyl-4-(isoxazol-3-yl)-4H-1,2,4-triazole-3-carboxamide;

5-(5-chloro-3-(4-chloro-3-(trifluoromethyl) phenylsulfonamido) pyridin-2-yl)-N-ethyl-4-(isoxazol-3-yl)-N-methyl-4H-1,2,4-triazole-3-carboxamide;

5-(5-chloro-3-(4-chloro-3-(trifluoromethyl) phenylsulfonamido) pyridin-2-yl)-N-isopropyl-4-(isoxazol-3-yl)-4H-1,2,4-triazole-3-carboxamide;

5-(5-chloro-3-(4-methyl-3-(trifluoromethyl) phenylsulfonamido) pyridin-2-yl)-4-(isoxazol-3-yl)-4H-1,2,4-triazole-3-carboxamide;

3,4-dichloro-N-(5-chloro-2-(4-(isoxazol-3-yl)-4H-1,2,4-triazol-3-yl)pyridin-3-yl)benzenesulfonamide;

4-chloro-N-(5-chloro-2-(4-(isoxazol-3-yl)-5-(methoxymethyl)-4H-1,2,4-triazol-3-yl)pyridin-3-yl)-3-(trifluoromethyl)benzenesulfonamide;

4-chloro-N-(5-chloro-2-(5-(hydroxymethyl)-4-(isoxazol-3-yl)-4H-1,2,4-triazol-3-yl)pyridin-3-yl)-3-(trifluoromethyl)benzenesulfonamide;

N-(2-(5-bromo-4-(isoxazol-3-yl)-4H-1,2,4-triazol-3-yl)-5-chloropyridin-3-yl)-4-chloro-3-(trifluoromethyl)benzenesulfonamide; and N-(5-bromo-2-(4-(isoxazol-3-yl)-4H-1,2,4-triazol-3-yl) pyridin-3-yl)-4-chloro-3-(trifluoromethyl)benzenesulfonamide; or a salt thereof.

15. A compound that is 5-(3-(4-chloro-3-(trifluoromethyl) phenylsulfonamido)-5-methylpyridin-2-yl)-4-(isoxazol-3-yl)-4H-1,2,4-triazole-3-carboxamide, or a salt thereof.

16. A compound that is 5-(3-(4-chloro-3-(trifluoromethyl) phenylsulfonamido)-5-methylpyridin-2-yl)-4-(isoxazol-3-yl)-4H-1,2,4-triazole-3-carboxamide.

17. A compound that is 5-(5-chloro-3-(4-chloro-3-(trifluoromethyl)phenylsulfonamido)pyridin-2-yl)-4-(isoxazol-3-yl)-4H-1,2,4-triazole-3-carboxamide, or a salt thereof.

18. A compound that is 5-(5-chloro-3-(4-chloro-3-(trifluoromethyl)phenylsulfonamido)pyridin-2-yl)-4-(isoxazol-3-yl)-4H-1,2,4-triazole-3-carboxamide.

\* \* \* \* \*